US012111289B2

(12) United States Patent
Fincke et al.

(10) Patent No.: US 12,111,289 B2
(45) Date of Patent: Oct. 8, 2024

(54) SYSTEMS AND METHODS FOR IMAGING CORTICAL BONE AND SOFT TISSUE

(71) Applicant: Massachusetts Institute of Technology, Cambridge, MA (US)

(72) Inventors: Jonathan Randall Fincke, Lincoln, MA (US); Brian W. Anthony, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 793 days.

(21) Appl. No.: 17/255,410

(22) PCT Filed: Jun. 26, 2019

(86) PCT No.: PCT/US2019/039279
§ 371 (c)(1),
(2) Date: Dec. 22, 2020

(87) PCT Pub. No.: WO2020/006097
PCT Pub. Date: Jan. 2, 2020

(65) Prior Publication Data
US 2021/0215642 A1 Jul. 15, 2021

Related U.S. Application Data

(60) Provisional application No. 62/690,041, filed on Jun. 26, 2018.

(51) Int. Cl.
*G03B 42/06* (2021.01)
*G01N 29/06* (2006.01)
(Continued)

(52) U.S. Cl.
CPC ..... *G01N 29/0672* (2013.01); *G01N 29/2418* (2013.01); *G01N 33/12* (2013.01);
(Continued)

(58) Field of Classification Search
CPC ... G01N 29/0672; G01N 29/2418; A61B 8/13
See application file for complete search history.

(56) References Cited

U.S. PATENT DOCUMENTS 7,725,151 B2 * 5/2010 van der Weide .... A61B 5/6843
600/407
2004/0254457 A1 12/2004 van der Weide
(Continued)

FOREIGN PATENT DOCUMENTS

CA 2 495 745 A1 3/2004
WO WO 2011012274 A1 * 2/2011 ......... G01N 21/1702

OTHER PUBLICATIONS

Bernard et al., "Ultrasonic computed tomography based on full-waveform inversion for bone quantitative imaging," Phys. Med. Biol., 62, 7011-7035 (2017).
(Continued)

*Primary Examiner* — Mark Hellner
(74) *Attorney, Agent, or Firm* — Hamilton, Brook, Smith & Reynolds, P.C.

(57) ABSTRACT

Systems and methods are provided for imaging of soft and hard tissues with ultrasound. Such systems and methods can provide for non-contact and quantitative ultrasound images of bone and soft tissue. A method for imaging a biological body segment of soft and hard tissues includes setting geometry and material properties according to a model of the biological body segment to thereby generate a simulated time series data set. The method further includes collecting reflective and transmissive time series data of the biological body segment to thereby form an experimental time series data set and minimizing a difference between the simulated time series data set and the experimental time series data set, thereby imaging the biological body segment. Regularizing travel-time and/or using full waveform tomographic tech-
(Continued)

niques with level set methods enable recovery of cortical bone geometry.

22 Claims, 44 Drawing Sheets

(51) Int. Cl.
*G01N 29/24* (2006.01)
*G01N 33/12* (2006.01)
*A61B 5/00* (2006.01)
*A61B 8/13* (2006.01)

(52) U.S. Cl.
CPC ............... *A61B 5/0095* (2013.01); *A61B 8/13* (2013.01); *G01N 2291/02475* (2013.01)

(56) References Cited

U.S. PATENT DOCUMENTS

2010/0130832 A1   5/2010  Lang et al.
2016/0030007 A1*  2/2016  Tsujita ................... A61B 8/485
                                                    600/441

OTHER PUBLICATIONS

Canny, "A Computational Approach to Edge Detection," IEEE Trans. Pattern Anal. Mach Intell., (1986).
Duda and Hart, "Use of Hough Transformation to Detect Lines and Curves in Pictures," Graph. Image. Process., 15, 11-15 (1972).
International Preliminary Report on Patentability for International Application No. PCT/US2019/039279, "Systems and Methods for Imaging Cortical Bone and Soft Tissue" dated Jan. 7, 2021.
Kadu, A., and Leeuwen, T. Van, "A Parametric Level-Set Approach for Seismic Full-Waveform Inversion," SEG Tech. Progr. Expand. Abstr. (2016).
Zhang et al., "A single element 3D ultrasound tomography system," Proc. Annu. Int. Conf. IEEE Eng. Med. Biol. Soc. EMBS (2015).
Zheglova et al., "2-D reconstruction of boundaries with level set inversion of traveltimes", "Geophysical Journal", Geophyiscs J. Int. (2012).
International Search Report and Written Opinion for International Application No. PCT/US2019/039279, entitled "Systems and Methods for Imaging Cortical Bone and Soft Tissue," mailed on Nov. 1, 2019.

* cited by examiner

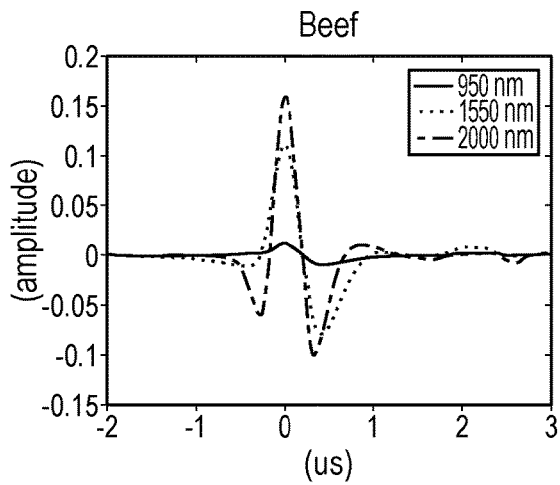
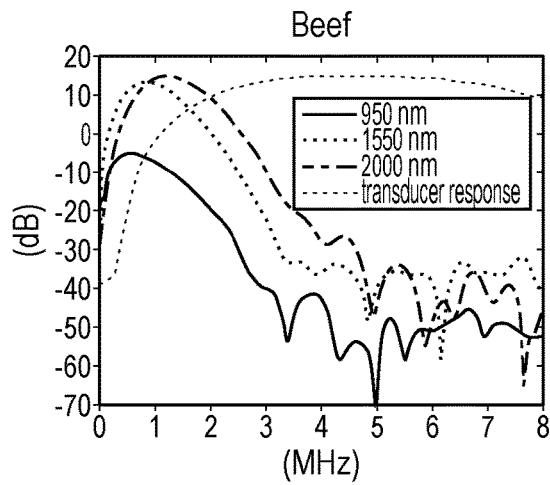
FIG. 4A
FIG. 4B
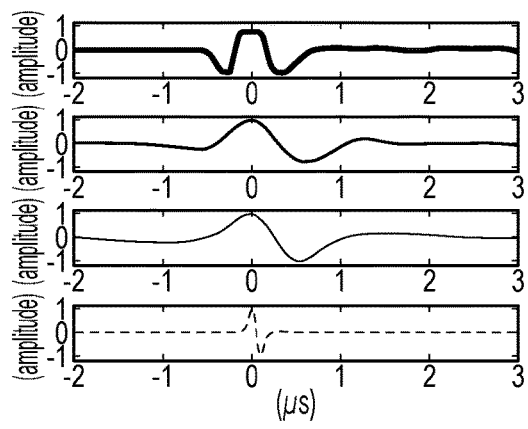
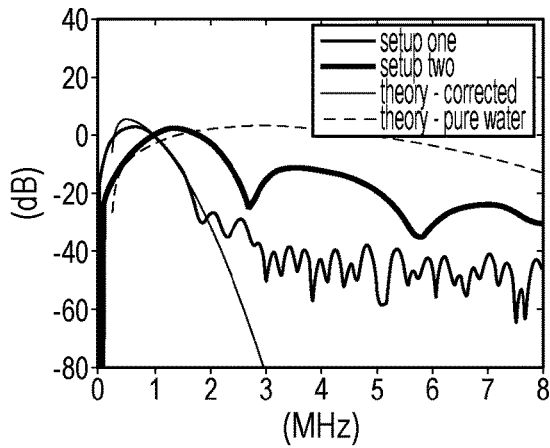
FIG. 5A
FIG. 5B

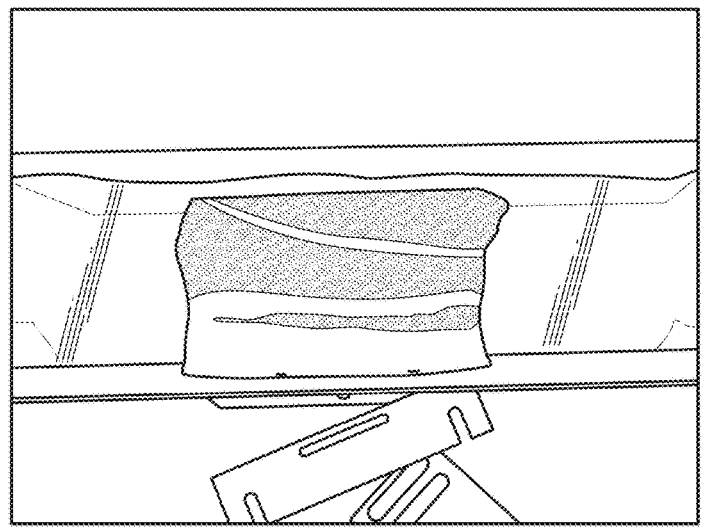
FIG. 14A
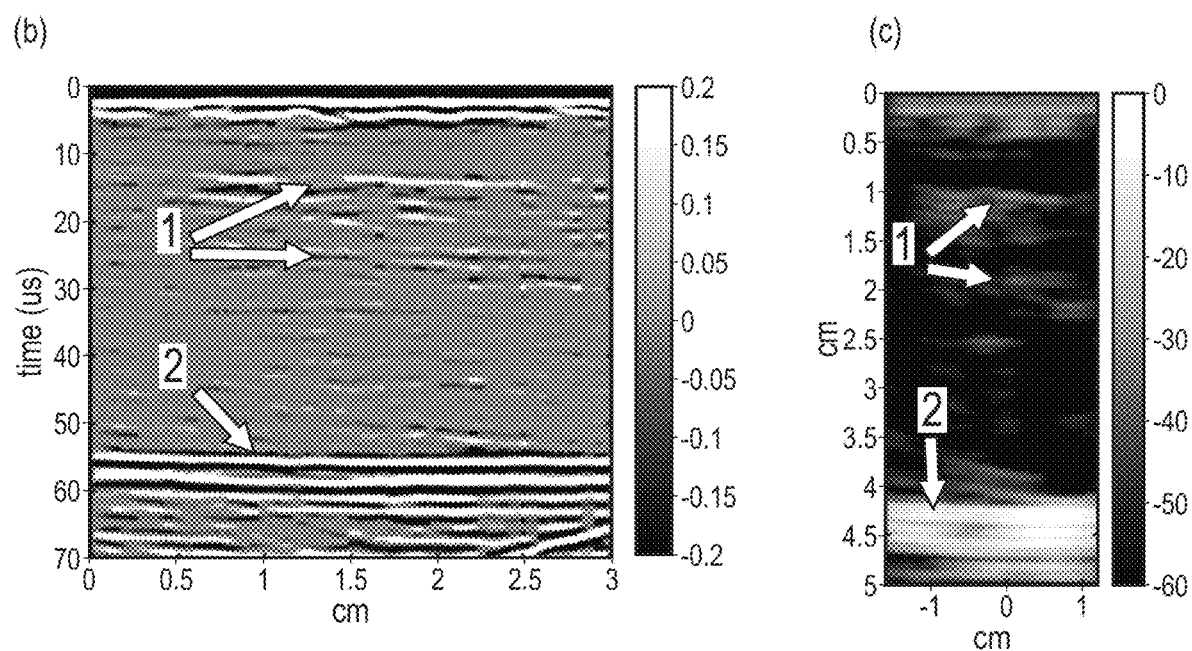
FIG. 14B
FIG. 14C

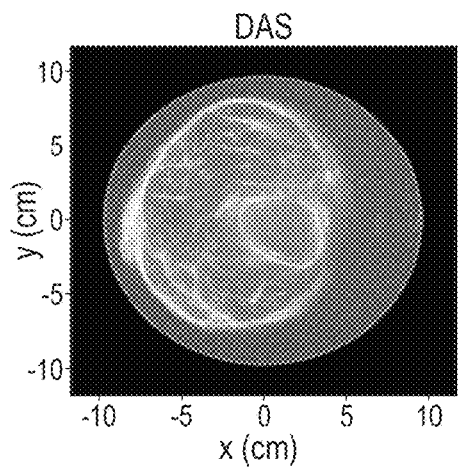 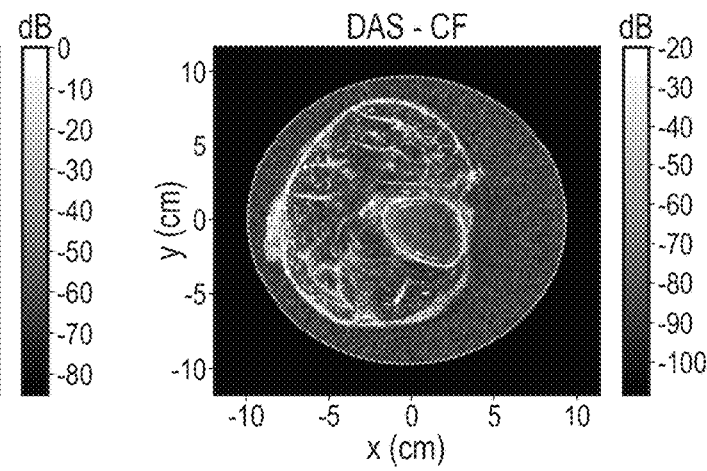
FIG. 28A  FIG. 28B
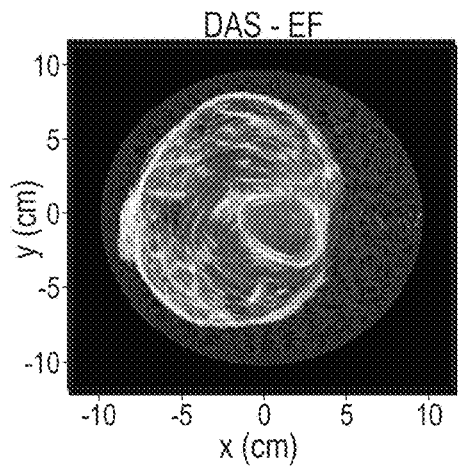 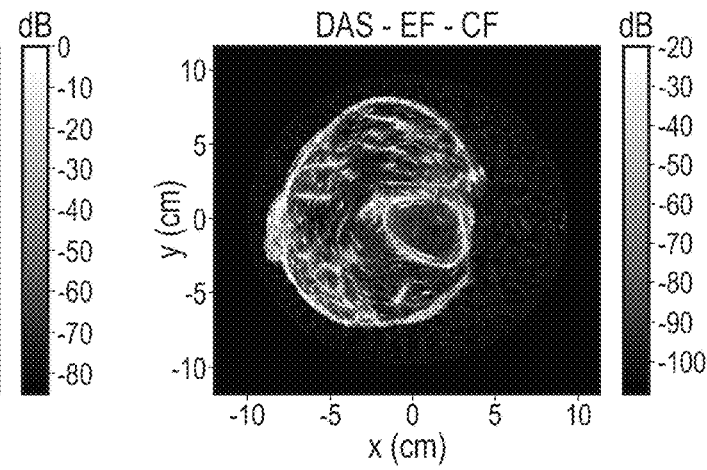
FIG. 28C  FIG. 28D
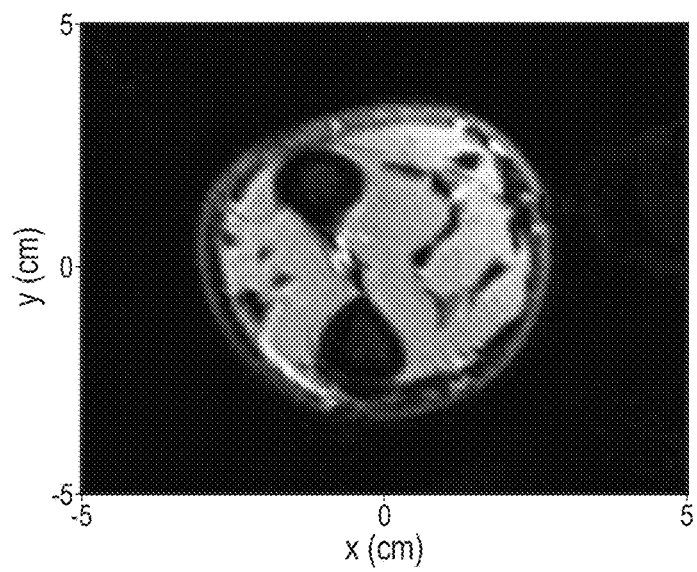
FIG. 29

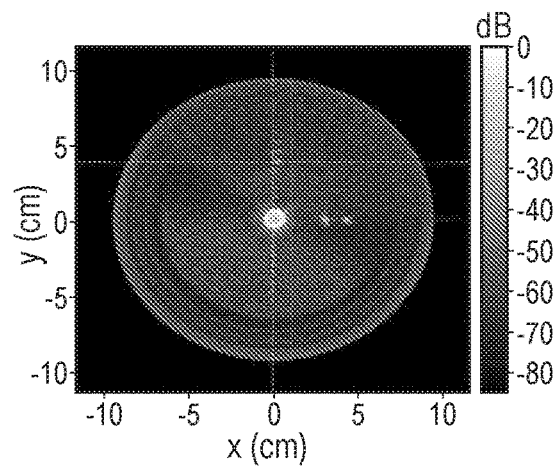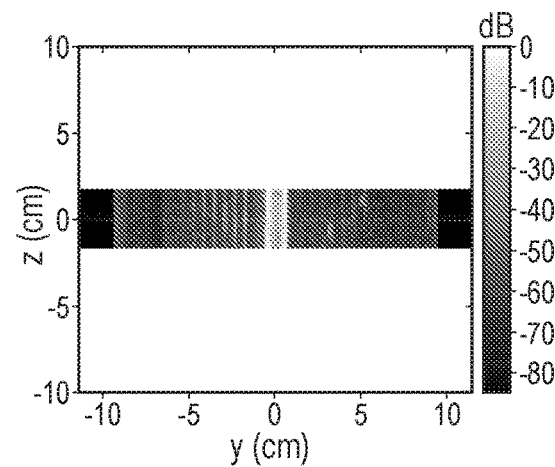
FIG. 32A                     FIG. 32B
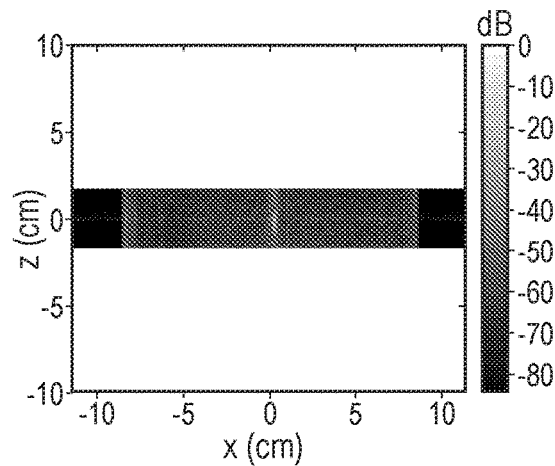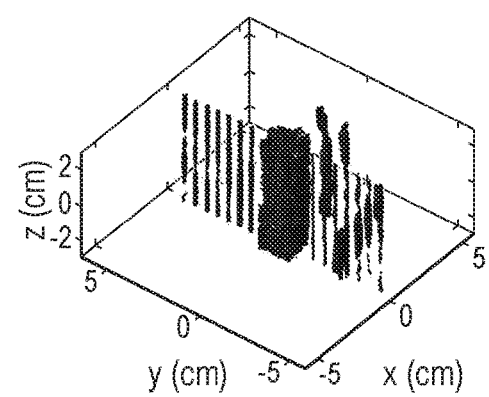
FIG. 32C                     FIG. 32D

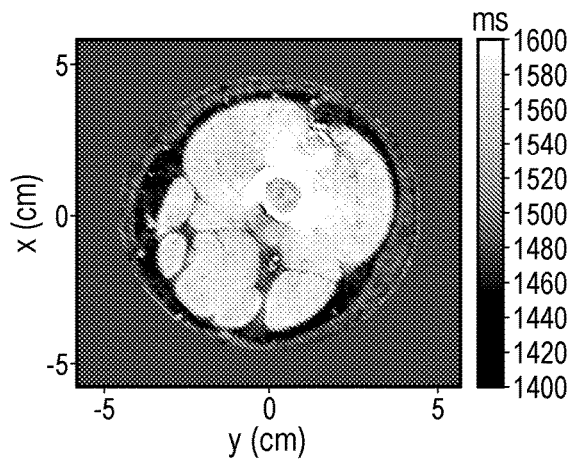
FIG. 48A
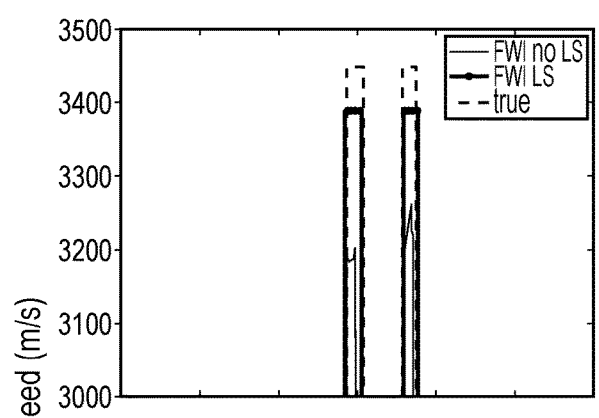
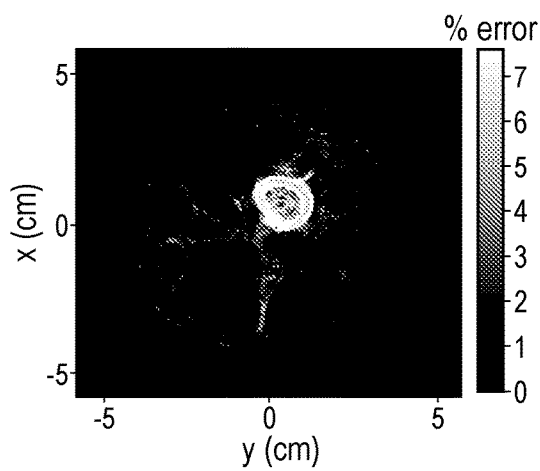
FIG. 48B
FIG. 48C

SYSTEMS AND METHODS FOR IMAGING CORTICAL BONE AND SOFT TISSUE

RELATED APPLICATION

This application is the U.S. National Stage of International Application No. PCT/US2019/039279, filed Jun. 26, 2019, which designates the U.S., published in English, and claims the benefit of U.S. Provisional Application No. 62/690,041, filed on Jun. 26, 2018. The entire teachings of the above application is incorporated herein by reference.

GOVERNMENT SUPPORT

This invention was made with government support under Grant No. FA8702-15-D-0001 from the U.S. Air Force. The government has certain rights in the invention.

BACKGROUND

Imaging the human body interior with medical ultrasound systems is a regular and ubiquitous practice in medicine. Ultrasound images can provide valuable information about heart health, needle placement, vascular health, and potentially cancerous tissue, among many other applications. Ultrasound has advantages over magnetic resonance imaging (MRI) and x-ray computed tomography (CT) imaging modalities, such as low cost, low safety risk, and system portability. The competing imaging modalities to ultrasound (e.g., MRI and CT) have advantages, such as delivering non-contact, large volume (e.g., 1000 $cm^3$), repeatable, and sometimes quantitative images of the human body. Additionally, MRI and CT-based methods can image bone without difficulty. These capabilities make MRI and CT the work-horse imaging modalities for detecting cancer, surgical planning, and inter-operative imaging, among many other applications.

SUMMARY

Systems and methods are provided for imaging of soft and hard tissues with ultrasound. Such systems and methods can provide for non-contact and quantitative ultrasound images of bone and soft tissue.

A method for imaging a biological body segment of soft and hard tissues includes setting geometry and material properties according to a model of the biological body segment to thereby generate a simulated time series data set. The method further includes collecting reflective and transmissive time series data of the biological body segment to thereby form an experimental time series data set and minimizing a difference between the simulated time series data set and the experimental time series data set, thereby imaging the biological body segment.

A system for imaging a biological body segment of soft and hard tissues includes at least one sensor configured to collect reflective and transmissive time series data of the biological body segment and a processor configured to: generate a simulated time series data set based on geometry and material properties according to a model of the biological body segment, receive the collected reflective and transmissive time series data, generate an experimental time series data set from the received collected reflective and transmissive time series data, and minimize a difference between the simulated time series data set and the experimental time series data set to thereby image the biological body segment.

The method and system can include application of a level set technique including a full waveform inversion for imaging the biological body segment. The reflective and transmissive time series data can be collected by employing an ultrasound transducer that emits an ultrasound beam of known beam geometry for reflection and transmission at the biological body segment. The known beam geometry can be, for example, a planar beam or a spherical beam, although other geometries are possible and can depend on a tissue to be imaged. The model of the biological body segment can be modified. For example, the model can be modified to more accurately emulate experimental time series data. Alternatively, or in addition, the model can be modified to include at least one of the following: prior information about the biological tissue being imaged; prior information about a motion trajectory of one or more transducers employed in collecting the reflective and transmissive time series data; a model of a motion trajectory of one or more transducers employed in collecting the reflective and transmissive time series data; prior information about a response of one or more transducers employed in collecting the reflective and transmissive time series data; and a model of a response of one or more transducers employed in collecting the reflective and transmissive time series data.

The simulated time series data can be modified to more accurately emulate experimental time series data. For example, the simulated time series data can be modified by any of the following: adding white noise to the simulated data set to thereby replicate a signal-to-noise ratio of experimental data employed to form the simulated time series data set; adding a random position error value to source and receiver positions employed during formation of the simulated time series data set; and employing at least one level set technique to define a homogenous region of the simulated data set on a grid that is smaller than that of the simulated data set. The level set technique can include full waveform inversion.

Minimizing the difference between the simulated time series data set and the experimental time series data set can include full waveform inversion and/or regularizing travel time. The minimization of the difference can include a level set region segmentation of at least one portion or component of the biological body segment. Generating simulated time series data can employ at least one tissue boundary detection process. Collecting the reflective and transmissive time series data can employ at least one of a water-immersed ultrasound transducer and a laser.

Collecting the reflective and transmissive time series data can include ultrasound tomography that employs a tank-based ultrasound system that includes at least two single-element transducers mounted at a tank of the tomography system. Alternatively, or in addition, multi-element transducers can be mounted at the tank of the tomography system. The at least two transducers can be mounted at different distances from a center of the tank, or at same distances from a center of the tank. Multi-aperture time series data can be obtained from the transducers.

A tank-based ultrasound computed tomography system includes an immersion tank, at least one ultrasound transducer within the immersion tank that emits an ultrasound beam, and at least one ultrasound receiver that can detect reflection and transmission of the ultrasound beam following reflection and transmission of the planar ultrasound beam off or through a biological body segment.

The tank-based ultrasound computed tomography system can further include a processor configured to receive reflection and transmission data received by the at least one ultrasound transducer, generate a simulated time series data set based on set geometry and material properties according to a model of the biological body segment, generate an experimental time series data set from the received reflection and transmission data, and minimize a difference between the simulated time series data set and the experimental time series data set to thereby image the biological body segment.

The ultrasound beam can be of a known beam geometry, such as a planar geometry or a spherical geometry.

Such systems and methods can advantageously provide quantitative information about bone and soft tissue mechanical properties of the biological body segment in addition to images of the body segment, in contrast with conventional imaging techniques, such as MRI, which do not prove quantitative tissue information. Such systems and methods, when applied to ultrasound, can also provide for more cost-effective imaging of biological body segments than conventional CT and MR imaging techniques. Level set methods can supplement quantitative image reconstruction methods, such as full waveform inversion (FWI) methods, to account for sharp changes in sound speed and density between bone and soft tissue regions of the biological body segment, which can provide for more computationally efficient and accurate results. FWI is a class of imaging techniques that are based on using content of sound or ultrasound signals for extracting physical parameters of a medium sampled by waves.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 3A illustrates a first experimental setup in which a generation laser is used to excite an acoustic wave at a surface of a tissue sample, the wave detected by the piezoelectric transducer at the bottom of the sample. A mirror scans the generation laser along the surface of the sample. Two steel rods are included in the sample as test targets. FIG. 3B illustrates a second experimental setup in which a piezoelectric transducer is lightly contacted with a top of a tissue sample and emits an acoustic wave, which is detected by a piezoelectric transducer at the bottom of the sample. Two steel rods are included in the sample as test targets. FIG. 3C illustrates a third experimental setup in which a generation laser excites an acoustic wave at a surface of a tissue sample, the wave detected by a piezoelectric transducer at a surface of the sample. Two steel rods are included in the sample as test targets.

FIGS. 4A-4B are graphs of laser ultrasound (LUS) source waveforms and spectra representative of a full data set for a beef sample. FIG. 4A is graph of LUS source waveforms for the beef sample at optical wavelengths of 950 nm, 1550 nm, and 2030 nm. FIG. 4A is a graph of spectra of the waveforms of FIG. 4A calculated with a Hanning window over roughly the −1 to 1 µs interval and the frequency response of the receiving transducer.

FIGS. 5A-5B are graphs of time domain waveforms and spectra acquired from a beef sample using the first and second experimental setups plotted with theoretical predictions. FIG. 5A depicts the time domain waveforms. The thick black line represents the data from the second experimental setup using a piezoelectric transducer to send and receive the acoustic signal. The gray line represents the LUS source waveform acquired in the beef sample with a 1550 nm wavelength optical pulse. The thin black line represents a waveform according to Eq. 18 corrected for acoustic attenuation in beef (−2.9 dBcm-MHz), the transducer response, and a surface roughness factor of $\sigma = 3.4 \times 10^{-4}$ m. The dashed line is a waveform according to Eq. 17 corrected for the transducer response. FIG. 5B depicts the spectra of the signals in FIG. 5A with the same line coding. The steeper decrease in signal amplitude with frequency for the data from the first experimental setup (gray line) is shown in comparison with the second experimental setup (thick black line).

FIG. 6A illustrates signal energy vs. optical wavelength for a beef sample. FIG. 6B illustrates signal energy vs. optical wavelength for a chicken sample. FIG. 6C illustrates signal energy vs. optical wavelength for a pork sample. Signal energy on a log scale (unitless) is provided on the left axes of FIGS. 6A-6C, and the absorption coefficient of water on a log scale (unit less) is provided on the right axes of FIGS. 6A-6C.

FIG. 7A is an image resulting from the data set using an 810 nm generation laser wavelength. FIG. 7B is an image resulting from the data set using a 1064 nm generation laser wavelength. FIG. 7C is an image resulting from the data set using a 1550 nm generation laser wavelength. FIG. 7D is an image resulting from the data set using a 2000 nm generation laser wavelength.

FIG. 10A illustrates acoustic waveforms collected from a chicken sample. FIG. 10B illustrates spectra of the waveforms in FIG. 10A calculated with a Hanning window over roughly the −1 to 1 µs interval. FIG. 10C illustrates acoustic waveforms collected from a pork sample. FIG. 10D illustrates spectra of the waveforms in FIG. 10C calculated with a Hanning window over roughly the −1 to 1 µs interval.

FIG. 11A is an image of the first sample showing the soft tissue structure of the sample. FIG. 11B is an image of processed traces. Reflections from the tissue internal boundaries at 10, 20 and 30 μs are evident. FIG. 11C is an LUS image of the first sample generated from the traces in FIG. 11B. The layer structures are visible near 0.75 and 1.25 cm depths. The scattering diffraction pattern visible in FIG. 11B is the bright spot seen at 2.25 cm depth in FIG. 11C.

FIG. 12A is an image of the first sample showing the soft tissue structure of the tissue sample with the inserted needles. FIG. 12B is an image of the processed traces. Reflections from the tissue internal boundaries at 10 and 20 μs are evident and arcs in the image are the reflected waveforms from the needles. FIG. 12C is an LUS image of the sample generated from the traces in FIG. 12B. The layer structures are visible near 1 and 1.75 cm depths. The rods are located at 1 cm and 2.25 cm depths. The reflection from the tissue and aluminum block interface is visible at 4 cm depth.

FIG. 13A is an LUS image of the sample without needles. FIG. 13B is an LUS image of the sample with inserted needles. FIG. 13C is a clinical image of the sample with inserted needles. FIG. 13D is an image taken from a research system with a scan replicating the LUS system scan. The needles are not visible in the image most likely due to specular reflections off the needles.

FIGS. 14A-C illustrate a second sample, LUS traces, and an image obtained from scanning the second sample. FIG. 14A is an image of the second sample showing the soft tissue structure of the sample. FIG. 14B is an image of processed traces. Reflections from the tissue internal boundaries between 15 and 30 μs are evident. FIG. 14C is an LUS image of the second sample generated from the traces in FIG. 14B. The layer structures are visible near 1, 2, and 2.5 cm depths.

FIG. 15A is an image of the second sample showing the soft tissue structure of the sample and the needle locations. FIG. 15B is an image of the processed traces. Reflections from the tissue internal boundaries between 15 and 30 s are evident. FIG. 15C is an LUS image of the sample generated from the traces in FIG. 15B. The layer structures are visible near 1, 2 and 2.5 cm depths. The needles (rods) are located at 3 cm and 3.25 cm depths. The reflection from the tissue and aluminum block interface is visible at 4 cm depth.

FIG. 16A is an LUS image of the sample without needles. FIG. 16B is an LUS image of the sample with inserted needles. FIG. 16C is a clinical image of the sample with rods inserted. FIG. 16D is an image taken from a research system with a scan replicating the LUS system scan.

FIG. 17A is an image of the third sample showing the soft tissue structure of the sample. FIG. 17B is an image of the processed traces. Reflections from the tissue internal boundaries between 10 and 40 μs are evident. FIG. 17C is an LUS image of the sample generated from the traces in FIG. 17B. The layer structures are visible near 0.75, 1.25, and 2 cm depths.

FIG. 18A is an image of the sample showing the soft tissue structure of the sample and the needle locations. FIG. 18B is an image of the processed traces. Reflections from the tissue internal boundaries near 10 s are evident. FIG. 18C is an LUS image of the sample generated from the traces in FIG. 18B. A layer structure is visible near 0.75 cm depth. The rods are located at 0.75 cm and 1.5 cm depths. The reflection from the tissue back surface is seen at 2.6 cm depth.

FIG. 19A is an LUS image of the third sample without needles. FIG. 19B is an LUS image of the third sample with needles inserted. FIG. 19C is a clinical image of the sample with inserted rods.

FIG. 23A is an image reconstructed using conventional Delay and Sum (DAS) and exhibiting large degradation from sidelobes of stronger scatterers. FIG. 23B is an image reconstructed using DAS with a coherence factor (CF) applied. The noise floor is reduced compared to the image of FIG. 23A. FIG. 23C is an image reconstructed using DAS plus Echo Flow (EF) showing reduced sidelobe interference, making the skin boundary more visible. FIG. 23D is an image reconstructed using DAS with EF and CF applied showing reduction in sidelobe levels, as well as the noise floor.

FIG. 25A is a conventional DAS image exhibiting large degradation from sidelobes of the post. FIG. 25B is a DAS image with CF applied. The noise floor is reduced compared to FIG. 25A, but degradation of the image is still present from sidelobe interference FIG. 25C is a DAS plus EF image showing reduced sidelobe interference, making the threads more visible. FIG. 25D is a DAS image with EF and CF applied showing reduction in sidelobe levels as well as the noise floor.

FIG. 27A is a conventional DAS image exhibiting large degradation from sidelobes of the bone. FIG. 27B is a DAS image with CF applied. The noise floor is reduced compared to FIG. 27A, but degradation of the image is still present from sidelobe interference. FIG. 27C is a DAS plus EF image showing reduced sidelobe interference, making the outer boundary of the shank and soft tissue features more visible. FIG. 27D is a DAS image with EF and CF applied showing reduction in sidelobe levels as well as the noise floor.

FIGS. 28A-D are ultrasound images of a second beef shank ("beef shank 2" or "bovine shank 2"). The images show the bone in the center of the image and connective tissue and fat regions. FIG. 28A is a conventional DAS image exhibiting large degradation from sidelobes of the bone. FIG. 28B is a DAS image with CF applied. The noise floor is reduced compared to FIG. 28A, but degradation of the image is still present from sidelobe interference, which is creating the bright returns outside the tissue region. FIG. 28C is a DAS plus EF image showing reduced sidelobe interference, making the outer boundary of the shank and soft tissue features more visible. FIG. 28D is a DAS image with EF and CF applied showing reduction in sidelobe levels as well as the noise floor.

FIG. 29 is an MRI image of a human forearm taken from the same slice as the ultrasound images in FIGS. 30A-D. The MRI is from a 3T scanner using UTE sequences and a body coil.

FIG. 30A is a conventional DAS image exhibiting large degradation from sidelobes of the bones. FIG. 30B is a DAS image with CF applied. The noise floor is reduced compared to FIG. 30A, but degradation of the image is still present from sidelobe interference. FIG. 30C is a DAS plus EF image showing reduced sidelobe interference, making the outer boundary and soft tissue features more visible. FIG. 30D is a DAS image with EF and CF applied showing reduction in sidelobe levels as well as the noise floor.

FIG. 31A is a conventional DAS image exhibiting large degradation from sidelobes of the bone. FIG. 31B is a DAS image with CF applied. The noise floor is reduced compared to FIG. 31A, but degradation of the image is still present from sidelobe interference, which is characterized by the strong signal in the water region of the image. FIG. 31C is a DAS plus EF image showing reduced sidelobe interference, making the outer boundary and soft tissue features more visible. FIG. 31D is a DAS image with EF and CF applied showing reduction in sidelobe levels as well as the noise floor.

FIGS. 32A-D are volumetric images of the thread phantom constructed from data collected with a 1.0 MHz transducer using a DAS-EF-CF process. FIG. 32A is an x-y plane image of the thread phantom from the slice at z=−1 cm showing the threads and central post of the phantom. The white dashed lines indicate the locations of the y-z and x-z image planes in FIGS. 32B and 32C. FIG. 32B is an y-z slice of the volume at x=0 cm showing the vertical structure of the threads and knots on the added threads. The white dashed lines show the locations of the x-y and x-z image. planes in FIGS. 32A and 32C. FIG. 32C is an x-z plane image from the slice y=3.89 cm showing the vertical structure of a thread with a knot at z=−1 cm. The white lines show the locations of the x-y and y-z image planes in FIGS. 32A and 32B. FIG. 32D is a volumetric rendering of the thread phantom constructed from an isosurface. extracted from the image volume.

FIG. 33A is an x-y plane image of the beef shank from the slice at z=2.1 cm showing the bone, internal soft tissue structure, and outer boundary of the shank. The white dashed lines indicate the locations of the y-z and x-z image planes in FIGS. 33B and 33C. FIG. 33B is a y-z slice of the volume at x=−2 cm showing the vertical structure of the soft tissue and bone. The white dashed lines show the locations of the x-y and x-z image planes in FIGS. 33A and 33C. FIG. 33C is an x-z plane image from the slice y=2 cm showing the vertical structure of the soft tissue and bone. The white lines show the locations of the x-y and y-z image planes in FIGS. 33A and 33C. FIG. 33D is a partial volumetric rendering of beef shank 2. Shown in blue is an isosurface constructed from the image volume. The gray scale panels show slices of the image volume.

FIG. 34A is an x-y plane image at z=2.1 cm showing the bone cross section, soft tissue structure, and outer boundary of the shank. The white dashed lines indicate the locations of the y-z and x-z image planes in FIGS. 34A and 34C. FIG. 34B is a y-z slice of the volume at x=−2 cm showing the vertical structure of the soft tissue and bone. The white dashed lines show the locations of the x-y and x-z image planes in FIGS. 34A and 34C. FIG. 34C is an x-z plane image from the slice y=2 cm showing the vertical structure of the soft tissue and bone. The white lines show the locations of the x-y and y-z image planes in FIGS. 34A and 34B. FIG. 34D is a 3D representation of the volumetric MRI image.

FIG. 36A is a pulse echo sound speed setup including a potentiometer and single transducer. FIG. 36B is a travel time, or through transmission, setup including two transducers. This setup is used for measuring the bone sound speed.

FIG. 37A is a pulse echo image with no sound speed compensation. FIG. 37B is an image of an initial guess of the sound speed distribution with the geometry defined from a segmentation of the image in FIG. 37A. The greyscale bar is in m/s.

FIG. 38A is an image of the ground truth sound speed map overlaid with the final segmentation of FIG. 37C outlined (in green). FIG. 38B is a graph of the sound speeds of water, soft tissue, bone, and marrow as function of process iteration.

FIG. 39A is a pulse echo image with no sound speed compensation. The greyscale bar is in dB. FIG. 39B is an image of an initial guess of the sound speed distribution with the geometry defined from a segmentation of the image in FIG. 39A. The greyscale bar is in m/s. FIG. 39C is a pulse echo image generated by compensating for the sound speed distribution. FIG. 39D is a sound speed distribution from the final iteration of the process with the geometry defined from segmentation of FIG. 39C. The greyscale bar is in m/s.

FIG. 40A is an MRI image of beef shank 1 overlaid with the final segmentation of FIG. 39C outlined (in green). FIG. 40B is a graph of the sound speeds of water, soft tissue, bone, and marrow as function of process iteration.

FIG. 41A is a pulse echo image with no sound speed compensation. The greyscale bar is in dB. FIG. 41B is an image of an initial guess of the sound speed distribution with the geometry defined from a segmentation of image in FIG. 41A. The greyscale bar is in m/s. FIG. 41C is a pulse echo image generated compensating for the sound speed distribution. FIG. 41A is a sound speed distribution from the final iteration of the process with the geometry defined from segmentation of FIG. 41C. The greyscale bar is in m/s.

FIG. 42A is an MRI image of beef shank 2 overlaid with the final segmentation of FIG. 41C outlined (in green). FIG. 42B is a graph of the sound speeds of water, soft tissue, bone, and marrow as function of process iteration.

FIG. 43A is an image of the sampling. The darker colors indicate more rays traveled through a particular region. The bone region has more rays passing through it than any other region of the domain. This sampling pattern causes artifacts in Tikhonov regularized inversions. FIG. 43B is the sound speed distribution.

FIG. 44A is an image of a simple numerical phantom mimicking a single long bone in water; the bone sound speed is 3450 m/s. The dashed circle indicates location of the source receivers. FIG. 44B is an image of a numerical phantom mimicking a small thigh cross section of a human, the bone sound speed is 3450 m/s. FIG. 44C is a density image of the numerical femur phantom of FIG. 44B. The bone density is 1800 kg/m$^3$. FIG. 44D is an attenuation image of the numerical femur phantom of FIG. 44B.

FIG. 45A is a graph of a level set function Ø and the zero contour in black. FIG. 45B is an indicator function for Ø. The white region defines the bone region. FIG. 46A a time domain waveform and spectrum of the transmittal signal. FIG. 46B is a pulse echo image of the bone phantom. FIG. 46C is an initial sound speed distribution created from the pulse echo image. The bone sound speed is set to 3200 m/s and the lighter gray region to 1540 m/s. FIG. 46D is an image of an inversion result using Full Waveform Inversion (FWI) with a level set (LS) technique. FIG. 46E is an image of the true model. FIG. 46F is an image of percent absolute error between the true and estimated model. The scale is magnified to amplify visibility, the maximum error is 134% along the bone boundary.

FIG. 47A is a time domain waveform and spectrum of the transmit signal. FIG. 47B is a pulse echo image of the bone phantom. FIG. 47C is an initial sound speed distribution created from the pulse echo image. The bone sound speed is set to 3200 m/s and the lighter gray region to 1540 m/s. FIG. 47D is an image of an inversion result using FWI with a level set technique. The greyscale bar does not cover the full sound speed range to highlight soft tissue features. FIG. 47E is an image of the true model. FIG. 47F is an image of percent absolute error between the true and estimated model. The scale is magnified to amplify visibility, the maximum error is 131% along the bone boundary.

FIGS. 48A-48C illustrate results from an inversion of a numerical femur phantom in water. FIG. 48A is an image of an inversion result using conventional source encoding FWI without a level set technique. The greyscale bar does not cover the full sound speed range to highlight soft tissue features. FIG. 48B is an image of percent absolute error between the true and estimated model. The scale is magnified to amplify the error visibility, the maximum error is 114% along the bone boundary. FIG. 48C is a graph of a cross-section of the results from FWI with and without LS regularization compared to the true model. The soft tissue sound speed near the bone is more accurate for FWI with LS regularization as well as the bone boundary location.

FIG. 49A is a source spectrum with the frequency bands employed for the inversion. FIG. 49B is a pulse echo image of a rod. FIG. 49C is a starting model for the inversions. The thin circle is the true rod shape and location. FIG. 49D is an image of the rod showing the rod in the UST system.

FIG. 50A is a sound speed image generated using Global Coherence Norm FWI (GCN-FWI) with Level Set (LS) regularization. The thin circle is the true rod shape and location. FIG. 50B is a sound speed image generated using conventional FWI with observational data subsets (DS-FWI) with LS regularization. The thin circle is the true rod shape and location.

FIG. 51A is a source spectrum with the frequency bands employed for the inversion. FIG. 51B is a Synthetic Aperture Focusing Technique (SAFT) image of the bovine shank. FIG. 51C is a starting model for the inversions. FIG. 51D is an MRI image of the bovine shank slice showing characteristic internal structures of tissue and bone.

FIG. 52A is a sound speed image generated using GCN-FWI with LS regularization. FIG. 52B is a sound speed image generated using DS-FWI with LS regularization. FIG. 52C is a sound speed image generated using Conventional FWI (C-FWI) with LS regularization. FIG. 52D is a sound speed image generated using C-FWI with LS regularization on a 512-by-512 grid. FIG. 52E is a sound speed image generated using C-FWI. The image illustrates minimal change in the bone geometry compared to the other results and initial sound speed image. Streaky artifacts in the soft tissue and water regions are present.

FIG. 53A is a source spectrum with the frequency bands employed for the inversion. FIG. 53B is a SAFT image of the bovine shank. FIG. 53C is a starting model for the inversions. FIG. 53D is an MRI of the second slice of the bovine shank. FIG. 53E is a sound speed image generated using GCN-FWI with LS regularization. FIG. 53F is a sound speed image of the second slice of the bovine shank generated using C-FWI with LS regularization.

DETAILED DESCRIPTION

Figure 1:
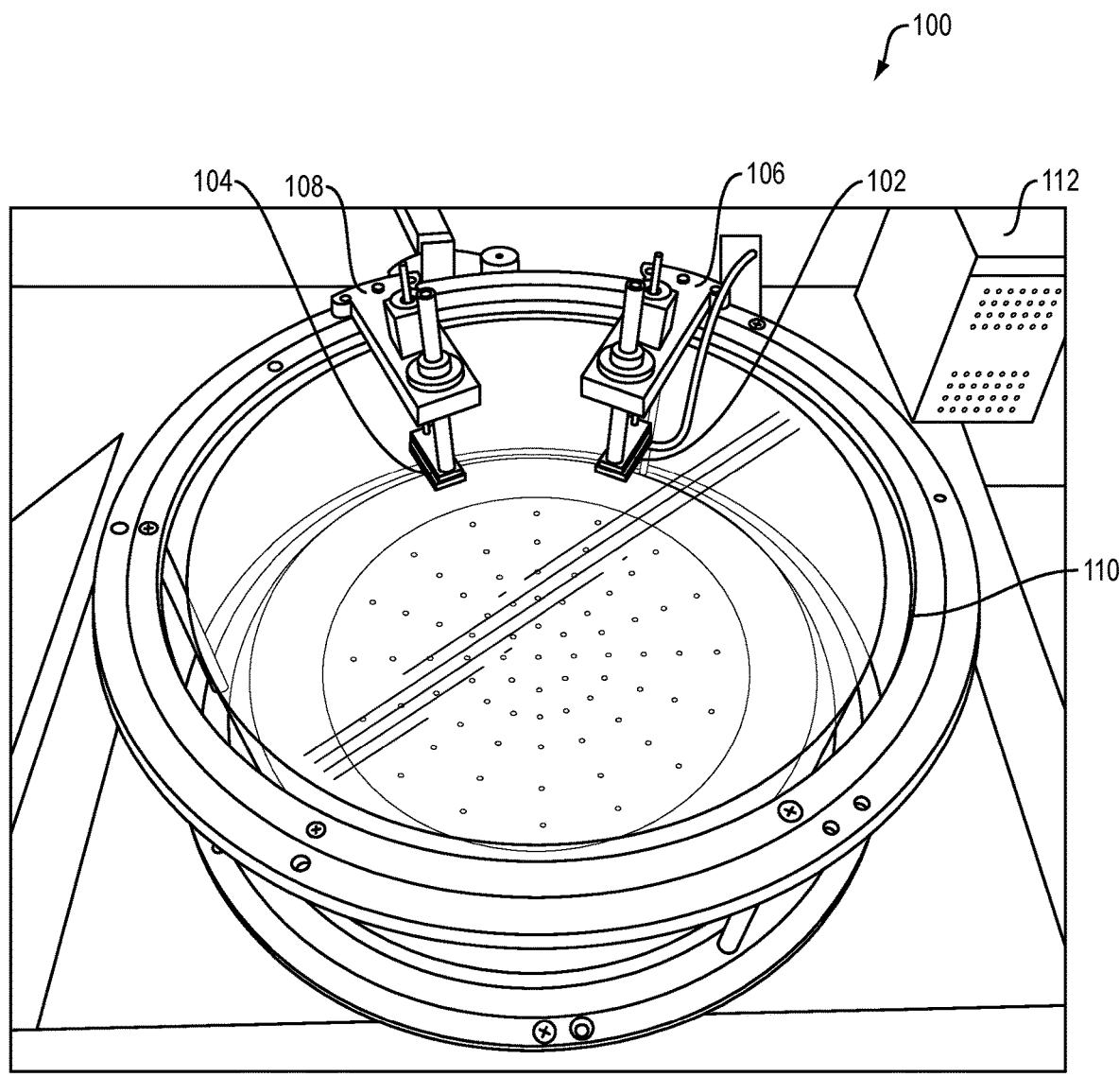
FIG. 1 illustrates an example ultrasound tomography system.

A description of example embodiments follows.

Systems and methods for ultrasound imaging are provided. In the Examples provided herein, non-contact and quantitative ultrasound images are produced from original processes applied to observational data sets collected on two custom built ultrasound imaging systems for limb imaging. The images are quantitative in that the distribution of sound speeds and dimensionally accurate geometry of tissue structures are reconstructed.

Ultrasound can provide advantages over magnetic resonance imaging (MRI) and computed tomography (CT), and there is a need for ultrasound-based, non-contact, quantitative (e.g., geometry, sound speed, attenuation, density, and any combination thereof), large-volume imaging systems and processes for imaging of bone and soft tissue. Development of next-generation ultrasound systems can allow ultrasound to augment or replace CT and MRI for many imaging tasks at a fraction of the cost while providing for increased patient safety, increased patient access to diagnostic imaging, and high-resolution imaging data.

Example non-contact ultrasound imaging systems include ultrasound tomography (UST) systems, such as water-immersion UST systems, and laser generation and detection of ultrasound (LUS) systems. LUS and UST systems and methods can be used, together or separately, to generate large-volume, quantitative two-dimensional (2D) and/or traditional 2D ultrasound images. Existing medical ultrasound systems are unable to acquire and generate large-volume, quantitative, and clinically useful bone images. LUS and UST systems can be clinically valuable by, for example, providing for improved quality, cost, and safety of several applications, such as osteoporosis diagnosis and tracking, prosthetic fitting, bone fracture detection and tracking, intra-operative imaging, and volumetric imaging in intensive care units.

Non-contact imaging techniques are clinically valuable because such techniques can provide for operator-independent image quality and large-volume imagery without contact of the body by system components, which can distort tissue. Current medical imaging processes with ultrasound generally require a sonographer to contact the patient with an ultrasound probe. The contact can deform the tissue being imaged and change the image acquired. Such changes in the image are related to the force applied to the patient by the probe, as well as the angle and position of the probe relative to the patient. Repeatability and generation of large volume image data sets are problematic with contact ultrasound techniques, particularly those involving use of a 2D probe.

To produce a stitched (or composite) volumetric image from mechanical scanning, the probe and patient tissue surface must be tracked (e.g., angle and position tracking) to within a fraction of a millimeter. This requirement stems from most ultrasound probes acquiring 2D images, and, typically, features of clinical interest are ~1 mm. To deliver a repeatable scan, a contact ultrasound system would need to allow for a sonographer to re-scan the patient using the same probe trajectories and force.

Non-contact ultrasound systems can overcome these problems by delivering ultrasound waves to the body without requiring physical contact of the patient. Non-contact ultrasound systems can also provide for volumetric, or three-dimensional (3D), and quantitative imaging, such as by surrounding a portion of the patient with ultrasound transducers, which can provide similar benefits as provided with MRI and CT. Volumetric images can advantageously allow for an entire object or region under investigation to be resolved, rather than a slice of the object or region, as with conventional 2D ultrasound. A full view of the anatomy can be helpful in making clinical decisions.

Quantitative ultrasound imaging techniques are clinically useful because such techniques can provide intrinsic information about tissue mechanical properties, such as stiffness, density, and attenuation. Sound speed is related to tissue stiffness, and density is an intrinsic property of tissue. Mechanical properties of tissue can be directly related to tissue health, such as in breast cancer and liver diseases. Shear wave elastography with 2D probes is becoming a popular quantitative ultrasound imaging technique. Currently, shear wave elastography suffers from significant lack of measurement accuracy due to uncontrolled acquisition states (e.g., probe orientation, force applied by operator, probe placement, etc.) that exist when using a hand-held 2D probes.

Bone imaging with ultrasound is not common clinically. X-ray and MRI technology can provide high-quality bone images. However, ultrasound offers several advantages over x-ray (e.g., CT) and MRI, including reduced cost, increased portability, and, as compared with x-ray, no radiation. Bone is challenging to image and quantify acoustically due to its large impedance contrast (e.g., sound speed and density) with the soft tissue surrounding it. Such contrast can create large reflections off the bone surface, leading to multiple reflections, shadowing of other features, and low signal-to-noise (SNR) inside the bone region. Significant refraction also takes place as acoustic waves pass from soft tissue into bone. Furthermore, conversion of compressional waves into shear waves at the bone surface can further complicate imaging and quantification of bone properties.

Bone and soft tissue quantification using LUS and/or UST systems and methods can provide for non-contact, radiation-free means of assessing bone and soft tissue strength and health. Such systems can be useful in clinical settings where repetitive screening and tissue-property tracking are important. Simultaneous clinical imaging and quantification of hard and soft tissues, such as bone and muscle, in vivo can be applied to several applications, including, for example, improving prosthetic fitting, muscle health monitoring, osteoporosis monitoring, bone fracture detection and imaging of and through the skull.

UST systems can include a water tank and one or more ultrasound transducers mounted at known locations to a perimeter of the water tank. Ultrasound waves generated by the system are acoustically coupled from the transducers into the patient's body via a fluid, such as water, in the tank, enabling non-contact imaging. To obtain an image from a UST system, a patient introduces a part of their body into the water bath, and the device executes an ultrasound wave transmission and reception routine. Fine sampling rates and large apertures of the transducers can enable resolution of the transmitted, reflected, and scattered acoustic field, which contains information about the spatial distribution of the tissue mechanical properties. Quantitative ultrasound images can be produced from the acquired acoustic field data by execution of image reconstruction processes. Volumetric images can be obtained where the transducers are mounted in a 2D or 3D array.

LUS systems include a generation laser and a detection laser. The generation laser can be a pulsed laser that creates a local thermo-elastic source on the surface of the patient's skin, which launches an ultrasonic wave into the tissue. The detection laser can be a laser interferometer (e.g., operated in a pulsed or CW mode), which is focused onto the skin surface (likely near the generation laser spot) and measures the vibrations of the skin surface from ultrasound waves reflected or scattered from tissue structures.

With laser ultrasound techniques, the patient skin surface can be tracked to inform the generation and detection laser spot locations for image generation. Imaging processes with laser ultrasound techniques do not produce large-scale deformations of the patient. Contact with the patient is not required, nor is a water-bath or immersion into another type of fluid, as the two ultrasound waves can be "coupled" electromagnetically to the patient. The lasers can be precisely scanned along the patient to generate 2D or 3D images of the body interior.

Tomographic inversion techniques can be applied to data sets collected from UST systems to generate clinically meaningful images. In addition to UST systems, photoacoustic tomography systems are also able to generate clinically meaningful images and are in development for soft tissue imaging. UST and photoacoustic tomography studies have focused on producing clinically relevant images of breast tissue for breast cancer detection. For breast tissue, modest sound speed and density variations on the order of 50 m/s and 50 kg/m$^3$ are typical. In contrast, large sound speed and density variations (e.g., 1500 m/s and 100 kg/m$^3$ are) occur at bone-soft tissue interfaces, which presents significant additional algorithmic and measurement challenges to produce clinically useful images in parts of the body with bone inclusions.

Studies using ultrasound tomography techniques to image and quantify cortical bone are less common than those pertaining to soft tissue imaging. Techniques relying on path averaged sound speed and attenuation can be used for quantifying cortical and calcaneus bone; however, such techniques typically cannot compensate for bone geometry as well as source and receiver positioning relative to bone.

Improvements in ultrasound imaging and quantification of bone material properties can be made through improved modelling of propagation physics, acquiring larger and more controlled data sets, and constraining inversions with a priori information. Full Waveform Inversion (FWI) methods, when coupled with adequate observational data, can provide for imaging and quantification of bone material properties as FWI methods can handle reflected and transmitted waveforms, as well as strong and specular scattering. FWI ultrasound systems and methods can include ultrasound transducers that surround a volume of interest to provide for the collection of reflected and transmitted acoustic waves to robustly image the human body. Such systems are a departure from traditional linear and convex probes used in conventional ultrasound systems. FWI systems can be water-bath based, with piezoelectric transducer elements for receiving signals and either piezoelectric sources and/or laser sources for sending signals. Alternatively, laser sources and laser receives can be included, without use of a water tank for coupling to the volume of interest.

Experiments completed with an example LUS system (see Examples 1 and 2 herein) demonstrate image generation capabilities without contact or treatment of skin surfaces. Further, soft tissue, which is a weak reflector, as well as bone, which is a strong reflector, are resolved at skin safe optical exposures. To enhance the LUS system performance, the optical wavelength of the generation laser was optimized to deliver a large acoustic source while also meeting optical exposure thresholds for skin. Additionally, laser vibrometer methods are optimized for detecting vibrations on rough surfaces, such as skin.

Experiments completed with an example UST system (see Examples 3-6) and three original processes yielded images of bone and soft tissue geometry and sound speeds when applied to experimental data. One process provides for a backscatter/reflection adaptive imaging technique that enables high resolution, signal to noise ratio (SNR), and volumetric imagery of bone and soft tissue to be formed from a single, mechanically scanned ultrasound transducer. Another process provides for a travel-time sound speed inversion technique that was shown to estimate water, soft tissue, and bone sound speeds to within 10% of ground truth estimates. The performance of this process was validated on multiple samples and a simulated data set. Yet another process provides for a full waveform inversion (FWI) process regularized with a level set technique to enable quantification of bone properties. This process was validated on an animal tissue sample and simulated data sets. The FWI technique was shown to resolve the soft tissue spatial sound speed distribution with half to one-quarter wavelength (1-0.5 mm) resolution, and average sound speed values were shown to be within 10% of ground truth measurements.

Acquisition Hardware

An Ultrasound Tomography (UST) system can include an immersion tank 100, as shown in the example system of FIG. 1. The immersion tank 100 includes a volume 110 configured to contain a fluid, such as water, and to receive a sample to be imaged (not shown). The UST system can include at least one ultrasound transducer configured to emit an ultrasound beam, such as a planar or spherical ultrasound beam, and at least one ultrasound transducer configured to detect reflection and transmission of the ultrasound beam off of a biological body segment disposed in the volume 110. A planar ultrasound beam can be beneficial for constructing planar slices of a biological body segment, and a spherical ultrasound beam can be beneficial for volumetric constructions of a biological body segment. Other geometries can be provided, which may depend on factors such as a type of biological body segment to imaged, a type of tissue to be imaged, and system constraints. The ultrasound beam can be of any known geometry.

As illustrated in FIG. 1, the immersion tank includes two single-element transducers 102, 104 mounted at different radii from a center of the tank and connected to robotic arms 106, 108. The transducers 102,104 can be independently positioned, both angularly and vertically, about a perimeter of the volume 110. Such a configuration can enable multi-aperture data acquisitions over large ultrasonic bandwidths.

While only two transducers are illustrated, a UST system can alternatively include three or more transducers (e.g., 3, 4, 5, 10, 12, 20, or more). The transducers can be moveable with respect to the volume 110, such as by robotic arms 106,

108. Alternatively, the transducers can be fixed (e.g., an array of transducers can be fixedly disposed about the perimeter and/or at varying vertical locations of the volume) or moveable in one or two dimensions (e.g., transducers can be fixed to a ring, which can translate vertically within the volume). An advantage of providing the transducers on robotic arms is that transducers can be independently controlled, which can provide for finer sampling in specific regions of the scan volume, more customized scan patterns, and revisiting of under-sampled regions.

The transducers 102, 104 can be replaceable, which can allow for use of different transducers with varying properties, such as beam width and frequency, to be employed in the system. The UST system can be bistatic, in which a source transducer is separate from a receive transducer.

The UST system can also include a controller 112 configured to cause transmission of an ultrasound signal from a source transducer (e.g., transducer 102) and to receive signals from a receiving transducer (e.g., transducer 104). The controller 112, or a separate processor configured to receive the acquisition data of the system, can be configured to perform image processing, such as with FWI methods, as described below.

Figure 2:
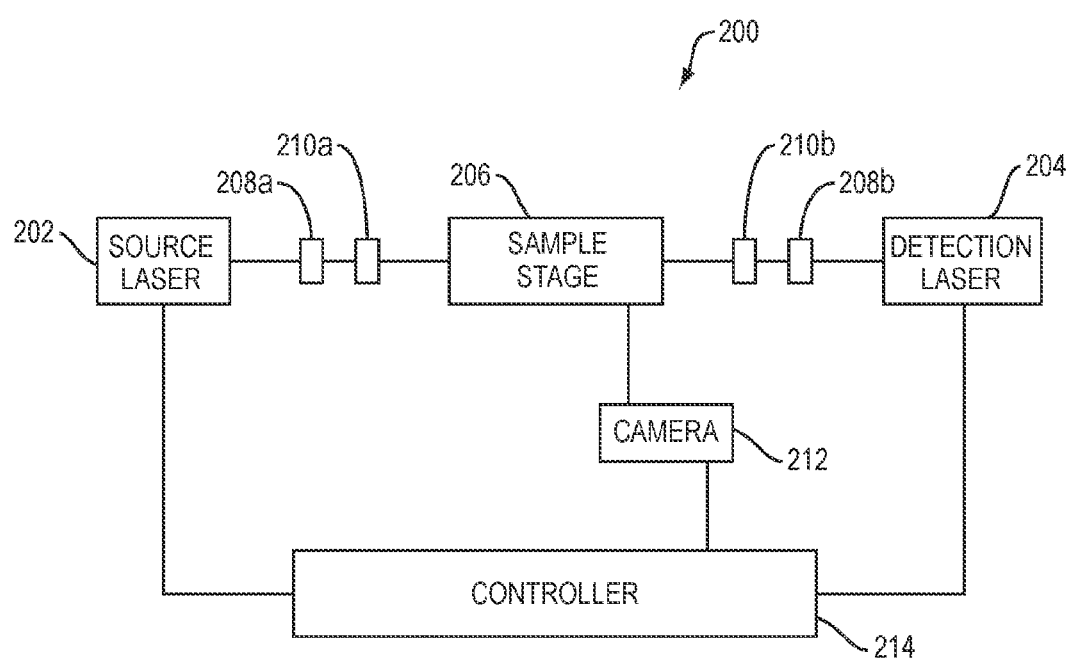
FIG. 2 is a schematic of an example laser ultrasound system.

An example of a schematic of a Laser Ultrasound (LUS) system 200 is shown in FIG. 2. The LUS system 200 can include a source laser 202, a detection laser 204, and a sample stage 206. The sample stage 206 can be moveable in any combination of x-, y-, and z-directions to provide for positioning of a sample to be imaged relative to the source and detection lasers 202, 204. Alternatively, the source and detection lasers 202, 204 may be moveable relative to the sample stage 206.

The source laser 202 can be a pulsed laser configured to generate an ultrasound source signal in a sample, and the detection laser 204 can be a vibrometer or interferometer configured to detect direct or reflected sound waves at a surface of the sample. The source and detection lasers can be configured to operate at eye- and skin-safe levels.

The LUS system 200 can optionally include steering mirrors 208a, 208b and/or shutters 210a, 201b positioned between the lasers 202, 204 and the sample. The shutters 210a, 210b can be configured to reduce a total optical exposure onto the sample. The system 200 can optionally include a camera 212 and alignment lasers (not shown). The camera 212 can provide for measurements of external surface geometry of the sample to be imaged (e.g., a biological body segment).

The LUS system can also include a controller 214 configured to provide and receive signals to and from the source laser 202 and the detection laser 204. The controller 214 can also be configured to provide for translation of sample stage 206 and operation of the steering mirrors 208a, 208b and/or shutters 210a, 201b. The controller 214, or a separate processor configured to receive the acquisition data of the system, can be configured to perform image processing, such as with FWI methods.

In an example, an LUS system includes at least one pulsed laser that excites or generates at least one thermos-elastic wave when directed toward a surface of a biological body segment (e.g., a skin surface). The example LUS system can also include at least one laser vibrometer that detects signals propagated through and/or reflected from internal tissues of the biological body segment. A plurality of steering mirrors can be included and configured to steer the pulsed laser(s). An optical system can be included to measure an external surface geometry of the biological body segment. The pulsed laser can be configured to emit at an optical wavelength of about 1400 nm to about 2000 nm (e.g., from about 1400 nm to about 1550 nm, or from about 1900 nm to about 2000 nm).

UST and LUS systems, such as systems 100 and 200, respectively, can be used independently or in combination.

Imaging Method and System

Figure 54:
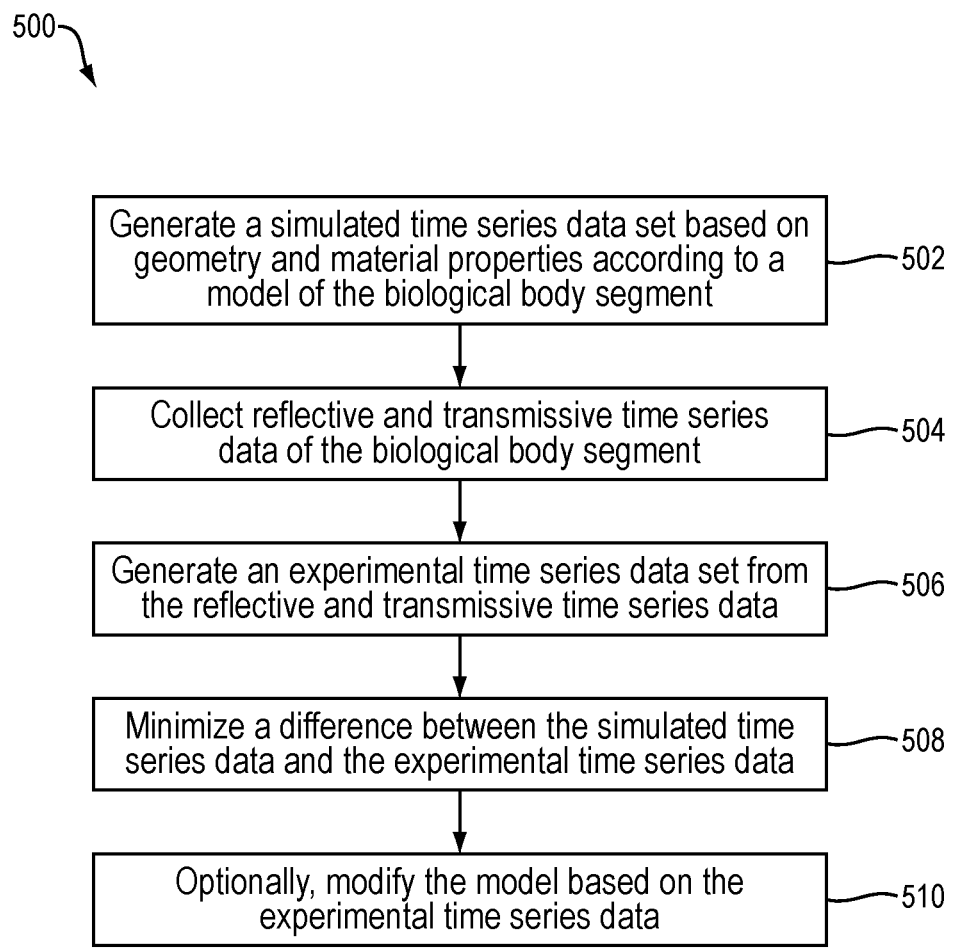
FIG. 54 is a flow chart of a method for imaging a biological body segment of soft and hard tissues.

A method for imaging a biological body segment that comprises soft and hard tissues is shown in FIG. 54. The method 500 includes generating a simulated time series data set based on geometry and material properties according to a model of the biological body segment (step 502). Reflective and transmissive time series data of the biological body segment is collected (step 504). Collection can occur, for example, with UST and/or LUS systems, such as systems 100 and 200. The method 500 further includes generating an experimental time series data set from the collected reflective and transmissive time series data (step 506) and minimizing a difference between the simulated time series data and the experimental time series data (step 508). For example, minimizing a difference between the simulated time series data and the experimental time series data can include any combination of the following: full waveform inversion (FWI), level set region segmentation of a portion or a component of the biological body segment, and regularizing time travel. A tissue boundary detection method can be performed for generation of the simulated time series data.

Optionally, the model of step 502 can be modified based on the experimental time series data (step 510) to more accurate emulate the experimental time series data. Modification of the model can include, for example, applying at least one level set technique. The level set technique can include a full-waveform inversion. Modification can, alternatively or in addition to application of level set techniques, include adding white noise to the simulated dataset to thereby replicate a signal-to-noise ratio of experimental data employed to form the simulated time series data set and/or adding a random position error value to source and receiver positions employed during formation of the simulated time series data set.

The method 500 can be performed by a processor included with a UST and/or LUS system, or by a processor configured to receive reflective and transmissive time series data collected from a UST and/or an LUS system. The UST system can, for example, be configured to emit a planar or spherical ultrasound beam for reflection and transmission at the biological body segment.

Inversion Techniques

FWI techniques have been applied for geophysics imaging of potential oil and gas fields, and for soft tissue imaging in medical ultrasound settings. In some variations of FWI techniques, an adjoint technique is included to calculate a gradient of a misfit function with respect to model parameters. In both geophysics and soft tissue ultrasound applications, methods for reducing the computational cost of FWI have been developed, including source encoding methods. Regularization techniques employing level set methods have been introduced to handle high-acoustic impedance of salt structures in the earth for geophysics applications.

Quantitative images of bone and soft tissue can be generated using FWI with source encoding coupled with level set techniques. In particular, level set techniques can be integrated into source encoding methods for FWI. A priori information about a general structure of bone (e.g. cortical bone) can be included to generate an initial sound speed distribution.

The FWI technique can reconstruct a spatial distribution and value of physical parameters that give rise to experimental ultrasound time series data (e.g., pressure, velocity, and/or displacement). The FWI technique is described below with respect to experimental time series based on numerically generated data with added noise sources. (See also Examples 5 and 6).

The reconstruction transpires by minimizing a difference between an experimental time series and a synthetic time series generated by numerical simulation. The FWI technique typically to minimizes the objective function:

$$E(c, \rho) = \frac{1}{2}\sum_{n=1}^{N} \|u(c, \rho, s_n) - d_n\|^2 \qquad (1)$$

where E is the mean square error between the observed and synthetic data, u is the wave equation operator which outputs a synthetic time series of velocity with units of m/s, $s_n$ is the source for the $n^{th}$ transmission, and $d_n$ is the observed time series data from the $n^{th}$ transmission with units of m/s. The gradient of Eq. 1 with respect to c and $\rho$ can be found in the literature and is given by:

$$\frac{\partial E}{\partial c} = \frac{2}{c^3}\sum_{n=1}^{N}\int_0^T \frac{\partial p_n}{\partial t} p_n^*(t-T)dt \qquad (2)$$

where p is the recorded pressure with units of Pa, p* is the adjoint pressure field, and T is the duration of the observed time series (Bernard et al., "Ultrasonic computed tomography based on full-waveform inversion for bone quantitative imaging," Phys. Med. Biol., 62, 7011-7035 (2017)). Eq. 1 can be re-written to enable the use of a stochastic gradient descent technique, called source encoding, as:

$$E(c, \rho) = \frac{1}{2}\left\|\sum_{n=1}^{N} u(c, \rho, e_n \otimes s_n) - \sum_{n=1}^{N} e_n \otimes d_n\right\|^2 \qquad (3)$$

where $e_n$ is a random encoding sequence, and $\otimes$ is the convolution operator. Here $e_n$ is randomly assigned to be $-1$ or $1$ for each transmission, and $e_n$ changes at each iteration of the gradient descent process, similar to previous studies. The computational burden of FWI typically scales linearly on a number of sources which, for ultrasound tomography, can reach many thousands in number. Source encoding, however, can make the computational cost of FWI independent of the number of sources used in an experiment. The reduction in computational expense can be provided by approximating $\partial E/\partial c$ at each step in the inversion. If enough iterations are run, however, the integrated effect of applying $\partial E/\partial c$ from source encoding yields a nearly identical result as traditional FWI techniques.

The term $\rho$ can take constant binary values of 1050 kg/m³ for soft tissue and 1500 kg/m³ for bone. A regularization term can be added to Eqs. 1 and 3, such as a roughness penalty, however in the method described here, a level set method regularizes Eq. 1.

Figure 45A:
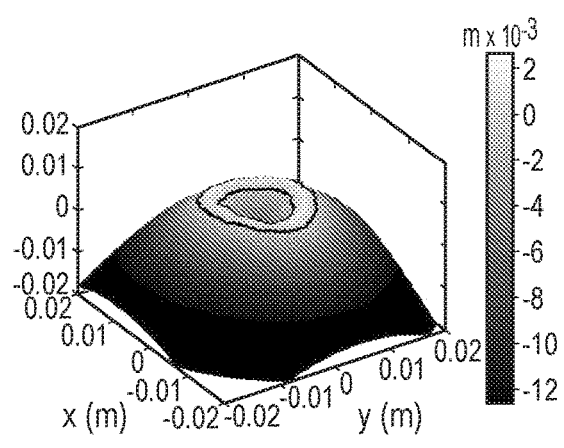
FIGS. 45A-45B illustrate an example of a level set function and associated indicator function.
Figure 45B:
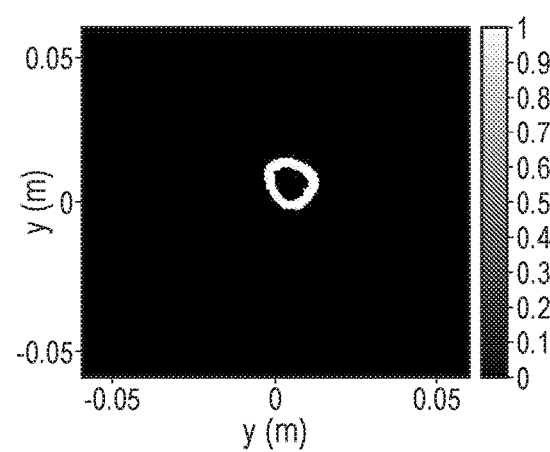

The level set method defines a distance function Ø (an example of which is shown in FIG. 45A) from a contour or contours and allows the contour(s) (and Ø) to evolve as "forces" act on the contours' surfaces. The level set function can define the bone regions and non-bone regions of the domain and can define the c and $\rho$ distributions as follows:

$$c(x,y) = c_{bone}H(\emptyset) + (1-H(\emptyset))c_{soft}(x,y) \qquad (4)$$

$$\rho(x,y) = \rho_{bone}H(\emptyset) + (1-H(\emptyset))\rho_{soft} \qquad (5)$$

where x and y are the spatial coordinates of the domain, and H is the Heaviside function (an example of which is shown in FIG. 45B). Bone properties are given to locations in the domain where Ø≥0, and soft tissue properties are given where Ø<0. The term $c_{soft}(x,y)$ is expressed explicitly as a function of x and y to highlight that its values change from grid point to grid point, in contrast to $c_{bone}$, which takes a single value over entire bone and soft tissue regions defined by Ø.

Using the definition of the sound speed distribution in Eq. 4, a method to evolve the level set function in a way that decreases the error is provided. Based on level set functions described in Kadu, A., and Leeuwen, T. Van, "A Parametric Level-Set Approach for Seismic Full-Waveform Inversion," SEG Tech. Progr. Expand. Abstr. (2016), and Zheglova et al., "Geophysical Journal", Geophyiscs J. Int. (2012), and using a chain rule one arrives at the expression:

$$\frac{\partial E}{\partial \emptyset} = \frac{\partial E}{\partial c}\frac{\partial c}{\partial \emptyset} \qquad (6)$$

to evolve the level set. It can be assumed that the density perfectly correlates with c, such that any changes of Ø with respect to c are also applied to $\rho$. The second term in Eq. 6 is known from Eq. 2, and the third term in the equation is:

$$\frac{\partial c}{\partial \emptyset} = (c_{bone} - c_{soft})\delta(\emptyset(x, y)) \qquad (7)$$

where $\delta$ is the delta function. The presence of $\delta$ can be dealt with by approximating the function. The function:

$$\hat{\delta}[\emptyset(x, y)] = \begin{cases} \frac{1}{2\epsilon}\left(1 + \cos\left(\frac{\pi\emptyset}{\epsilon}\right)\right), & |\emptyset| \leq \epsilon \\ 0, & |\emptyset| > \epsilon \end{cases} \qquad (8)$$

approximates $\delta$ where $\epsilon = 1.5\Delta x$, and $\Delta x$ is the grid spacing of the inversion domain. Regularization of the zero-level set contour takes place by penalizing its' curvature. The curvature, $\kappa$, is given by:

$$\kappa = \nabla \cdot \frac{\nabla \emptyset}{|\nabla \emptyset|}. \qquad (9)$$

The derivatives with respect to distance along the zero-level sets can be estimated in practice and can be spatially smoothed, such as with a 3×3 Gaussian filter.

Level set functions typically call for re-initialization after a few evolutions of the contour to ensure the function remains a distance function. There are many techniques for re-initialization. For example, Ø can be re-calculated after each update by explicitly computing the minimum distance of each pixel in the domain from the zero-level sets.

Generation of Initial Sound Speed and Density Distribution

An initial guess of the bone geometry and sound speed can be provided in a starting model for the FWI process to converge. By applying a synthetic aperture focusing technique (SAFT) to the synthetic data set, a reflection image, like a conventional ultrasound image, can result. A snake process segments an outer boundary of bone in the resulting image, and the inner boundary can be assumed to be 25% smaller than the outer boundary. The inner and outer bone boundary segmentations allow the definition of bone and soft tissue regions in the initial sound speed and density distributions. Inserting literature values for sound speed and density in both regions yields an initial starting model that accounts for the bone geometry and sound speed.

Inversion Methods

In practice, FWI processes invert discrete frequency bands of the experimental data set with increasing central frequency as the number of process iterations increase to avoid cycle skipping. For the examples described herein (see Example 5), the three frequency bands used for the inversion are 20-200 kHz, 200-300 kHz, and 300-500 kHz.

An example method for imaging bone and soft tissue is provided.
i. Create pulse echo image using iso-velocity migration.
ii. Segment pulse echo image for bone region and create the initial sound speed and density maps.
iii. Initialize $\emptyset$ using the segmentation of the bone.
iv. Generate $e_n$ with a random number generator and encode synthetic sources and experimental data.
v. Choose frequency band of data and apply appropriate time domain filters.
vi. Compute $\partial E/\partial c$: take the average of 8 estimates of $\partial E/\partial c$ (parallelize over 8 cores).
vii. Compute $\partial c/\partial \emptyset$.
viii. Update bone geometry by evolving $\emptyset$ using:

$$\emptyset = \emptyset - \mu_\emptyset \frac{\partial E}{\partial c}\frac{\partial c}{\partial \emptyset} - \mu_\kappa \kappa \tag{10}$$

where $\mu_\emptyset$ and $\mu_\kappa$ are scalar weighting factors.
ix. Re-initialize $\emptyset$.
x. Update $c_{bone}$ using:

$$c_{bone} = c_{bone} - \mu_{bone} \int\int \frac{\partial E}{\partial c} H(\emptyset) dx dy \tag{11}$$

where $\mu_{bone}$ is a scalar weighting factor.
xi. Update $c_{soft}$ for $\emptyset<0$ using:

$$c_{soft}(x, y) = c_{soft}(x, y) - \mu_{soft}\frac{\partial E}{\partial c} \tag{12}$$

where $\mu_{soft}$ is a scalar weighting factor.
xii. Return to step (iv) or terminate inversion.

Additional FWI methods are further described in Examples 5 and 6 herein.

Echo Flow Methods

A computationally efficient Adaptive Beamforming (ABF) technique for imaging bone and soft tissue that includes reflected-wave Direction of Arrival (DOA) at a transducer surface to reduce sidelobe interference is provided. The method is referred to as Echo Flow (EF). The EF method can further include a Coherence Factor (CF) weighting to produce a final image.

Figure 21:
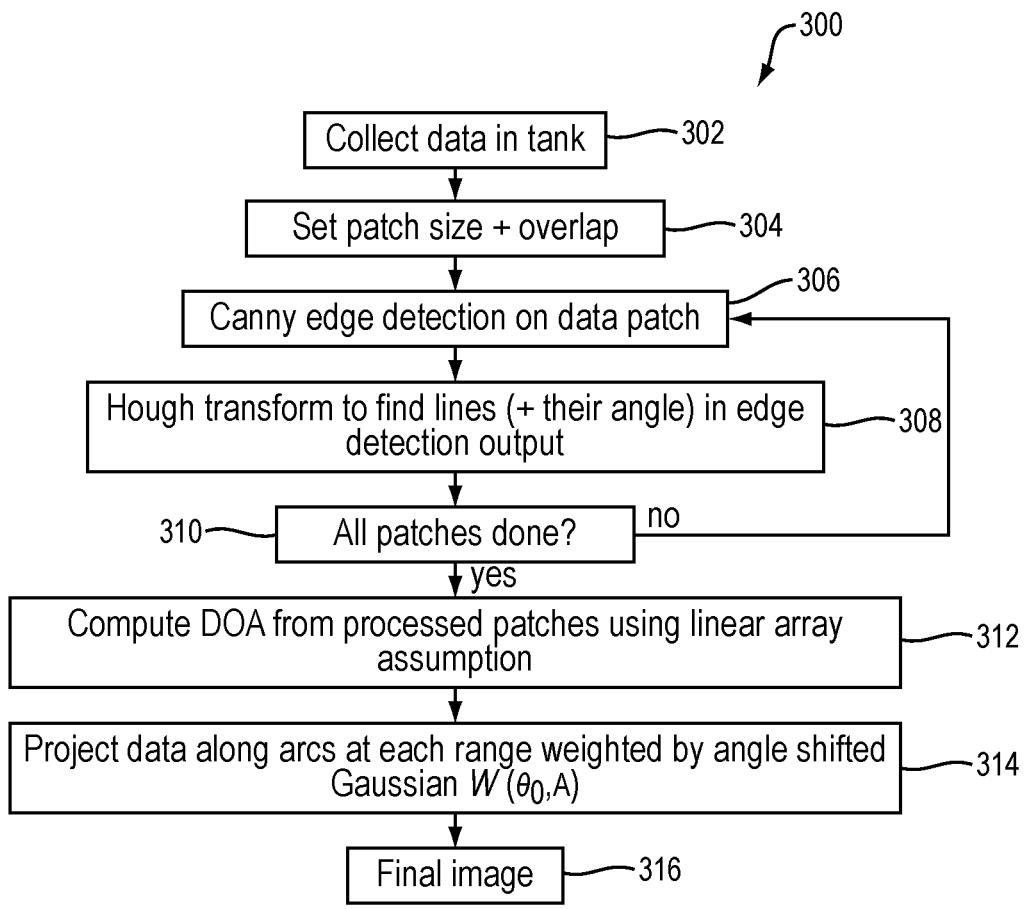
FIG. 21 is a flow chart of a method for synthetic aperture imaging with adaptive beamforming (ABF) for ultrasound computed tomography (USCT) applications.

EF methods are further described in Example 3 herein. An overview of an EF method is shown in FIG. 21. The method 300 can include the following steps: perform data acquisition (step 302); set a patch size and overlap (step 304); perform Canny edge detection on the data patch (step 306); perform a Hough transform to find lines and respective angles in the edge detection output (step 308); repeat steps 306-306 for additional patches until all patches are complete (step 310); compute DOA from the processed patches using a linear array assumption (step 312); project data along arcs at each range, weighted by an angle shifted Gaussian filter (step 314); generate a final image (step 316).

Methods for Estimating Bone and Soft Tissue Sound Speeds

Figure 35:
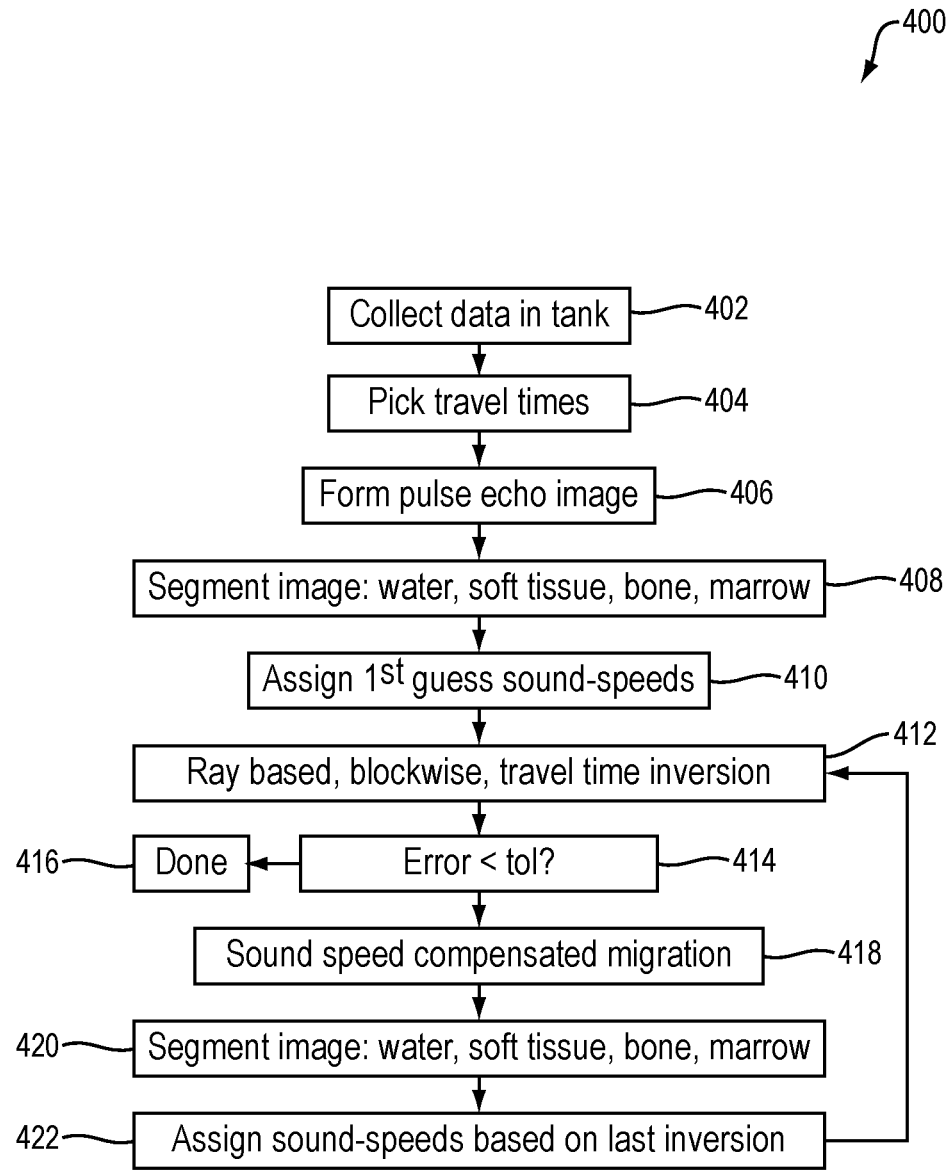
FIG. 35 is a flowchart of a method for estimating sound speeds of bone and soft tissue.

Methods for estimating sound speeds of bone and soft tissue are further described in Example 4 herein. An overview of an estimation method is shown in FIG. 35. The method 400 can include the following steps: perform data acquisition (step 402); select travel times (step 404); form a pulse echo image (step 406); perform segmentation (e.g., segment water, soft tissue, bone, and/or marrow) (step 408); assign an initial sound speed for each segmentation (step 410); perform ray-based, block-wise, time-travel inversion (step 412); determine error (step 414) and discontinue procedure if error is acceptable (step 416); perform sound-speed-compensated migration (step 418); perform re-segmentation (step 420); assign an updated sound speed for each re-segmentation (step 422); and, repeat steps 412-414.

EXEMPLIFICATION

Example 1. Characterization of Laser Ultrasound Source Signals in Biological Tissues Short optical pulses emitted from a tunable Q-switched laser (800 nm-2000 nm) generate laser ultrasound (LUS) signals at the surface of biological tissue. The LUS signal's acoustic frequency content, dependence on sample type, and optical wavelength are observed in the far field, yielding a reference data set for the design of non-contact LUS imaging systems. Measurements show the majority of LUS signal energy in biological tissues is within the 0.5 MHz and 3 MHz frequency band, and the total acoustic energy generated increases with the optical absorption coefficient of water, which governs tissue optical absorption in the infrared range. The experimental results also link tissue surface roughness and acoustic attenuation with limited LUS signal bandwidth. Images constructed using 810 nm, 1064 nm, 1550 nm, and 2000 nm generation laser wavelengths and a contact, piezoelectric transducer as a receiver demonstrate the impact of the generation laser wavelength on image quality. A non-contact LUS-based medical imaging system can be a general-use medical imaging device. Such a system may mitigate inter-operator variability associated with current medical ultrasound imaging techniques and expand the scope of imaging applications for ultrasound.

Potential applications for non-contact LUS in the medical setting include general clinical imaging; monitoring of bone, muscle, and organ health; needle guidance; inter-operative imaging; and cancer detection and screening.

Conceptually, non-contact LUS is similar to conventional ultrasound, except the piezoelectric source/receiver and the coupling agent are replaced with a generation laser (for ultrasound wave generation) and a detection laser (for ultrasound wave detection). The generation laser is a pulsed laser that generates a propagating thermo-elastic acoustic (compressional) and/or shear wave at the surface of a sample via the optoacoustic effect, referred to here as the LUS source. The detection laser is a pulsed or continuous wave Doppler vibrometer that records direct or reflected sound waves (sensitive to sound speed and density distribution within the sample) at the surface of the sample. Detection and generation of the acoustic waves occurs optically, without contact, at a distance and without treatment or immersion of the sample surface. Reflection images from these systems reveal quantities related to the gradient of the sound speed and density distribution (pulse-echo reconstruction), or the sound speed and density distribution itself (tomographic reconstruction), within the sample to centimeter depths.

LUS is similar to non-contact photoacoustic (PA) techniques in that both can employ pulsed lasers and laser Doppler interferometers; however, the two techniques image different physical properties within the medium. PA methods principally image optically absorptive structures within the sample volume, and LUS images sound speed and density inhomogeneity in the sample volume. PA systems are often built to image the vasculature (blood has a high optical absorption coefficient) within a small animal or near the surface of the skin. The blood absorbs the light, undergoes a thermo-elastic expansion, and launches an acoustic wave towards the surface of the tissue where it can be detected and used for image generation. Typically, PA systems use wavelengths ranging from 850 nm 1064 nm to get light to penetrate as deeply as possible into the tissue (enabling images with larger depths). In LUS, larger wavelengths (e.g., 1400-2000 nm) are used to cause as much light as possible to be absorbed at the surface for creation of an acoustic source.

This study further characterizes optical source interaction with biological tissue over a range of optical wavelengths and tissue types. As source amplitude and bandwidth constrain resolution and penetration depth of the imaging system, characterization of LUS source signals generated in biological tissues in the far field can inform design of LUS imaging systems.

The results of the study serve two purposes. First, the results function as a reference data set in the design process of non-contact LUS imaging systems for biological tissue. Second, the results provide further experimental support for using analytical LUS source theory, derived assuming a pure water medium, over a broad range of optical wavelengths and tissue types to predict LUS source characteristics in the far field.

The experiments employ a LUS generation laser to excite an ultrasound source at the surface of beef, pork, and chicken tissue samples while measuring the acoustic signal at the opposite surface of the tissue with a contact piezoelectric acoustic transducer. The observational data set consists of time-domain trace signals. Spectra and acoustic signal energy are calculated for all tissues, over optical wavelengths from 800-2000 nm at 50 nm increments. Comparison of measured time domain signals, spectra, and signal energy to theoretical pure water models shows agreement between biological tissue experimental data and pure water models. Lastly, images constructed using 810 nm, 1064 nm, 1550 nm, and 2000 nm generation laser wavelengths reveal the impact of the generation laser wavelength on pulse echo ultrasound image quality.

Methods

The physical mechanism for generating a LUS signal is summarized as follows: (1) a short duration laser pulse impinges on an optically absorptive surface of a material, such as water or biological tissue; (2) the optical energy rapidly and locally converts into localized heat at the laser spot location; (3) nearly instantaneous expansion of the material due to the localized heating creates a concentration of mechanical stress within the irradiated material; and (4) this stress imbalance dissipates via the propagation of an acoustic pulse from the irradiated region into the material volume. The propagating acoustic pulse is the laser induced ultrasound wave, the LUS source, which can be utilized for imaging. For this process to occur as described, optical, thermal, and acoustic conditions are met by the material and laser pulse. Absorption of optical energy at the sample surface, relative to optical transmission into the tissue, is an LUS condiction. Generation of the acoustic source at the surface is what differentiates LUS from PA techniques.

This optical condition is described by the characteristic optical penetration depth of light into the material, defined by 1, with units of m. (See FIG. 3A, inset.) The optical intensity, with units of W/m$^2$, of incident light as a function of depth into an absorptive and scattering medium is described by $$U = U_0 e^{-z(\mu_s + \mu_a)} \quad (13)$$

where $U_0$ is the incident intensity at the surface, z is the penetration depth into the tissue, $\mu_\alpha$ and $\mu_s$ are the optical absorption and scattering coefficients in the medium, respectively, with units of (m$^{-1}$). The characteristic depth an optical beam will penetrate a medium is $1 = (\mu_s + \mu_\alpha) - 1$ and, for biological tissue at wavelengths greater than 1400 nm, this depth is 1 mm, which is on the order of an acoustic wavelength used for medical ultrasound imaging. The small optical penetration depth compared to typical imaging depths of 5-10 cm allows the assumption that the acoustic source is located at the surface of the material.

The thermal condition is the rate of thermal conduction within the material compared to heating time. By analyzing the diffusive terms in the heat equation, one arrives at the relationship:

$$\tau \ll l_{min}^2 \rho C_p / \kappa \quad (14)$$

where $\rho$ is the material density with units kg/m$^3$, $C_p$ is the medium specific heat with units J/kg-K, $\kappa$ is the thermal conductivity with units W/m-K, and $\tau$ is the laser pulse length in units of s and $l_{min}$ is the smaller of 1 or a, where a is the laser beam diameter with units of m. (See FIG. 3A, inset.) This condition requires the heating time to be much shorter than the time for heat to conduct away from the heating zone in the material and allows for the assumption of instantaneous heating. The instantaneous heating gives rise to local expansion of the material and can call for the localized stress or acoustic (source) condition.

The acoustic source condition can require what is often called "stress confinement." Physically, this condition means that the mechanical energy generated by the thermal expansion of the material cannot propagate away quicker than the rate of energy delivery. This condition can require:

$$\tau \ll \frac{l}{c} \quad (15)$$

$$\tau \ll \frac{a}{c} \quad (16)$$

where c is the speed of sound in that material in m/s. In the context of LUS, Eq. 16 requires the spot diameter and optical penetration depth to be sufficiently large to achieve these conditions.

When the conditions are met, an LUS acoustic source can be efficiently generated in biological tissue. For biological tissues, with a sufficiently large laser spot diameter (e.g., 2 mm), all three conditions are met for optical wavelengths from 800 nm-2000 nm.

Theoretical models for an LUS wave in pure water with a smooth surface show that the frequency domain expression for the waveform is given by the following:

$$P_s(\omega) = \frac{iU_a\beta\mu_a}{2C_p} \frac{e^{ikR}}{R} \frac{a^2 k\cos(\theta)}{\mu_a^2 + k^2\cos^2(\theta)} \exp\left(-\frac{a^2 k^2 \sin(\theta)}{4}\right) \quad (17)$$

where $\omega$ is the radian frequency in (rad/s), i is the imaginary unit, R is the range from the source to the target, $\beta$ is the coefficient of thermal expansion in ($K^{-1}$), $\theta$ is the angle from the source to the target, and k is the acoustic wave number defined as $k=\pi/\lambda$ where $\lambda$ is the acoustic. wavelength (note: $k=\omega/c$). The inverse Fourier transform of Eq. 17 yields the time domain signal. The expression ($\mu_a$ k cos($\theta$)) ($\mu_a^2+k^2 \cos^2(\theta)$) in Eq. 17 is an optical to acoustic conversion efficiency factor scaling the amplitude of the source signal as a function of acoustic frequency. Thus, the optical absorption can significantly impact the resultant acoustic frequency response. The average frequency domain expression for the LUS waveform generated on a rough surface with a Gaussian distribution of roughness heights is given by:

$$\langle P_r(\omega)\rangle = P_s(\omega)\exp\left(-\frac{\sigma^2 k^2 \cos^2(\theta)}{2}\right) \quad (18)$$

where a is the mean square height of the roughness with units of m. The signal decays with increasing frequency scaled by cr. The impact of roughness can be significant. For example, for optical and acoustic parameters typical of biological tissue, a surface roughness with a=0.001 m results in a 5 dB reduction in the source amplitude at 2.5 MHz compared to a smooth surface.

Acoustic attenuation, a, is also important when using LUS to image biological tissue. Acoustic attenuation is due to heating and scattering within the tissue. In human tissue, a=0.5-2 (dB/cal-MHz) and, in beef, values of 2-3 (dB/cm-MHz) have been reported. Acoustic absorption impacts the depth and frequency dependent amplitude, A, of an acoustic wave exponentially as given by:

$$A(z, \omega) = A_o 10^{-\frac{az\omega}{40\pi}} \quad (19)$$

where $A_o$ is the initial pressure amplitude, with units of Pa. Acoustic attenuation, with respect to imaging, severely decreases the amplitude of high-frequency signals and therefore limits spatial resolution. Since image resolution is dependent on the inverse bandwidth of the transmit signal, attenuation can set an upper limit of image resolution and maximum imaging depth due to finite signal to noise ratio of imaging systems.

Experimental Setup

Figure 3A:
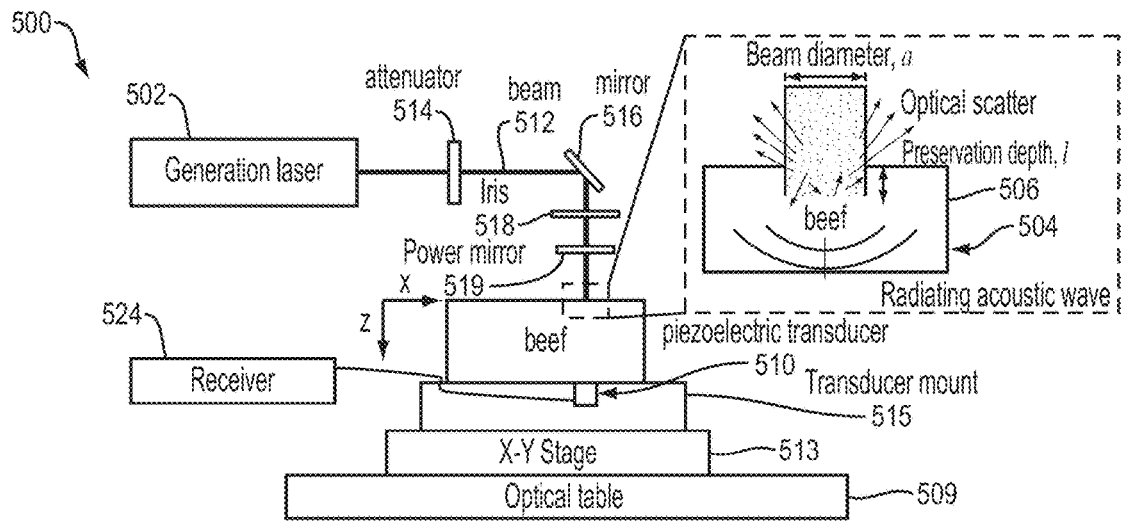
FIGS. 3A-3C are schematics of three experimental setups.
Figure 3B:
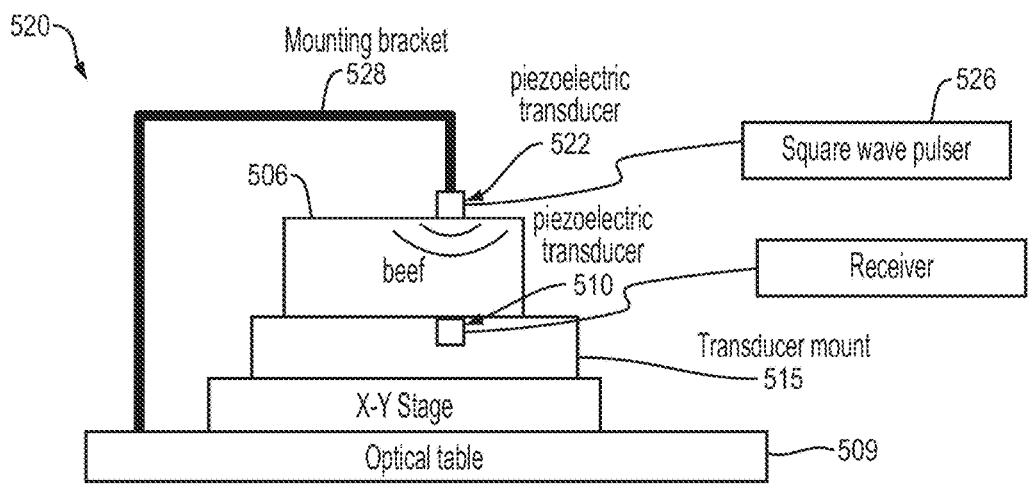
Figure 3C:
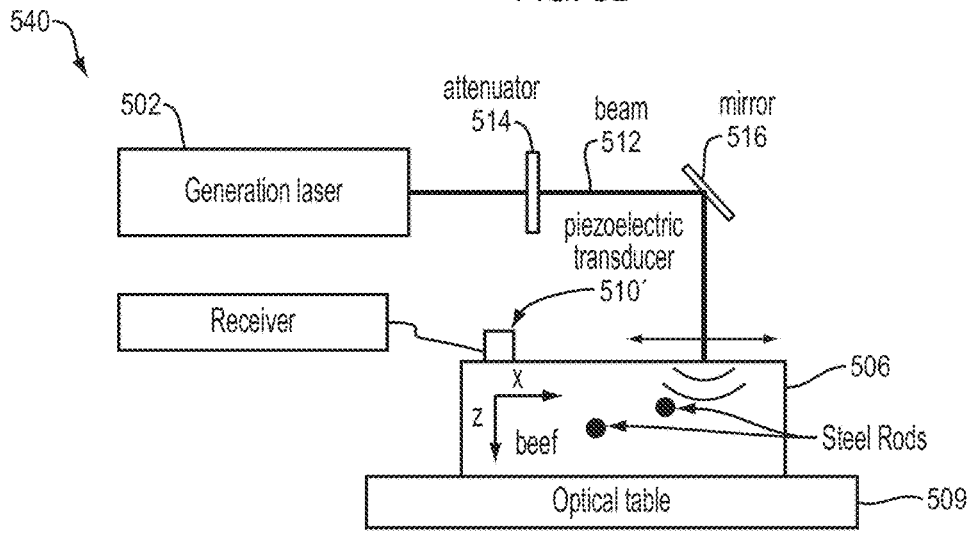

Three hardware configurations are utilized for the experiments, schematics are shown in FIGS. 3A-3C. The first configuration 500, shown in FIG. 3A, uses an LUS generation laser 502 for exciting an acoustic wave 504 at the surface of the sample 506, and the second configuration 520 shown in FIG. 3B uses a piezoelectric transducer 522 to generate an acoustic wave at the surface of the sample. The second configuration is employed to isolate the impact of tissue surface roughness for comparison to data from the first configuration. The third setup 540 is a pulse echo imaging setup FIG. 3C that includes an LUS generation laser 502 to excite an LUS source at the surface of a sample 506 and a contact piezoelectric transducer 510' to receive the reflected and direct arrivals from the LUS source.

The first experimental setup uses a generation laser 502 to excite ultrasonic waves in the tissue sample. The generation laser used is a tunable optical parametric oscillator (OPO) laser (30 pulses/sec, 9 ns pulses, Continuum, San Jose, Ca, USA), operating at discrete optical wavelengths from 800 nm to 2000 nm, stepped in 50 nm increments. The beam 512 from the laser passes through an adjustable attenuator 514 to a mirror 516, which directs the beam through a 3 mm iris 518 and then onto the sample 506. Beneath the iris is a removable power meter 519 to measure the optical power reaching the sample (FIG. 3A). The tissue sample lays underneath the iris 518 on the transducer mounting-bracket 515, which is mounted on an x-y stage 513 rigidly secured to an optical table 509. The x-y stage 513 enables centering of the laser spot above the piezoelectric acoustic receiving transducer 510 (Olympus V1091, Olympus, Tokyo, Japan). The transducer mount 515 serves as a rigid mount for the transducer, and ultrasound transmission gel (Aquasonic® 100, Parker, Fairfield, NJ, USA) couples the transducer 510 to the tissue sample 506. The transducer used has a 5 MHz center frequency and a usable bandwidth between 0.5 and 8.0 MHz. The piezoelectric, disk-shaped element in the transducer is 3.0 mm in diameter, yielding a far field distance of ~3 cm=$a^2/\lambda$ at 5 MHz. After the waveform passes through a receiver 524 (Olympus 5077 PR pulser-receiver with a 50 dB gain and a 10 MHz low-pass filter), a 200 MHz oscilloscope (Tektronix, Beaverton, OR, USA) digitizes the waveform for collection.

The second setup 520 uses two of the same Olympus V1091 piezoelectric transducers 510, 522 previously mentioned. A BNC cable electrically connects the source transducer 522 to a pulser 526 (an Olympus 5077 PR pulser-receiver), and an adjustable bracket 528 mounted to the optical table 509 serves as a rigid mount for the source transducer 522. The pulser-receiver 526 generates a one-and-a-half cycle square wave with 0.7 µs duration peaks. The source transducer 522 is centered above the receiving transducer 510 and lightly contacted with the tissue sample 506 using the adjustable mounting bracket 528. Ultrasound gel couples the source and receive transducers 510, 522 to the sample. The waveform acquisition setup and receiving transducer configuration is identical to the first setup.

Three sample types are tested: beef, chicken, and pork bought from the butcher and approved for use under Massachusetts Institute of Technology Committee on Animal Care protocol number E17-09-0320 for use of animal tissue. All tissue samples are at least 3.5 cm in height such that all data with frequency content less than 5 MHz is in the far field of both the transducer and LUS source. The beef sample contains only muscle and fat, while the chicken and pork samples both have skin at the surface with muscle and fat tissue underneath.

The data collection process using the first setup starts by centering the laser spot above the transducer. Next, the generation laser wavelength is manually swept from 800 nm to 2000 nm at 50 nm increments. Across the spectrum of wavelengths, the laser power is kept at 7.5 mW with a spot area of 0.071 cm² (3 mm diameter), yielding a fluence of 3.54 mJ/cm² per pulse, which is skin and eye safe at optical wavelengths between 1500 nm and 1800 nm, with a safety factor just under 10 (30 Hz pulse frequency). The laser power at the samples remains constant by checking the power meter after changing the laser wavelength and correcting the attenuator as needed to maintain constant power. At each optical wavelength, the acoustic source signal generated by the laser pulse is saved on the oscilloscope for post processing, resulting in 25 waveforms for each tissue sample tested. Signals with insufficient signal to noise ratio (SNR) are omitted from the data set. Signals with low noise are considered any signal in which the LUS signal waveform is not easily identified by eye.

The data collection process using the second setup starts by centering the source transducer above the receiving transducer. Next, an acoustic pulse propagates from the source transducer through the tissue to the receiving transducer. An oscilloscope attached to the receiving transducer digitizes the incident acoustic waveform on the receiving transducer, and the resulting data is saved for post processing. Only data on beef samples is collected using the second setup due to logistical constraints.

The third setup (FIG. 3C), referred to from here on as the imaging setup, uses the same hardware as the first setup, except the iris 518 is removed to allow scanning of the generation laser spot (illustrated with horizontal arrow).

The beam diameter at the surface of the sample 506 is 2 mm and the pulse energy is 0.8 mJ, yielding skin safe optical exposure levels from 810 nm to 2000 nm. The transducer position is on the sample's top surface, as is the generation laser spot. The data acquisition setup is identical to the first setup. The sample under test is beef purchased from the butcher with two small metal wires inserted into it.

The data collection process using the imaging setup consists of scanning the generation laser 502 a distance of 5.4 cm in the x direction in 0.54 mm discrete steps along the sample surface starting 0.5 cm from the transducer 510' (FIG. 3C). At each of the 101 scan locations, the generation laser excites an ultrasound source and the transducer, which remains fixed for the scan, records the direct and reflected wave arrivals. Four scans using generation laser wavelengths of 810 nm, 1064 nm, 1550 nm, and 2000 nm comprise the data set from the imaging setup. The analog gain on the transducer remains constant across all scans. A bi-static migration process is used to generate an ultrasound image from each scan, yielding four images from four different generation laser wavelengths on the same target.

Results—Waveforms and Spectra

Figure 10A:
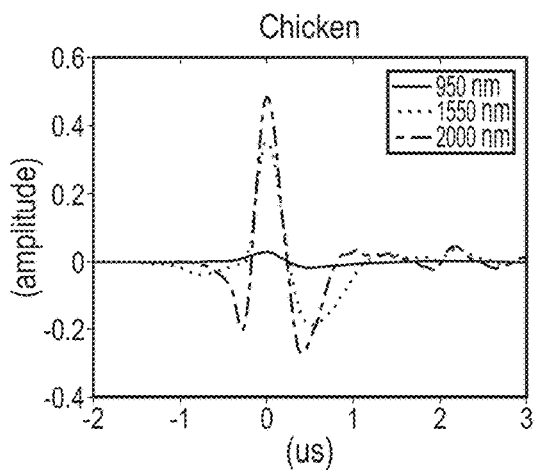
FIGS. 10A-10D are graphs of acoustic waveforms and spectra representative of data sets for chicken and pork samples.
Figure 10B:
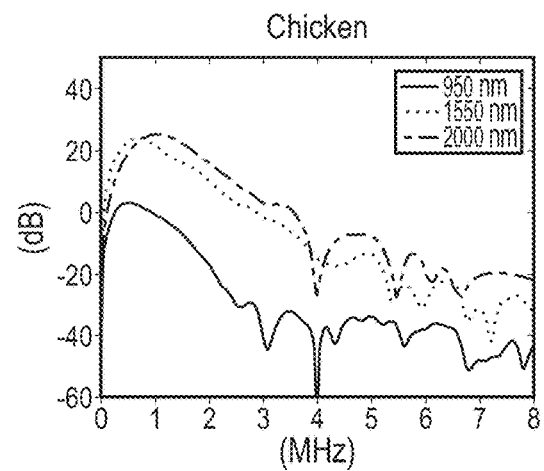
Figure 10C:
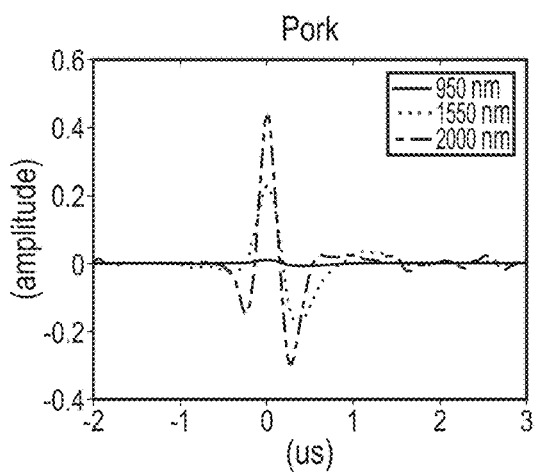
Figure 10D:
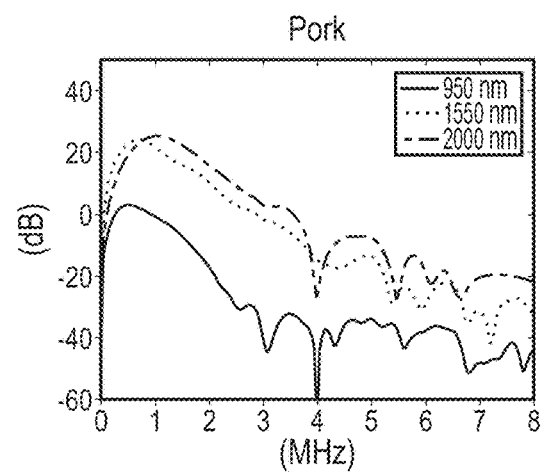

The laser-generated ultrasound signals in the beef, measured with experimental setup one, exhibit a similar form to laser-generated ultrasound signals observed in water (FIG. 4A). The data in FIG. 4A is from the beef samples, data for the pork and chicken are similar and are shown in FIGS. 10A and 10C. The spectra of the signals exhibit a peak near 1 MHz, and a steady decay in amplitude until the noise floor of the data is reached, near 3.5 MHz, depending on the optical wavelength used (FIG. 4B). The decay in the spectral amplitude with frequency is not due to the transducer response, which is shown by the dashed line in FIG. 4B, but is likely due to acoustic attenuation and surface roughness. The downward slope of the spectra after the 1 MHz peak is roughly twice the expected value for acoustic power law absorption for beef of −2.9 (dB/(cm-MHz)). There is also energy that arrives after the first peak in the time domain signals, which suggests multiple scattering along the propagation path. It is also possible that scattering off the rough sample surfaces is accounting for the late arrival of energy since the source is a pressure distribution. This means the initial wave propagates in all directions, and therefore some of the initial acoustic pulse reflects and scatters off the surface of the sample.

The waveforms of the pork and chicken spectra are similar to those for beef A skin layer is present on both the chicken and the pork samples, yet the presence of the skin does not appear to alter the source waveform characteristics compared to the beef sample. Results for pork and chicken samples are shown in FIGS. 10A-10D.

The SNR of the waveforms collected from the chicken sample at the optical wavelengths of 800 μm and 850 μm is sufficiently low that the waveforms are excluded from the results. Waveforms from the pork sample at optical wavelengths of 800, 850, 900, and 950 nm are also excluded for the same reason. None of the waveforms collected on the beef sample are excluded from the results.

In FIG. 5A, an LUS source signal generated with a 1550 nm pulse in a beef sample (solid gray line) is compared to data from setup two (thick black line), also from the beef sample, and theoretical predictions (thin black line, dashed line). The theoretical prediction (thin black line) for the LUS source waveform using Eq. 18 is corrected for both acoustic attenuation and transducer response and shows good agreement with the observed laser-generated ultrasound source signal (gray line) (FIGS. 5A-B). Since the acoustic data is not calibrated, Eq. 18 is arbitrarily shifted vertically to compare with the observed data. The parameters put into the theoretical prediction are $\mu_a=730$ m$^{-1}$, $\sigma=3.4\times10^{-4}$ m, and a=−2.9 dB/cm-MHz. The value for a is the value that minimizes the mean square error between the model Eq. 18 and the data over the 0.5-2 MHz spectral band. The values for a and a are taken from the literature. The spectra of the time domain signals from FIG. 5A are shown in FIG. 5B. Both spectra are sloping downward, as expected. The slope of the spectra from setup one is significantly greater than the downward slope from setup two, likely due to surface roughness of the sample. The nulls in the spectra from setup two at 2.75 MHz and 5.75 MHz are a result of the frequency response of a square pulse. waveform.

The main source of difference between the spectra from the two setups is the method employed (laser vs. piezo electric transducer) for generating the acoustic wave in the sample (i.e., the data is collected on the same sample along the same acoustic path using the same receiver). This comparison is not shown for other tissues because reliable estimates of a for other tissues are not available in the literature.

The dashed lines in FIGS. 5A-B are the theoretical prediction for a LUS source waveform generated on a smooth pure-water surface corrected only for the receiving transducer frequency response. The experimental results are wider in the time domain (FIG. 5A) and narrower in the spectral domain (FIG. 5B) (gray line) compared to-the theoretical predictions for pure water. This is due to surface roughness and attenuation that affect LUS source waveforms in biological tissues. Data collected on water, not shown, is similar to the theoretical curves, with high SNP' from 1 MHZ up to 9 MHz as well as a narrow pulse. The experimental results from the beef samples in agree with the theoretical curves shown that are corrected for surface roughness and acoustic attenuation. This agreement supports the hypothesis that acoustic attenuation and surface roughness play a significant role determining the LUS source characteristics.

Results—Signal Power as a Function of Absorption

Figure 6A:
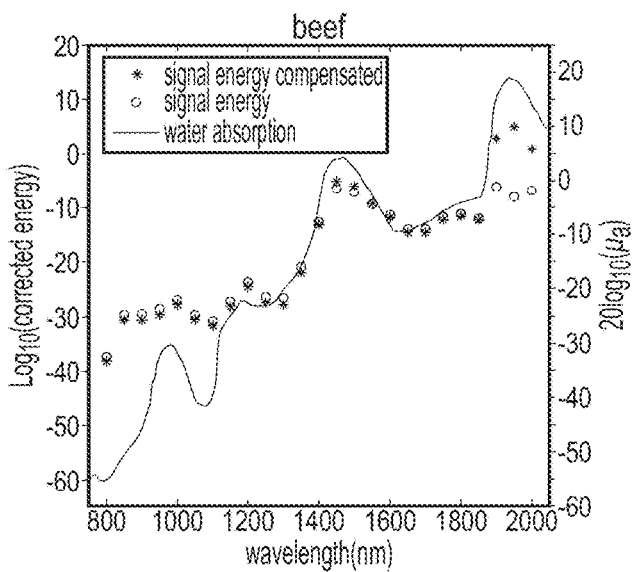
FIGS. 6A-6C are graphs illustrating dependence of signal energy (corrected and uncorrected) as a function of optical wavelength as compared to optical absorption (pa) of water for beef, chicken, and pork samples.
Figure 6B:
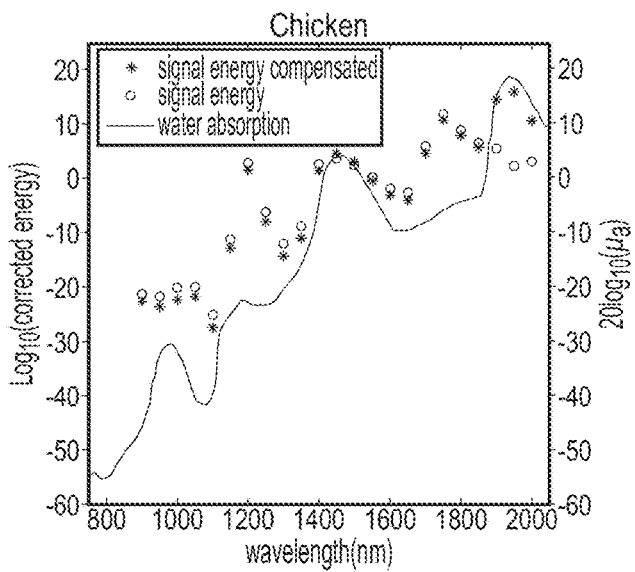
Figure 6C:
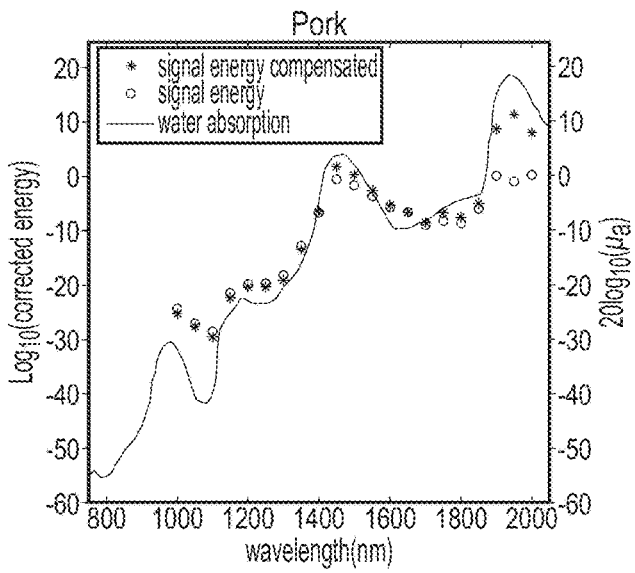
Figure 7A:
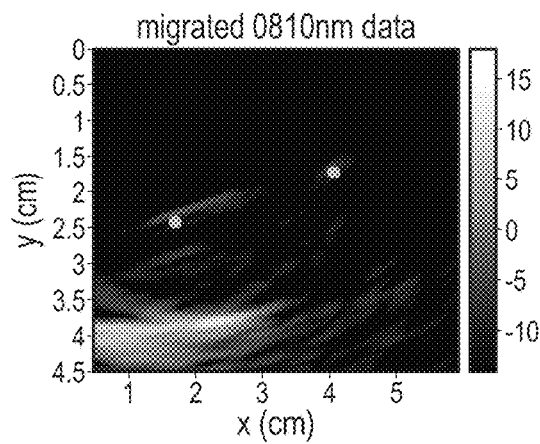
FIGS. 7A-7D are images acquired using an experimental setup and illustrate a dependence of image quality on generation laser wavelength. All images are shown on a 32 dB dynamic range and are acquired on the same sample at the same location using identical fluences. The green dots indicate the approximate locations of the metal wires in the images.
Figure 7B:
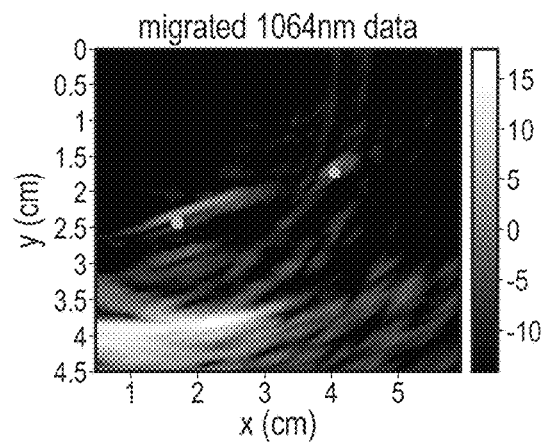
Figure 7C:
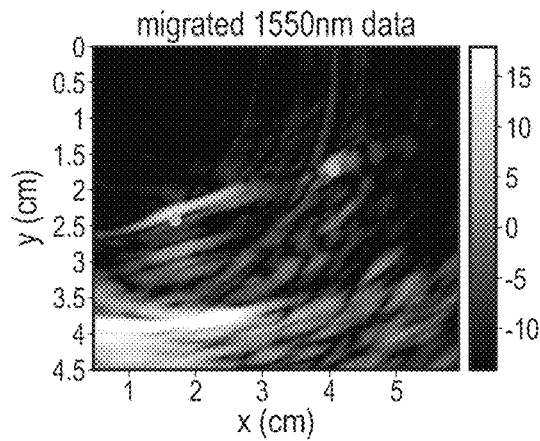
Figure 7D:
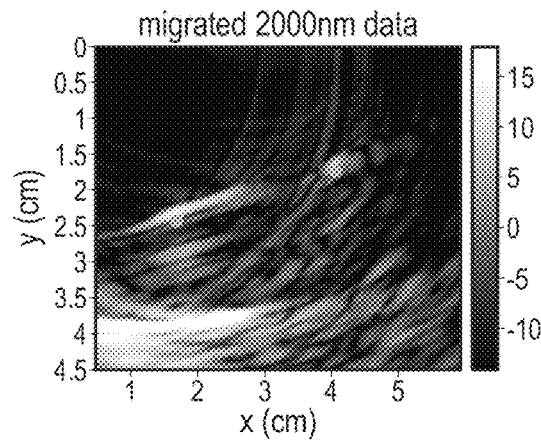

The energy of a laser-generated ultrasound source signal is calculated by integrating the spectrum of each waveform in the 0.5 MHz to 2.5 MHz band (FIGS. 6A-6C). The energy is also corrected by the efficiency term discussed above with respect to Eq. 17, and compared to $\mu_a^2$ for water, as shown in FIGS. 6A-6C. As shown in Eq. 17, the energy of the LUS source signal should strongly depend on $\mu_\alpha^2$ for the experiments conducted. FIGS. 6A-6C show the energy of the LUS source signals from beef, chicken, and pork samples, as well as the energy compensated by the efficiency factor from Eq. 17 vs. optical wavelength on a logarithmic scale. The $\mu_\alpha^2$ curve for water is also plotted as a function of optical wavelength on a second y-axis to allow comparison. The energy as a function of optical wavelength for each tissue closely follows the $\mu_\alpha^2$ curve for water.

Results—Impact of Generation Laser Optical Wavelength on Image Quality

The images formed using the synthetic aperture focusing technique from the data collected using the third experimental setup clearly show the two rods imbedded in the beef sample, as well as the beef-table interface (FIGS. 7A-7D).

The relative brightness of the rod and table-beef interface increase with optical wavelength of the generation laser, illustrating a strong dependence of image SNR on the generation laser wavelength for biological tissues due to the increasing absorption coefficient of biological tissue with optical wavelength. The wires are the bright spots in the images at z=2.25 cm and z=1.75 cm, and are indicated schematically by the greens dots in FIGS. 7A-7D. The bright return at z=4.0 cm is the beef table interface. All images are acquired on a same sample with matching scan patterns and are displayed on matching gray scales.

DISCUSSION

Figure 8:
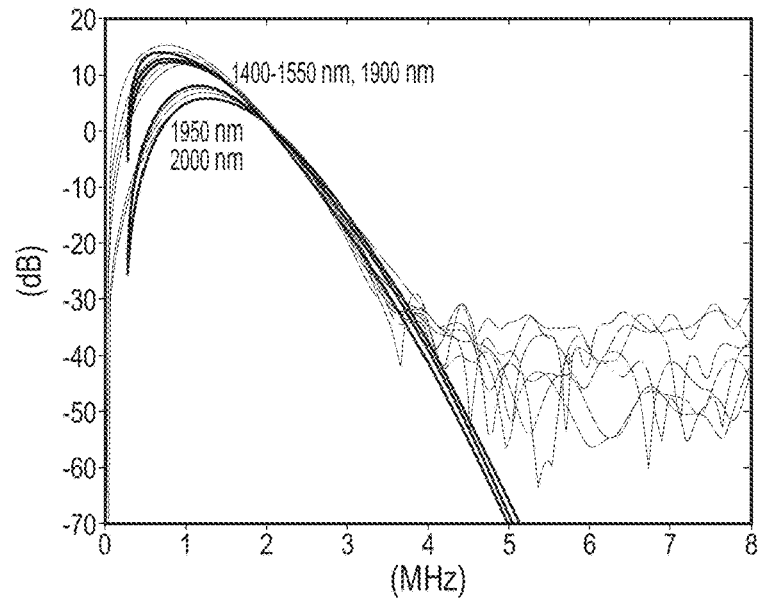
FIG. 8 is a graph of spectra of LUS source signals for a beef sample at optical wavelengths of 1400 nm to 1550 nm and of 1900 nm to 2000 nm (gray lines) compared to theoretical predictions including surface roughness acoustic attenuation and transducer response (black lines). The curves illustrated in FIG. 8 have been arbitrarily shifted vertically to illustrate agreement in the spectral slope (controlled by a (mean square height of roughness) and a (acoustic attenuation)) between the observations and the theoretical predictions.

The waveform and spectral shapes of laser-generated ultrasound source signals observed in the tissues tested are broadly consistent with the theory for LUS source signals in pure water when acoustic attenuation and surface roughness are taken into account. Further analysis of the laser generated ultrasound source signals suggests Eq. 17 and Eq. 18 are valid for biological tissue at optical wavelengths from 1400 nm to 1550 nn and 1900 nm to 2000 nm (FIG. 8). At these optical wavelengths, $\mu_a$ is greater than $\mu_s$, which means the effect of scattering in the medium is small compared to absorption. For the theoretical predictions in FIG. 8, Eq. 18 is used with values of $\mu_a$ taken from the literature, $\sigma$=1.5× $10^{-4}$, and a=−2.9 dB-MHz.

The agreement between the model and measured data spectral slope (FIGS. 5A-5B and FIG. 8) confirm that the spatial resolution of non-contact LUS imaging systems using a pulsed laser source is most prominently controlled by the roughness of the tissue surface and the acoustic attenuation of the tissue. This can result in patient and body-part dependent resolution and system performance. These results also indicate that the resolution of a non-contact LUS imaging system will likely be better than 3 mm since there is always acoustic energy in the frequency range above 500 kHz (i.e., $\lambda$=c/f).

The relative energy in the observed LUS source waveforms for all three tissues agrees with the absorption curve for water (FIGS. 6A-6C), as predicted by Eq. 17 and Eq. 18. The optimal optical wavelengths for maximizing laser generated ultrasound source energy are from 1400 nm to 1550 nm, as well as 1900 nm to 2000 nm, consistent with previous studies.

These results additionally suggest that higher bandwidth ultrasonic signals can be generated in humans because the acoustic attenuation is typically 0.5 dB/MHz-cm, which is smaller than beef. Additionally, the surface of human skin, in many cases, will be smoother than the surface of the samples tested here.

Figure 9:
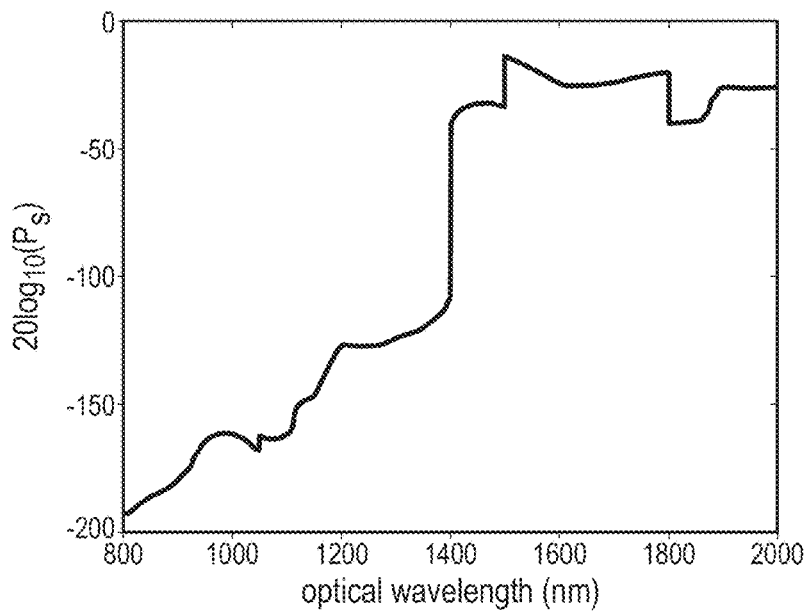
FIG. 9 is a graph of an LUS source amplitude (Eq. 17) at 1.5 MHz vs. optical wavelength when accounting for ocular Maximum Permissible Exposure (MPE) (Lasers Institute of America, 2007) to a 1 ns to 1 µs long pulse. Larger sources can be generated at wavelengths above 1400 nm at safe optical exposure levels. The left axis of FIG. 9 provides a log 10 of pressure in Pascals.

These are suitable wavelength ranges for development of non-contact LUS imaging systems for medical purposes. Optical hardware operating in these ranges is commonly available. Additionally, the high optical absorption values for water in these ranges can allow eye and skin safe designs with larger fluence levels compared to wavelengths less than 1400 nm. As a result, acoustic sources with more energy can be generated (FIG. 9) due to high optical absorption and higher safety thresholds in the 1400 nm to 1550 nm and 1900 nm to 2000 nm wavelength ranges.

Lastly, it is seen (FIGS. 7A-7D) that the image quality improves with increasing optical wavelength of the generation laser, consistent with the results showing that energy in the LUS source wave increases with increasing optical wavelength of the generation laser. These images demonstrate the importance of choosing a generation laser wavelength to maximize image quality by maximizing the source amplitude. In the context of designing a non-contact LUS system for imaging biological tissue, a generation laser wavelength where the absorption coefficient of water and the acceptable human exposure limits are high can be chosen to generate the largest amplitude LUS source possible. In cases where treatment of the sample surface is acceptable, it may be advantageous to use films designed to have large optical absorption and thermal expansion coefficients.

Example 2. Soft Tissue Imaging with Laser Ultrasound

A fully non-contact laser ultrasound (LUS) system is developed and used to acquire images of pork belly tissue samples purchased from the butcher. The experimental results show the system can detect fat and muscle boundaries, as well as needles, in the pork tissue samples to 4.5 cm beneath the tissue surface. The LUS system is comprised of a 1550 nm pulsed laser for signal detection and a commercially available 532 nm multi-pixel homodyne interferometer (for signal detection). A non-contact medical LUS imaging system can deliver repeatable, quantitative sound speed and density data and volumetric images without contacting or applying a coupling material to the patient.

In this work a 1550 nm generation laser and commercially available 532 inn multi-pixel homodyne interferometer is employed to ultrasonically image samples of pork tissue. Although the optical exposure at the sample is not made skin safe, the exposure levels can be made skin safe with minor engineering upgrades to the system. The images from the LUS system compare favorably with conventional ultrasound images acquired using a clinical imager and an ultrasound research device.

Methods—Laser Ultrasound Experimental Setup

The laser ultrasound (LUS) system includes a generation laser, a detection laser, precision translation stages, and electronics for data capture (see FIG. 2). The generation laser is a 1550 nm passively Q-switched 9 ns pulsed laser with a 10 Hz pulse rate and 2 mm diameter collimated beam (Optitask LID, Netanya, Israel). The detection laser is a 532 nm, 500 mW multichannel homodyne interferometer with a 0.1 mm diameter focal spot. A shutter (Uniblitz, Rochester, NY, USA) is in front of the interferometer to reduce the total on optical exposure onto the sample. The translation stages (SG9P 26-100 Sigma Koki, Tokyo, Japan) allow for precise x-y positioning of the samples relative to the detection laser and source laser. The system is controlled using LabView (National Instruments, Austin, TX, USA), and data sampling and saving is performed with a 200 MS/s DAQ (NI PXie-1073, National Instruments, Austin, TX, USA) using a 25 MHz sampling rate.

Data collection proceeds as follows. A single laser generated acoustic trace is initiated by an optical pulse emanating from the source laser, which generates a thermal stress concentration, an acoustic source, at the surface of the sample. Simultaneously, the source laser sends a trigger to the shutter to open, and the detection laser measures the ultrasonic vibrations at the surface of the sample for 1 ms. The measured vibrations are digitized by the DAQ, and the shutter closes. A number of traces are gathered at a single location for signal averaging purposes. The linear stage then linearly translates Δx mm and then the process is repeated. A full scan consists of N trace locations, where Q traces are collected at each location.

In this work, the generation laser spot is 2 mm above the detection laser spot (nearly monostatic (source and receiver co-located)), and 100 traces (Q=100) are collected at each trace location. The line spacing between trace collection is 0.5 mm or 0.25 mm. depending on the data set and total scan distances are 2-4 cm, yielding 80-120 trace locations in a scan. Each trace is 200 μs long yielding 5000 time samples ($N_t$) per trace.

Methods—Optical Exposure

The 1550 nm generation laser is skin and eye safe by ANSI standards (Lasers Institute of America, 2007). The detection laser is not skin or eye safe (Lasers Institute of America, 2007); however, if the detection laser were only on for the 200 μs trace measurement time, it would be skin safe. Due to difficulties in synchronizing the generation laser to a chopper wheel, it was not possible to reduce the detection laser time to 200 μs.

Methods—Post Processing

At each scan location the traces are processed to increase the signal to noise ratio (SNR) of the data ensamble. The ensamble average of all the trace samples is taken and multiplied by the coherence of the trace as given by $$\hat{t}_n = \overline{T_n} \frac{\left(\sum_{q=1}^{Q} tr_q\right)^2}{Q\sum_{q=1}^{Q} t_q^2} \quad (20)$$

where $\hat{t}_n$ is the processed trace ($N_t \times 1$ vector) from the $n^{th}$ trace location, $\overline{T_n}$ is the mean of all the traces at the $n^{th}$ trace location and tr is a $N_t$ by Q matrix. The sum in Eq. 20 is across the columns of tr (the ensamble average of Q traces). The final data set from a single scan is $\hat{T}$, which is a $N_t$ by N matrix containing the processed traces from each trace location.

Methods—Imaging Technique

A conventional imaging process called the synthetic aperture focusing technique (SAFT) in combination with a coherence factor (CF) is applied to the data sets to generate ultrasound images from the data collected from the LUS system. The image formation process is described mathematically by:

$$I_{i,j} = CF_{i,j} * \sum_{n=1}^{N} \hat{T}(dv_{n,i,j}, n) \quad (21)$$

where I is the image and i and j are the row and column indices of the image, N is the number of sources and $dv_{n,i,j}$ is the focusing delay for trace data n to image the location i, j in image space given by:

$$\delta_{n,i,j} = \left[\frac{f_s}{c}\left(\sqrt{(x_{i,j}-x_n^s)^2 + (y_{i,j}-y_n^s)^2} + \sqrt{(x_{i,j}-x_n^r)^2 + (y_{i,j}-y_n^r)^2}\right)\right] \quad (22)$$

where c is the sound speed in m/s, $f_s$ is the sampling rate of the data in (Hz), $x_n^s$ and $x_n^r$ are the x position of the $n^{th}$ transmitter and receiver, $y_n^s$ and $y_n^r$ are the y location of the $n^{th}$ transmitter and receiver, and the brackets indicate the quantity rounded to the nearest integer. In the monostatic case, the source and receive positions are identical. The coherence factor $CF_{i,j}$ is given by:

$$CF_{i,j} = \left(\frac{\left(\sum_{n=1}^{N} \hat{T}(\delta_{n,i,j}, n)\right)^2}{N\sum_{n=1}^{N} \hat{T}^2(\delta_{n,i,j}, n)}\right). \quad (23)$$

Methods—Conventional Ultrasound Experimental Setup

The images from the LUS system are compared to images from a clinical imager (General Electric (GE) LOGIQ E9, Boston, Ma, USA) clinical ultrasound imaging system, as well as a 64-channel ultrasound research system (Cephasonics, Santa Clara, Ca, USA). The images with the clinical imaging system are taken with a 4.4 cm aperture 9 MHz linear probe using cross beam imaging. The data with the research system is taken with a 3.5 cm 6 MHz linear probe with 128 elements. The research system is programmed to acquire 128 monostatic pulse-echo traces (one at each element on the probe) to replicate the scan done with the LUS system but with traditional piezoelectric transducer technology. The data set from the research system is converted into an image using the same imaging processes applied to the LUS system data.

Results

The experimental results consist of LUS and conventional US scans of three pieces of pork belly purchased from the butcher. After initial scanning of the samples, needles are inserted into the tissue samples to create strong scattering targets in the tissue. Ultrasound images generated using the LUS system are compared with a clinical imagers and images from an ultrasound research system, which replicates the LUS scan but at a higher frequency.

Results—Sample One

Figure 11A:
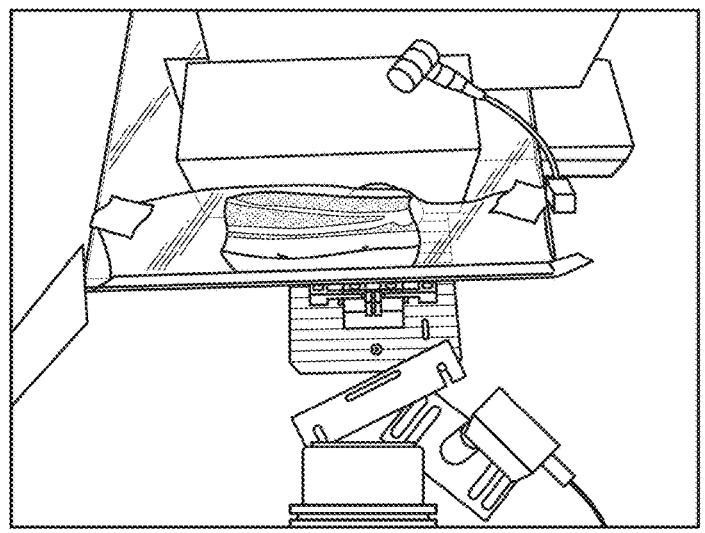
FIGS. 11A-C illustrate a first sample, laser ultrasound traces, and an image obtained from scanning the sample.
Figure 11B:
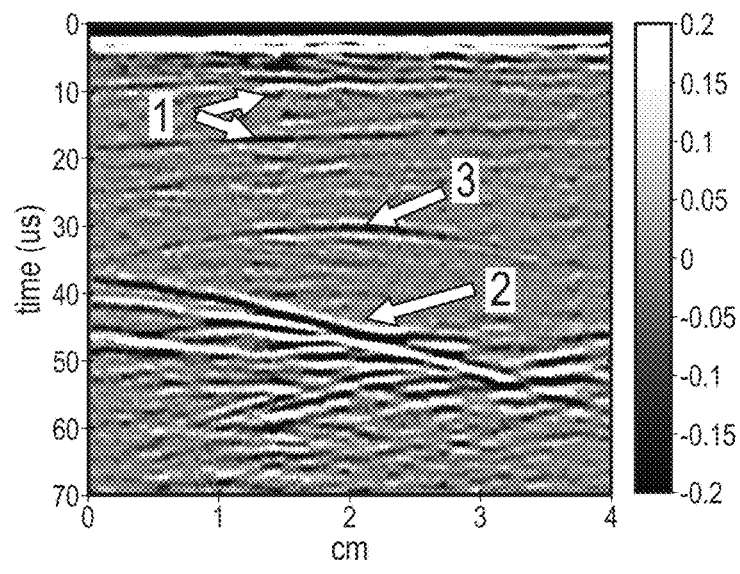
Figure 11C:
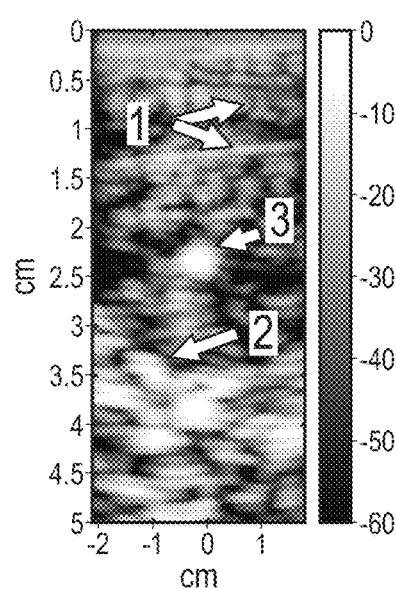

The results from sample one (FIG. 11A) show reflections or backscatter from soft tissue inhomogeneity's in the sample using the LUS system (FIGS. 11B-11C). The traces in FIG. 11B show reflections from the fat muscle boundaries (arrow 1) and from the back surface of the sample (arrow 2). The SNR from trace to trace is not always the same, but the trends in the data are still visible. The inconsistent SNR is likely due to small deviations in the distance of the sample surface to the detection laser lens, which brings the detection laser in and out of focus on the sample. The bright return along the top of FIG. 11B is the direct acoustic wave created by the generation laser pulse.

The LUS image created from the traces in FIG. 11B is shown in FIG. 11C. The structures in the LUS image are located in similar positions as the fat and muscle layers seen in FIG. 11A. Scattering features are seen in the sample at 0.75 cm and 1.4 cm depths. A single scatterer is seen at 2.25 cm depth (arrow 3). The back portion of the sample is not flat and starts at approximately 3.5 cm in depth.

Figure 12A:
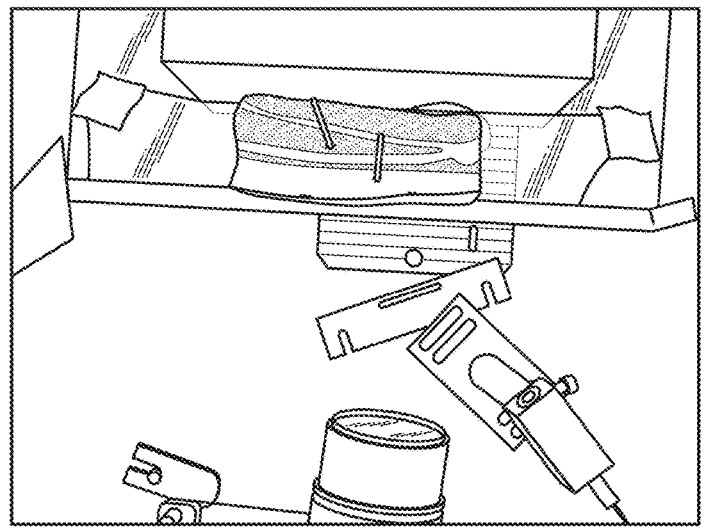
FIGS. 12A-C illustrate the first sample of FIG. 12A with inserted needles, and the LUS traces and an image obtained from scanning the sample.
Figure 12B:
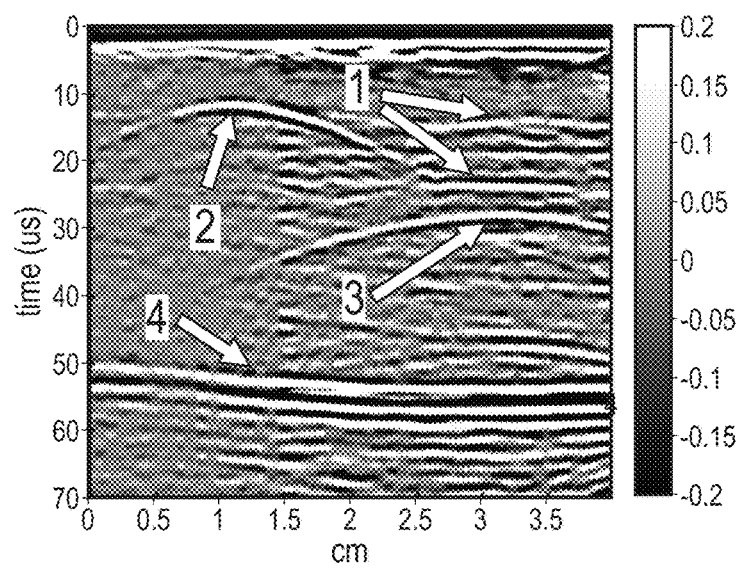
Figure 12C:
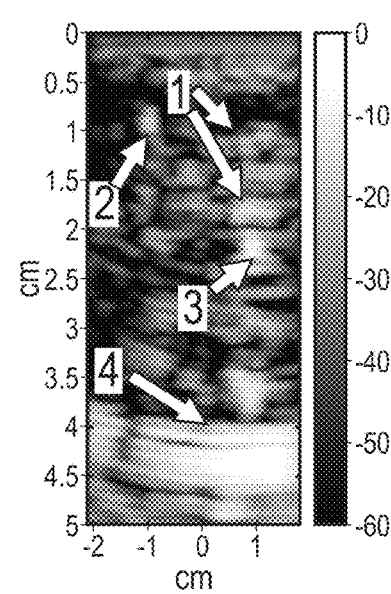

Needles are inserted into the sample and an aluminum block is placed in contact with the back of the sample (FIG. 12A). Gel couples the block to the sample (FIG. 12A) and the sample is reimaged. The soft tissue reflections (arrow 1) and the reflections from the needles (arrows 2 and 3) are visible in the traces (FIG. 12B) and the reconstructed image (FIG. 12C). The needles are seen at 1 cm and 2.25 cm depths (arrows 2 and 3), and the first soft tissue reflections are seen at 1 and 1.75 cm depth (arrow 1). The reflection from the block/sample interface is seen at 4 cm range (arrow 4) (FIG. 12C). It appears the scattering from the soft tissue boundaries is partially shadowed on the left half of the image by the left most needle. It is also possible the detection laser is slightly out of focus from 0 to 1.25 cm along the scan aperture.

Figures 13A, 13B, 13C, 13D:
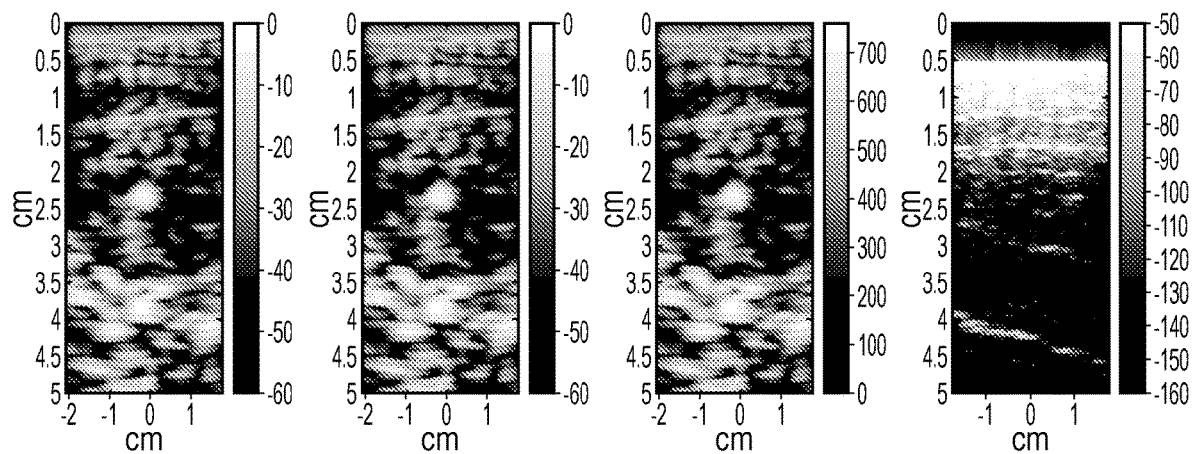
FIGS. 13A-D illustrate LUS images of the first sample alongside images of the sample taken with conventional ultrasound imaging technology.
Figure 13E:
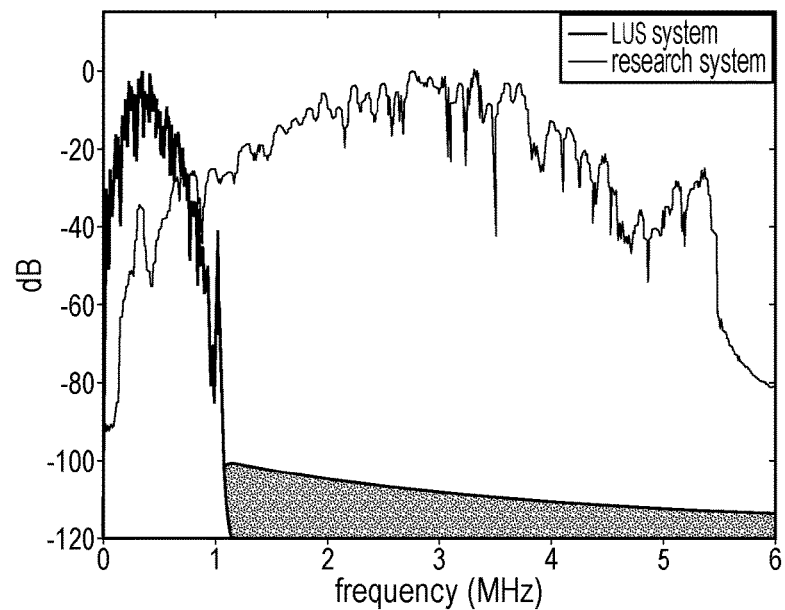
FIG. 13E is a graph of spectrums of a trace from the LUS system and the research system. The trace from the research system has an approximate bandwidth and center frequency of 4 MHz and 3 MHz, respectively. The LUS system has a bandwidth and center frequency of 750 kHz and 500 kHz, respectively. The higher center frequency and bandwidth of the research system trace indicates the images generated from the research system should be of higher resolution than those generated from the LUS traces.

Images of the sample obtained from the clinical images and the research system (FIGS. 13C, 13D) are seen alongside the LUS images from FIGS. 11C and 12C in FIGS. 13A-13D. The presence of the soft tissue layers in the first 1.5 cm are seen in all the images. The layer starting at 2.5 cm depth in the clinical and research system images is not easily seen in the LUS images. The images from the clinical system and research system are taken with the needles in the sample. The needles are easily seen in the clinical image but not the research system image. This is likely due to out of plane specular scattering off the needles as the samples were transported between image acquisitions. Overall the resolution of the piezoelectric systems is much better than the LUS system because the frequency content of the LUS source signal is much lower than the source signal from the piezoelectric systems (FIG. 13E).

Results—Sample Two

The results from sample two (FIG. 14A) show reflections or backscatter from soft tissue inhomogeneity's in the sample (arrow 1) using the LUS system (FIG. 14B, 14C). The traces in FIG. 14B show reflections from the fat muscle boundaries (arrow 1) and from the back surface of the sample (arrow 2). The bright return along the top of FIG. 14B is the acoustic wave created by the generation laser pulse. The LUS image created from the traces in FIG. 14B is seen in FIG. 14C. The structures in the LUS image are located in similar positions as the fat and muscle layers seen in FIG. 14A. Scattering features are seen in the sample at 1, 2, and 2.5 cm depths (arrow 1).

Figure 15A:
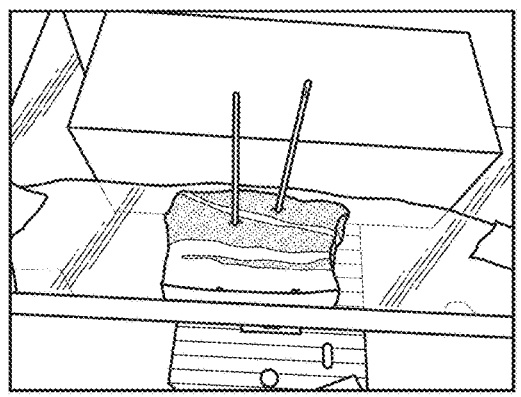
FIGS. 15A-C illustrate the second sample of FIG. 14A with inserted needles, and the LUS traces and an image obtained from scanning the sample.

Needles are inserted into the sample and it is re-imaged with the LUS system (FIG. 15A). The soft tissue reflections (arrow 1) and the reflections from the needles (arrow 2) are visible in the traces (FIG. 15B) and the reconstructed image FIG. 15C. The needles are seen at 3 cm and 3.25 cm depths (arrow 2) and the soft tissue reflections are seen at 1, 2 and 2.5 cm-depths (arrow I). The reflection from the block/sample interface is seen at 4 cm range (FIG. 15C) (arrow 3).

Figures 15B, 15C:
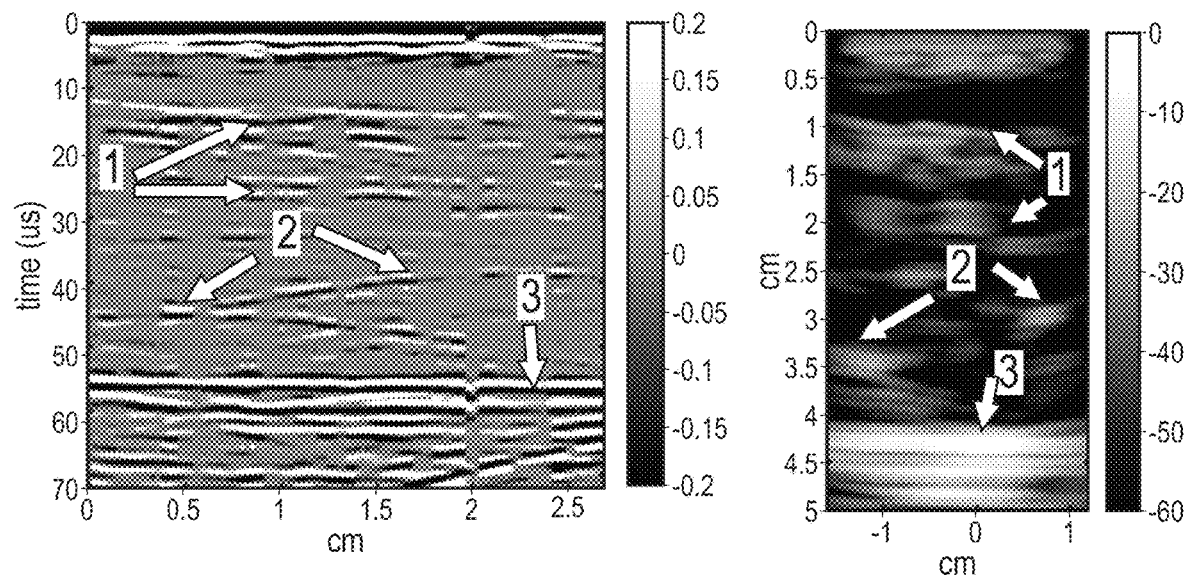
Figures 16A, 16B, 16C, 16D:
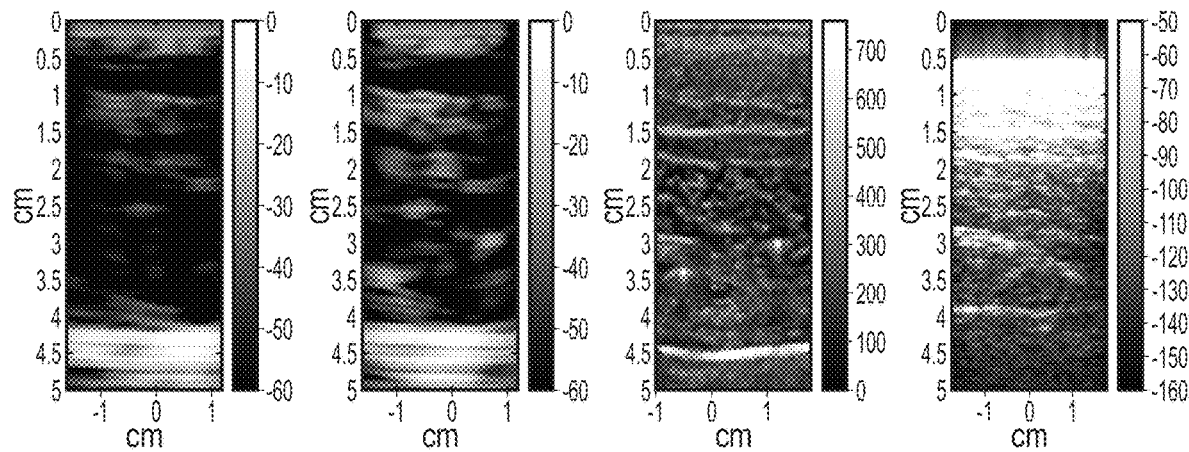
FIGS. 16A-D are LUS images of the second sample alongside images of the sample taken with conventional ultrasound imaging technology.

Images of the sample obtained from the clinical imager and the research system (FIG. 16C, 16D) are seen alongside the LUS images from FIGS. 14C, 15C, in FIGS. 16A-16D. The presence of the soft tissue layers in the first 2 cm are seen in all the images. The layer starting at 3 cm depth in the clinical and research system images is not easily seen in the LUS images. The images from the clinical system and research system are taken with the needles in the sample. The needles are easily seen in the clinical image but not the research system image. This is likely due to out of plane specular scattering off the needles. Overall the resolution of the piezoelectric systems is much better than the LUS system because the frequency content of the LUS source signal is much lower than the source signal from the piezoelectric systems (FIG. 13E).

Results—Sample Three

Figure 17A:
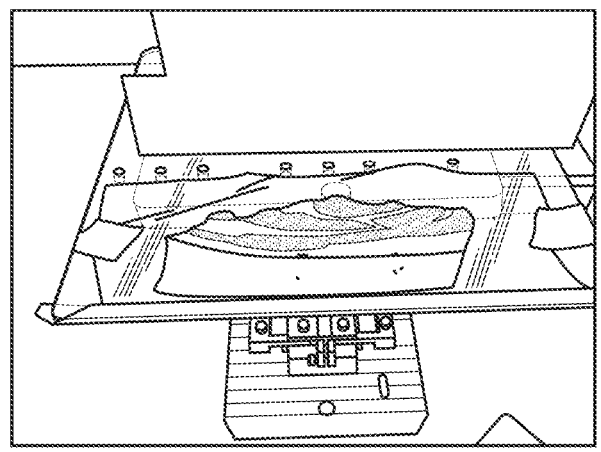
FIGS. 17A-C are images of a third sample, LUS traces, and an image obtained from scanning the third sample.
Figure 17B:
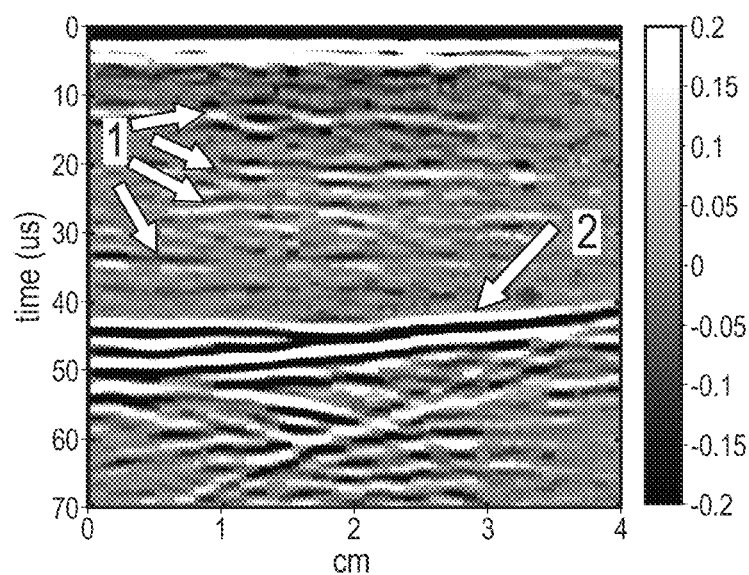
Figure 17C:
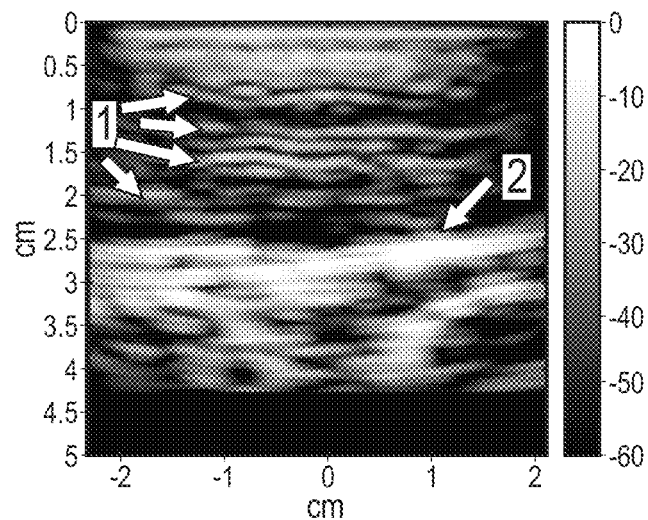

The experimental results from sample three (FIG. 17A) show reflections or backscatter from soft tissue inhomogeneities in the sample using the LUS system (FIG. 17B, 17C) (arrow 1). The traces in FIG. 17B show reflections from the fat-muscle boundaries (arrow 1) and from the back surface of the sample (arrow 2). The bright return along the top of FIG. 17B is the acoustic wave created by the generation laser pulse. The LUS image created from the traces in FIG. 17B is seen in FIG. 17C. The structures in the LUS image are located in similar positions as the fat and muscle layers seen in FIG. 17A. Scattering features are seen in the sample at 0.75, 1.25 and 2 cm depths (arrow 1).

Figure 18A:
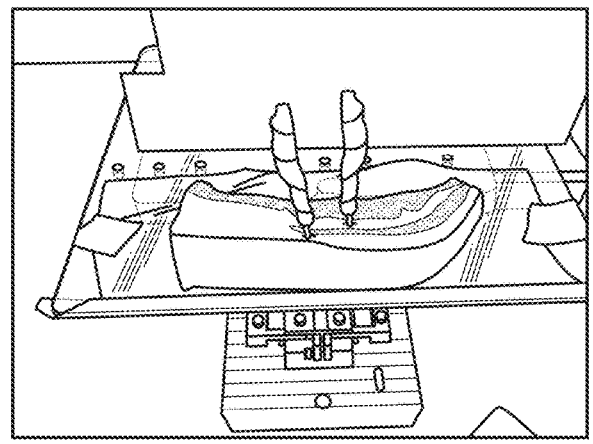
FIGS. 18A-C illustrate the third sample of FIG. 17A with inserted needles, and LUS traces and an image obtained from scanning the sample.
Figures 18B, 18C:
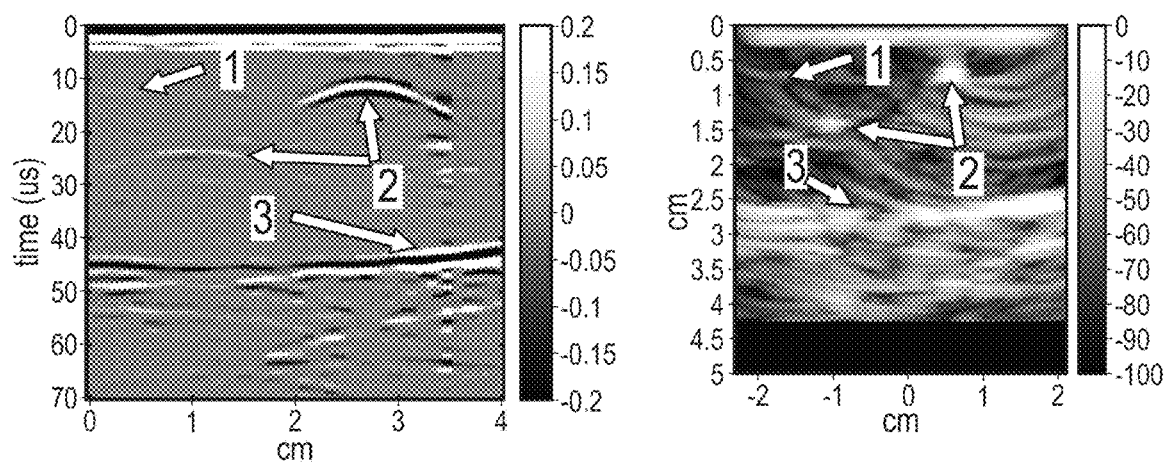

Needles are inserted into the sample and it is re-imaged with the LUS system (FIG. 18A). The soft tissue reflections (arrow 1) and the reflections from the needles (arrow 2) are visible in the traces ((FIG. 18B) and the reconstructed image ((FIG. 18C). The needles are seen at 0.75 cm and 1.5 cm depths. Soft tissue reflections are seen at 0.75 cm depth. The reflection from the sample back surface is seen at 2.5 cm depth ((FIG. 18C) (arrow 3).

Figures 19A, 19B, 19C:
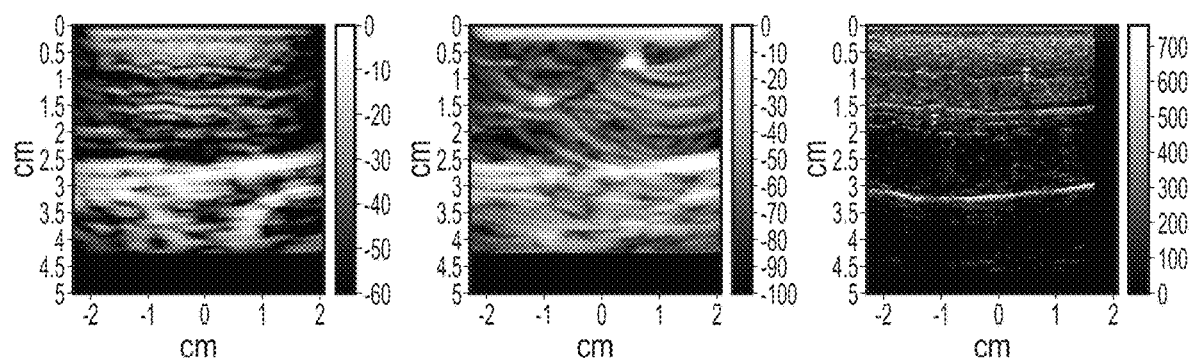
FIGS. 19A-C are images of the third sample, including LUS images of sample alongside images taken with conventional ultrasound imaging technology.

Images of the sample obtained from the clinical imager (FIG. 19C) are seen alongside the LUS images from FIGS. 17C, 18C in FIGS. 19A-C. The presence of the soft tissue layers in the first 2 cm are seen in all the images but are less pronounced when the LUS image with needles in the sample (FIGS. 19A-C). The image from the clinical system is taken with the needles in the sample. The needles are easily seen in the clinical image as well as the LUS image. The soft tissue structure is also similar between the LUS image and the clinical image. Overall the resolution of the clinical system is much better than the LUS system because the frequency content of the LUS source signal is much lower than the source signal from the clinical system (FIG. 13E).

DISCUSSION

A laser ultrasound LUS system is developed and employed to ultrasonically image pork belly tissue purchased from the butcher. The images, generated without contacting or treating the sample, show the fat and muscle layers can be imaged, as well as needles up to 4.5 cm beneath the tissue surface. Many of the images from the LUS system show structural agreement with conventional ultrasound images acquired by contacting the sample using a clinical imager and an ultrasound research device. Further improvements to the LUS system, such as enabling acoustic focusing on transmission, can enhance the LUS image quality.

Example 3. Adaptive Beamforming with a Synthetic Circular Ultrasound Array for Imaging Bone and Soft Tissue An adaptive beamforming technique is developed for imaging the bone and soft tissue of a limb. Data is acquired with a single element transducer in a tank. The resulting imagery are shown to have similar dynamic range to conventional clinical imagers. Limb imaging is of clinical interest for muscle health monitoring, bone fracture detection, and general soft and bone tissue imaging. The process is demonstrated on a numerical data set, phantoms, animal tissue, and human tissue in vivo. Broadband transducers with center frequencies of 1.0, 2.25 and 5.0 MHz are used. Bone has substantially higher density and sound speed than the surrounding soft tissue. This acoustic impedance mismatch makes it difficult to create high resolution and SNR images using circular aperture ultrasound scanners due to sidelobe artifacts masking weaker scatterers. The process presented successfully mitigates these problems and produces images with reduced artifacts and noise floor.

Imaging techniques that produce clinically useful images in parts of the body with bone inclusions can present significant algorithmic and measurement challenges due to the large sound speed and density variations (e.g., 1500 m/s and 100 kg/m$^3$) at bone-soft tissue interfaces. Strong reflections from the bone due to the large changes in sound speed and density can shadow or overwhelm scattering and reflections from other anatomical regions of interest. For soft tissue, modest sound speed and density variations on the order of 50 m/s and 50 kg/m$^3$ are typical. For such variations, conventional synthetic aperture focusing technique (SAFT) or delay and sum (DAS) imaging processes can work effectively. When imaging bone, these processes will not typically generate high-quality ultrasound imagery as the underlying image formation assumptions are violated.

Adaptive beam forming (ABF) is a popular technique to reduce sidelobe interference, and, in some cases, enhance resolution of soft tissue images. Among the many choices of processes, the minimum variance distortionless response (MVDR) and generalized sidelobe canceler (GSC) processes and their variants are popular and can provide good performance. Generally, the MVDR and GSC beam formers attempt to weight the channel data used to create an ultrasound image pixel value in a way that minimizes the variance of the summed data, thereby reducing sidelobe interference from other scatterers. Estimating the weighting function requires inverting a data covariance matrix for each image pixel, which can be computationally expensive. The ABF techniques appear to be less popular in the ultrasound computed tomography (USCT) space compared to probe-based ultrasound, which is likely due to the large computational cost of optimization based ABF processes.

Image quality can also be enhanced using a coherence factor (CF) or short lag coherence factor (SLCF), which weights every image pixel based on a coherence measure of the summed data used to create the image pixel. The CF, as well as the generalized coherence factor (GCF), and their variants can require minimal computational costs.

Inverting for an image using the known point spread function (PSF) of the imaging system is another approach to improve image resolution and signal to noise ratio (SNR). In the circular synthetic aperture sonar (CSAS) community, compressive sensing techniques show promising results for volumetric imaging. Matched field processing, where sound speed waveguide are taken into account during the beamforming process have also shown success. In the medical ultrasound tomography (UST) space, the angular dependence of scatterers has been used to produce maximum intensity projections to construct images with improved SNR. These techniques produce satisfying results but are computationally expensive and/or require full arrays to estimate the angular dependence of the scatterers.

In this study, a computationally efficient ABF technique for imaging bone and soft tissue that uses the reflected wave direction of arrival (DOA) at the transducer surface to reduce sidelobe interference, referred to here as the echo flow (EF) technique, is developed. The EF method is combined with a CF weighting to produce a final image. The experimental results show that the process improves the SNR of images and reduces sidelobe interference from strong scatterers compared to DAS and CF techniques alone.

Data is collected using a mechanically scanned single element transducer (monostatic acquisition) in a cylindrical tank and using a dual transducer setup (bi-static data acquisition). The performance of the combined EF and CF technique is evaluated on monostatic synthetic data, a phantom, two bovine shank samples, and a human limb under an internal review board (IRB) approved study using 1.0, 2.25, and 5.0 MHz transducers. The EF technique performance is also evaluated on bi-static data collected on two different bovine shanks using 1.0 MHz transducers.

Methods—Scanning Hardware

The experimental data collection is performed using a custom-made, single-element, dual-transducer, cylindrically-scanning immersion UST scanner (UST scanner) (see, for example, FIG. 1). Both transducers can be independently positioned over the entire 3600 aperture and translate ~7 cm vertically for t acquiring multiple 2-D slice or volume images of a target and enabling iterative development of scanning procedures. The two transducers are also removable, allowing testing of transducers with varying beam properties and frequency. Further details describing general mechanical and electrical design of a UST scanner can be found in Zhang et al., "A single element 3D ultrasound tomography system," Proc. Annu. Int. Conf. IEEE Eng. Med. Biol. Soc. EMBS (2015).

The data acquisition system consists of a low frequency pulser (DPR300, Imaginant, Pittsford, Ny, USA), which drives the transmit transducer. The pulser also preforms analog gain and filtering of the A-line signals from the receiving transducer, which can be the same as the transmitter. The analog signal coming from the pulser is digitized at 50 MHz (NI PXie-1073, National Instruments, Austin, TX, USA) and streamed to a PC where the signal is saved for processing. Further details describing general data acquisition system can also be found in Zhang et al., "A single element 3D ultrasound tomography system," Proc. Annu. Int. Conf IEEE Eng. Med. Biol. Soc. EMBS (2015).

Monostatic and bistatic scans are employed to collect the experimental data sets. In monostatic scans, a single transducer transmits and detects sound waves. The monostatic scan consists of sequentially recording 1533 pulse-echo channel data traces at 1533 locations equally spaced by 0.2345° around the tank, resulting in a full 3600 synthetic aperture. For these scans, 1.0 MHz, 2.25 MHz, and 5 MHz broadband custom-made, cylindrically-focused transducers are employed, which produce a 650 full beam width fan beam pattern.

Figure 20:
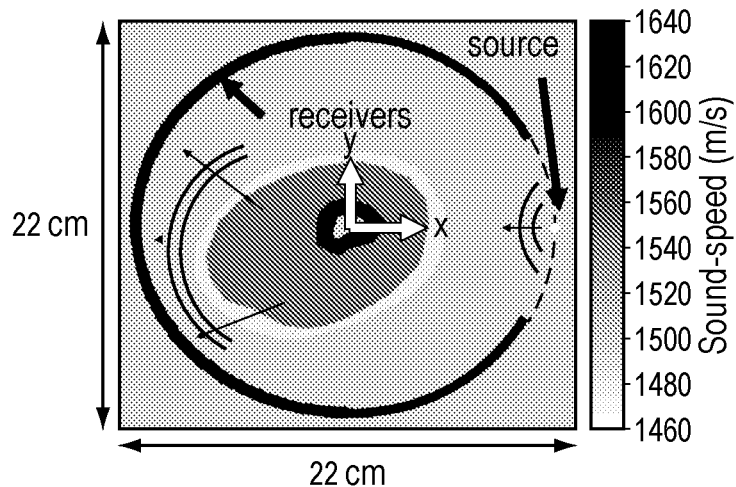
FIG. 20 is a schematic of the ultrasound tomography (UST) tank and coordinate system for image reconstruction. The z axis is into the page.

In the bistatic scans, one transducer transmits and a second transducer receives the transmitted sound waves. The bistatic scan consists of 72 transmit locations equally spaced 5° apart, resulting in a 360° synthetic aperture. At each transmit location, 1333 channel data traces are sequentially acquired from the receiving transducer at 1333 equally distributed spatial locations (0.2345° apart), resulting in a 313° receive aperture. A full 3600 receive aperture was prevented due to mechanical interference between the mounting brackets. The interference makes 23.5° of the circular aperture, centered on the transmit bracket, inaccessible to the receiver. For all bistatic scans, a 1 MHz (broadband) fan beam transducer with 65° full beam width is used for transmit. For receive, a matching 1.0 MHz broadband point receiver is used. A schematic of the tank and coordinate system is shown in FIG. 20.

The source transducers and system electronics were characterized with a calibrated a hydrophone to ensure the scans do not exceed the food and drug administration (FDA) standards for ultrasound use on humans. All scanning procedures described were approved by the MIT internal review board and committee on animal care.

Methods—Imaging Process

The imaging process is a delay and sum (DAS) technique that uses direction of arrival information (DOA) to do adaptive beamforming (ABF) with a single element or many elements. A coherence factor (CF) is also employed to further improve image quality.

Delay and Sum (DAS)

The DAS technique assumes that the medium is homogeneous and contains point scatterers and that the Born Approximation holds. Mathematically, the DAS process for a monostatic data acquisition can be defined as:

$$I_{i,j} = \sum_{n=1}^{N} D(\delta_{n,i,j}, n) W_{i,j}(n) \quad (24)$$

where I is the image and i. and j are the row and column indices of the image, N is the number of sources, D is a matrix containing experimental data where each column contains the channel data, $\delta_{n,i,j}$ is the focusing delay for channel data n to image the location i,j in image space, W is the weight to apply to each element of channel data to image the location i,j in image space. For conventional DAS, W is equal to 1. Reducing the value of W for an A-line that is interfering with the signal of interest can improve image quality. The DAS technique employed here also corrects for the beam width of the transducer. Assuming a point source and a two-dimensional domain, the delay vector $\delta_{n,i,j}$ is given by Eq. 22, repeated here for convenience:

$$\delta_{n,i,j} = \left[\frac{f_s}{c}\left(\sqrt{(x_{i,j} - x_n^s)^2 + (y_{i,j} - y_n^s)^2} + \sqrt{(x_{i,j} - x_n^r)^2 + (y_{i,j} - y_n^r)^2}\right)\right] \quad (22)$$

where c is the sound speed in (m/s), $f_s$ is the sampling rate of the data in (Hz), $x_n^s$ and $x_n^r$ are the x-position of the $n^{th}$ transmitter and receiver, $y_n^s$ and $y_n^r$ are the y-location of the $n^{th}$ transmitter and receiver, and the brackets indicate the quantity rounded to the nearest integer. In the monostatic case, the source and receive positions are identical. A coherence factor is used to improve image quality using the DAS technique. The coherence factor is defined as in Eq. 23, repeated here for convenience:

$$CF_{i,j} = \left(\frac{\left(\sum_{n=1}^{N} \hat{T}(\delta_{n,i,j}, n)\right)^2}{N \sum_{n=1}^{N} \hat{T}^2(\delta_{n,i,j}, n)}\right) \quad (23)$$

and is multiplied by $I_{i,j}$ to generate a coherence factor weighted image. The coherence factor power (CFP) is a scalar used to adjust the impact of the CF on the image.

DOA Estimation

The DOA-based adaptive beamforming process can require accurate calculation of the DOA. To estimate DOA, the Canny edge detector (Canny, "A Computational Approach to Edge Detection," IEEE Trans. Pattern Anal. Mach Intell., (1986)) and Hough transform (Duda and Hart, "Use of Hough Transformation to Detect Lines and Curves in Pictures," Graph. Image. Process., 15, 11-15 (1972)) are employed in a two-step process to estimate DOA. The DOA estimation process consists of separating D into 11 by 11 patches with 7 sample overlap in the row and column (time and space) directions. On each patch, the Canny edge detection is applied, and the output is passed to a Hough transform, which outputs an angle. The angle output from the Hough transform is the estimate of the DOA of the signal (if there is one present) in the data patch.

During monostatic scans, the DOA estimation approach described assumes the DOA does not change significantly as the transducer moves 2.5° over the circular aperture and that the incident waves on the transducer are plane waves.

What differentiates this technique from others is that $W_{i,j}(n)$ from Eq. 24 is defined using the DOA information instead of estimating a $W_{i,j}(n)$ based on minimum variance or some other statistical measure. In our case, the DOA and amplitude data define $W_{i,j}(n)$ according to the following expression for a Gaussian like function:

$$W_{i,j}(n) = \exp\left(\frac{-(\theta(\delta_{n,i,j}) - \phi_{i,j})^2}{2A_{thresh}}\right) \quad (25)$$

where $\theta$ is the DOA matrix that contains DOA estimates for each index of D, $\Phi_{i,j}$ is the expected DOA from a scatterer in the image at the position i,j, and $A_{thresh}$, is defined as:

$$A_{thresh} = \begin{cases} \alpha_1 A & \text{for } A < \epsilon \\ \alpha_2 & \text{for } A \geq \epsilon \end{cases} \quad (26)$$

where A $(-|H(D)|^2 + \max(|H(D)|^2))$, H is the Hilbert transform, and $a_1$ and $a_2$ are constants. In the image domain, $W_{i,j}(n)$ is a steered beam pattern that varies in beam width and steering direction for every channel data sample (e.g., for every range). $A_{thresh}$ controls the beam width of the back projected data. Using thresholding to define the beam widths enables beam widths on the order of a few degrees to be used for high SNR signals with presumably reliable estimates of DOA. In the channel data domain $W_{i,j}(n)$ is a weight specific to each piece of data summed to create an image pixel value, which can be seen in Eq. 24.

For display purposes, all images receive a small amount of post-processing and are then converted to a dB scale. The post processing step is defined as:

$$I_{display} = 20\log_{10}\left(G\left(\frac{|I \circ CF|}{\max(|I \circ CF|)}\right)\right) \quad (27)$$

where G is a 2D Gaussian filter and ○ is the Hadamard product.

The process structure is outlined in FIG. 21. The DOA estimation is executed in parallel on a quad core 3.5 GHz CPU, and the image reconstruction is executed on an Nvidia TitanX GPU with 12 GB RAM. All code is developed in Matlab 2016a (MathWorks, 2016), and CUDA (NVDDIA, 2018) kernels are written for GPU portions of the code.

Methods—Synthetic Data Set

Figure 22:
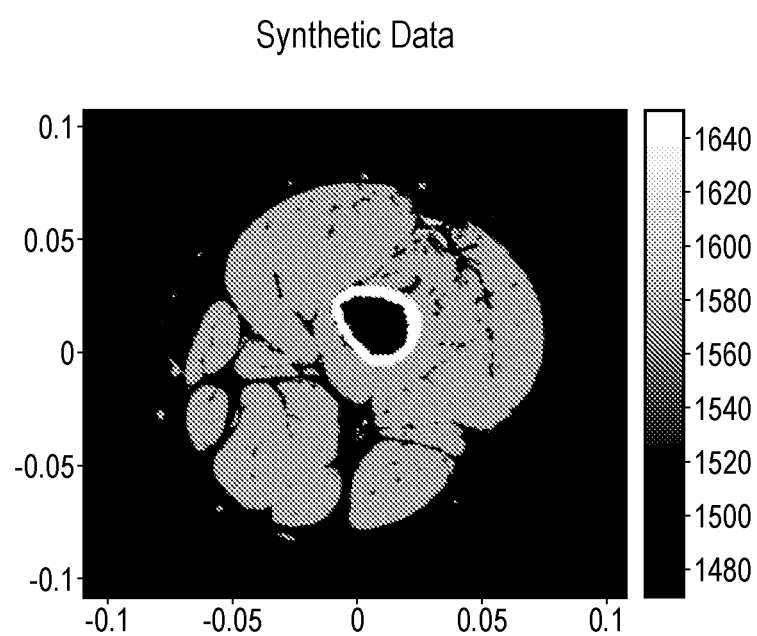
FIG. 22 is a graph of sound speed distribution within a numerical phantom.
Figure 23A:
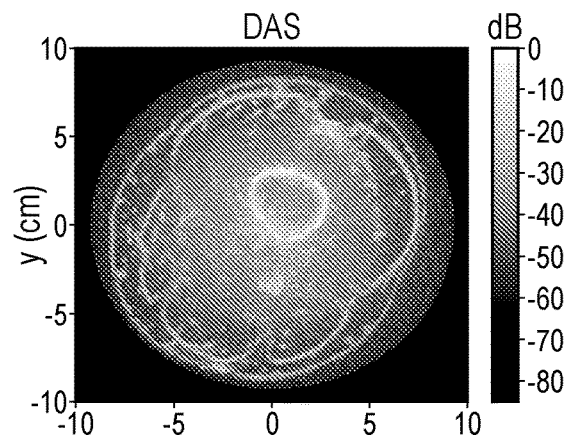
FIGS. 23A-D are ultrasound images of a numerical phantom. The images show bone, muscle, and vessels in the medium.
Figure 23B:
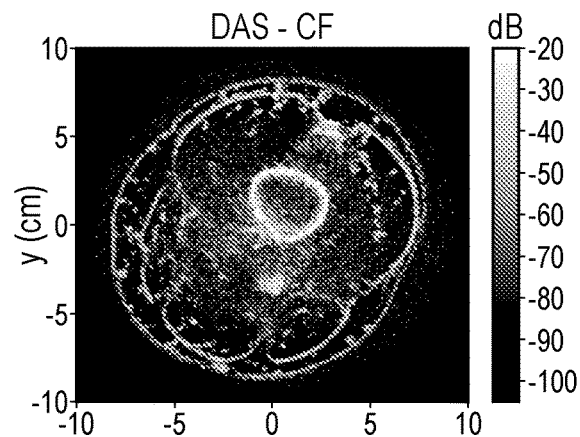
Figure 23C:
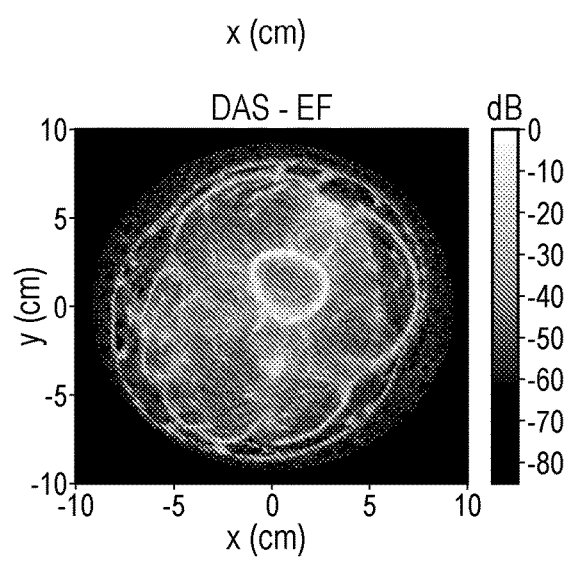
Figure 23D:
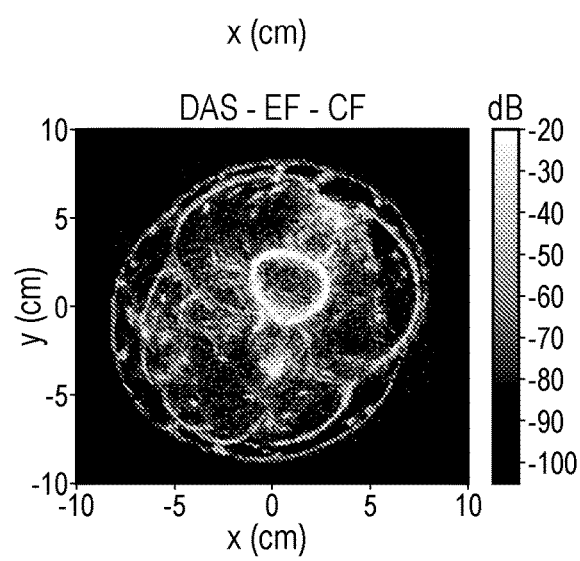

Synthetic test data is generated using the Matlab-based k-wave simulation toolbox. Calculation of the synthetic data set occurs on a 0.2165 m by 0.2165 m two-dimensional (2D) domain with 512 grid points in each dimension. The simulation includes the effects of sound speed, c, in units of m/s, density, ρ, in units of kg/m³, and attenuation, a, in units of dB/(cm-MHz). Shear wave effects are not simulated. Each synthetic data set consists of 1533 transmits spaced 0.235° apart along a 0.1 m radius circular array (FIG. 20). The array also contains 600 pressure sensors equally distributed along its circular aperture that record 62 µs time series (FIG. 20). The numerical phantom mimics a human thigh in water (FIG. 22). The geometry of the phantom is derived from the visible human project, and the sound speed, density, and attenuation values are taken from the literature. White noise is added to all of the data sets to mimic the signal to noise ratio (SNR) of data collected in a scanning tank.

Methods—Observational Data Sets

The observational data sets are collected on a nylon thread phantom, two bovine shanks purchased from a butcher, and a human forearm. Committee on animal care (CAC) and IRB approval were obtained for the ultrasound and MRI scans of the bovine shanks and human subjects. Monostatic scans are performed on the thread phantom, bovine shanks, and human arm. Bistatic scans are performed on the bovine shanks (Tables 1 and 2). MRI scans of the bovine shanks and human arm were done using a Siemens 3T scanner with 2 echo ultra-short echo-time (UTE) sequences and an abdominal coil wrapped around the target area of interest. Imaged targets, frequency used, and radial distance of the transducer from the center of the tank for the monostatic experimental data are shown in Table 1. Imaged targets, frequency used, and radial distances of the source and receive transducers for the bistatic experimental data are shown in Table 2.

TABLE 1

Monostatic experimental data monostatic data

| target | Frequency (MHz) | # of slices | $R_{tx}(m)$ |
|---|---|---|---|
| thread phantom | 2.25 | 1 | 0.1135 |
| beef shank 1 | 1.0 | 1 | 0.1143 |
| beef shank 2 | 2.25 | 1 | 0.1138 |
| arm | 5.0 | 1 | 0.1138 |

TABLE 2

Bistatic experimental data bi-static data

| target | Frequency (MHz) | # of slices | $R_{tx}(m)$ | $R_{rev}(m)$ |
|---|---|---|---|---|
| beef shank 1 | 1.0 | 1 | 0.1143 | 0.1016 |
| beef shank 2 | 1.0 | 1 | 0.1135 | 0.1078 |

Results

The images generated using the DAS with EF and a CF show SNR, in some cases, similar to typical US imagers and improved SNR relative to traditional DAS techniques in all cases examined. Sidelobe interference levels are significantly reduced. The reduction is significant for targets close to the bone and for strongly scattering objects in the bulk soft medium. The computation time required to generate the images is modest, taking a few minutes per image depending upon the frequency of the transducers, domain size, and hi-static versus mono-static image reconstruction. All images generated (using DAS, DAS with a CF, DAS with EF, and DAS with EF and a CF) are displayed on a dB gray scale. The gray scale range is 85 dB, but the minimum and maximum values vary between images in order to facilitate better comparison between processes.

Results—Monostatic Synthetic Data

The monostatic synthetic data set is generated by simulating the model shown in FIG. 22. The ultrasound images generated from the synthetic data set show the large sound speed gradient areas in the numerical phantoms (FIGS. 23A-23D). The EF process has the largest dynamic range compared to the other techniques employed (FIGS. 23A-23D). The sidelobe energy from the stronger scatterers is significantly reduced, which can be seen in the reduction of the noise floor and the enhanced contrast of the soft tissue features. The SNR, calculated by comparing a patch of the image with a strong signal to a patch with low signal shows the DAS with a CF process provides the best performance, as summarized in Table 3.

Results—Monostatic Experimental Data

Experimental data from a nylon thread phantom, two bovine shanks, and a human forearm comprise the experimental data set. The images generated from the observational data exhibits the same trends as the synthetically generated 2D data set for the monostatic and bistatic acquisitions.

Figure 24:
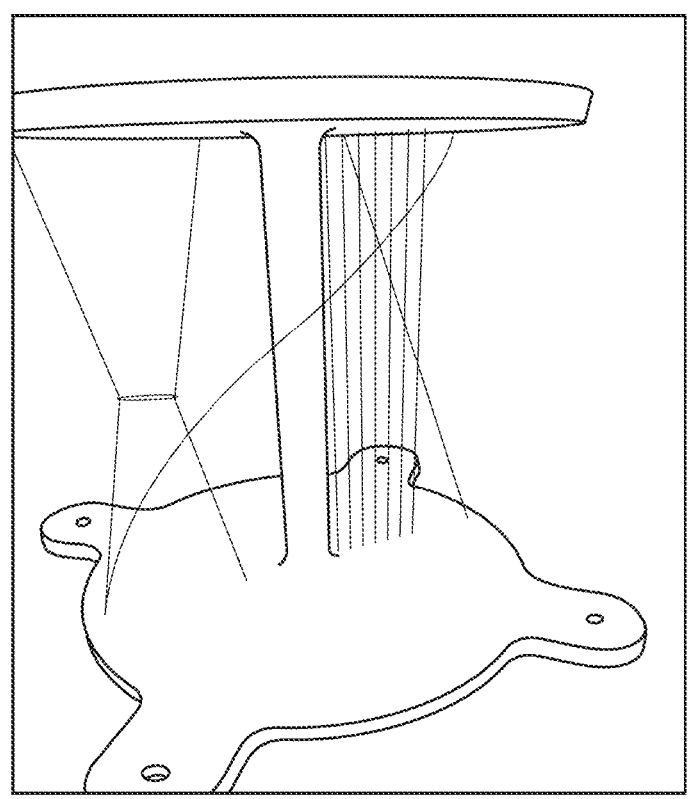
FIG. 24 is an image of a thread phantom including seven 0.762 mm diameter threads evenly spaced 6 mm apart radially from the center of the phantom. Another three nylon threads are 0.6 mm in diameter.

The thread phantom (FIG. 24) is constructed from 3D printed plastic with an array of small holes on the top and bottom surface. The holes allow threading of seven vertically oriented 0.762 mm diameter nylon threads evenly spaced 6 mm apart radially from the center of the phantom (FIG. 24, to the right of the post). An additional three 0.6 mm diameter Nylon threads are arbitrarily positioned with varying range from the central post as function of height (FIG. 24, to the left of the post). The smaller diameter threads are intended to approximate point scatterers.

Ultrasound images constructed from data acquired via a monostatic scan using a 2.25 MHz transducer are shown in FIGS. 25A-25D). Image generation is performed with each of the following methods: DAS, DAS with a CF, DAS with EF, and DAS with EF and a CF. The image reconstructed with DAS, EF, and a CF has the largest dynamic range compared to the other techniques.

Table 3 shows the SNR on connective tissue structures from the imagery. The areas of the computation are not shown on the imagery for clarity. Table 4 shows the time to reconstruct images using the DAS with a CF and EF technique as well as the approximate number of data samples and image pixels involved in the image reconstruction.

TABLE 3

Signal-to-Noise Ratio (SNR) on connective tissue structures

| algorithm | Numerical phantom | thread phantom | bovine sample 1 (1.0 MHz) | bovine sample 2 (2.25 MHz) | human arm (5.0 MHz) | bovine sample 1: bi-static (1.0 MHz) |
|---|---|---|---|---|---|---|
| DAS SNR (dB) | 11 | 13 | 18 | 16 | 15 | 11 |
| DAS CF SNR (dB) | 13 | 44 | 32 | 23 | 25 | 16 |
| DAS EF SNR (dB) | 27 | 57 | 46 | 43 | 40 | 22 |
| DAS EF CF SNR (dB) | 21 | 75 | 49 | 51 | 46 | 34 |

TABLE 4

Image reconstruction time

| Acquisition type | Frequency (MHz) | DOA estimation (s) | Image reconstruction (s) | Pixels | Data samples |
|---|---|---|---|---|---|
| monostatic | 1.0 | 129.5 | 13 | 1.50E+06 | 3.10E+06 |
| monostatic | 2.25 | 129.5 | 2.45 | 6.10E+06 | 3.10E+06 |
| monostatic | 5.0 | 556.8 | 9.3 | 3.70E+07 | 1.55E+07 |
| bi-static | 1.0 | 9324 | 5.92 | 1.50E+06 | 2.79E+07 |

Figure 25A:
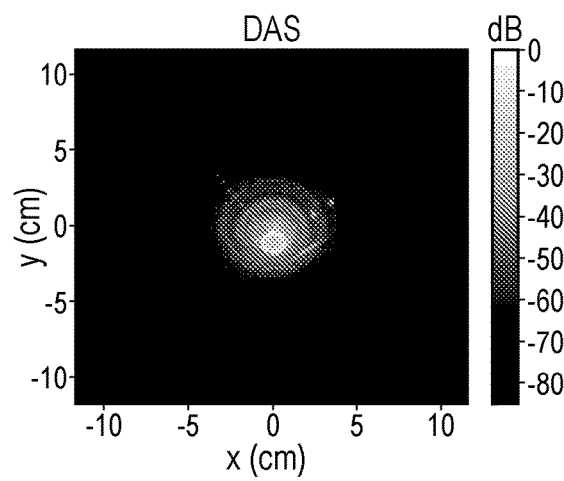
FIGS. 25A-D are ultrasound images of the thread phantom of FIG. 24. The images show the post in the center of the phantom and the threads of the phantom.
Figure 25B:
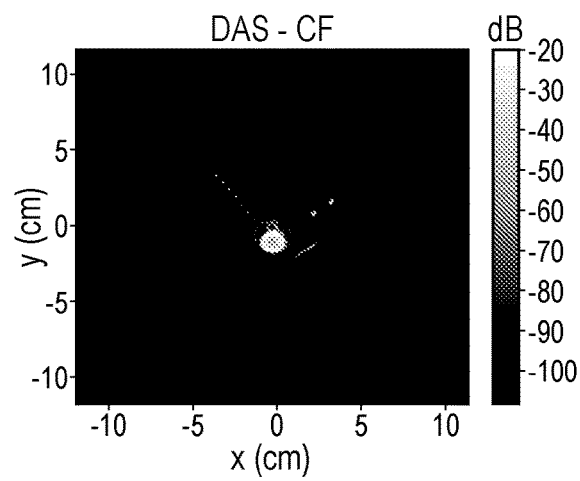
Figure 25C:
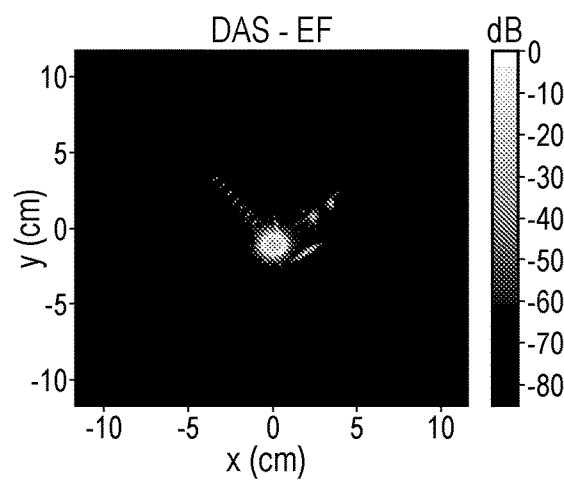
Figure 25D:
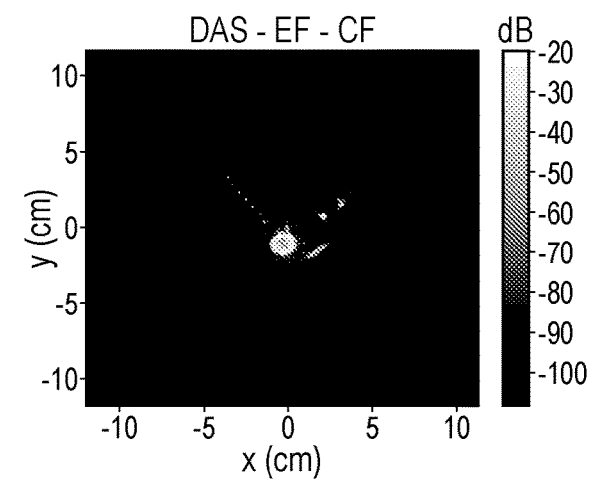
Figure 25E:
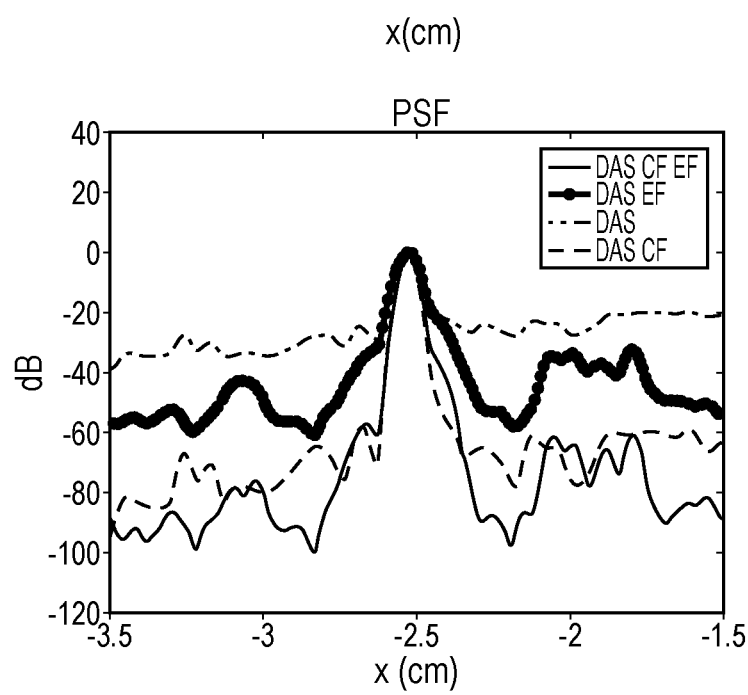
FIG. 25E is a graph of a normalized cross-section at y=2.43 cm of FIGS. 25A-D highlighting the preservation of spatial resolution, as well as noise floor and sidelobe interference reduction using DAS with a CF and EF.

The local SNR of the images at the 5th thread from the center of the phantom (located at 10:30 in FIGS. 25A-25D) is 13 dB, 57 dB, 44 dB, and 75 dB for the DAS, DAS with a CF, DAS with EF, and DAS with a CF and EF images, respectively (Table 3). A cross-section at y=2.43 cm of FIGS. 25A-25D shows the spatial profile PSF for the thread (FIG. 25E). The noise floor is reduced by approximately 60 dB using the EF and CF techniques (FIG. 25E) relative to DAS alone. The spatial resolution is only slightly worse using the EF and CF together relative the CF alone (FIG. 25E). The total image creation time for each image of the thread phantom is 131.95, seconds, including the DOA estimation (Table 4).

Figure 26:
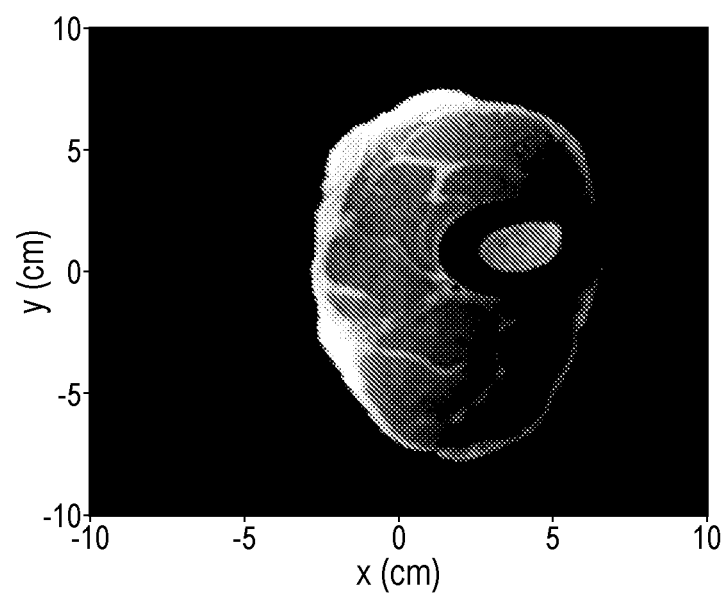
FIG. 26 is an MRI image of a first beef shank ("beef shank 1" or "bovine shank 1") taken from the same slice as the ultrasound images in FIGS. 27A-D. The MRI is from a 3T scanner using Ultrashort Echo Time (UTE) sequences and a body coil.
Figure 27A:
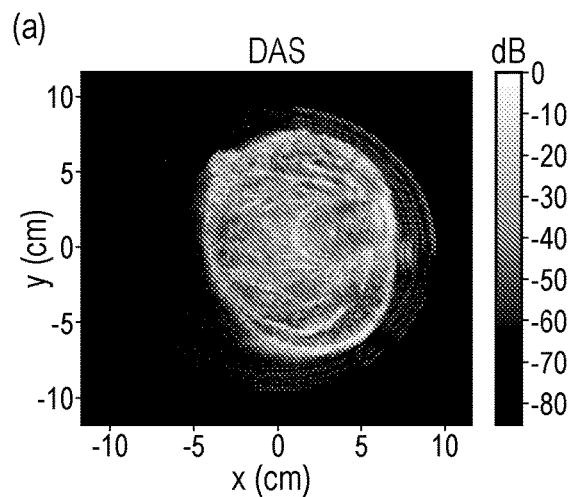
FIGS. 27A-D are ultrasound images of beef shank 1. The images show the bone in the center of the image and connective tissue and fat regions.
Figure 27B:
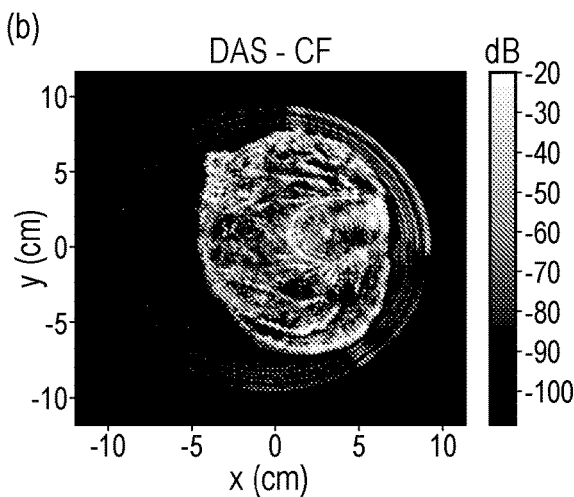
Figure 27C:
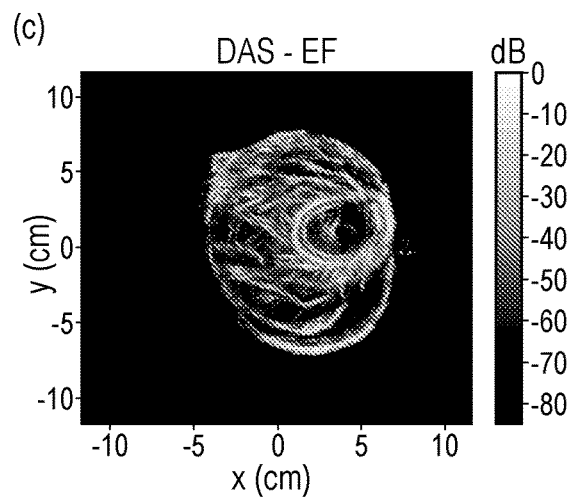
Figure 27D:
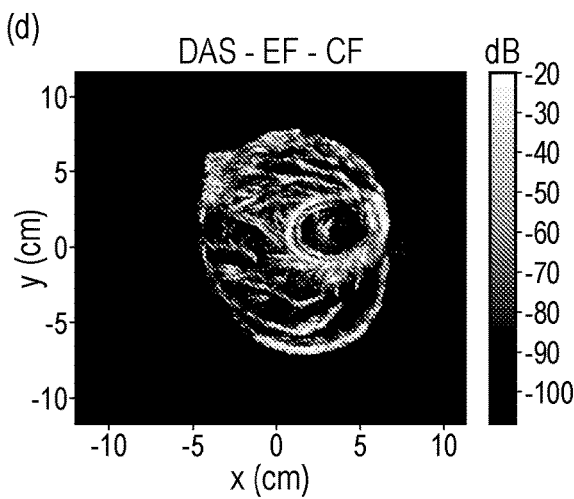
Figure 30A:
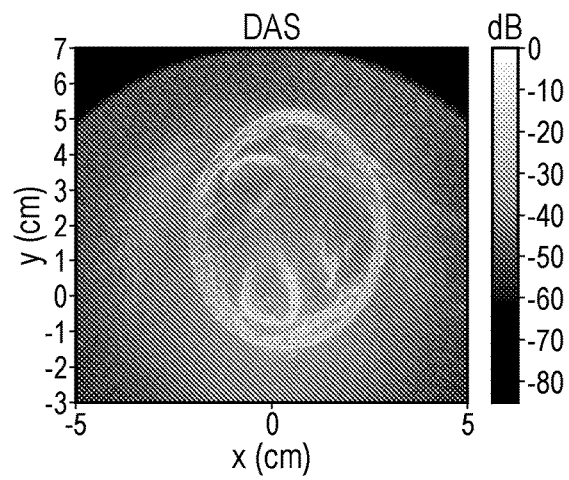
FIGS. 30A-D are ultrasound images of the human forearm of FIG. 29. The images show the long bones in the center of the image and connective tissue, fat, skin, and blood vessel regions. The x and y ranges of the images are 10 cm, half of the previous images in FIGS. 28A-D.
Figure 30B:
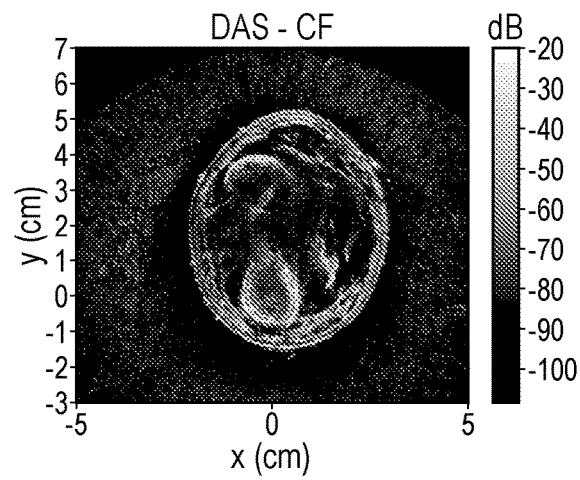
Figure 30C:
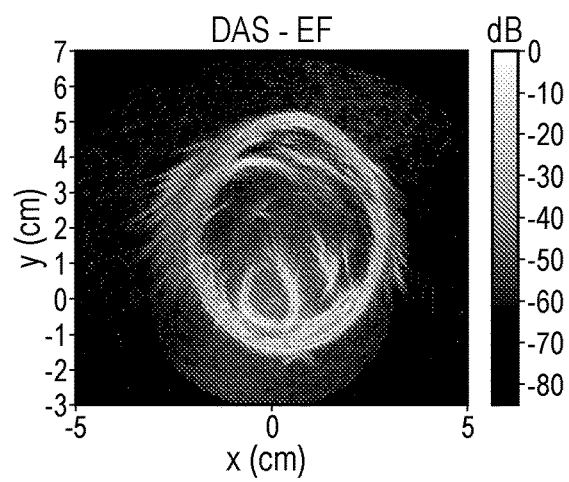
Figure 30D:
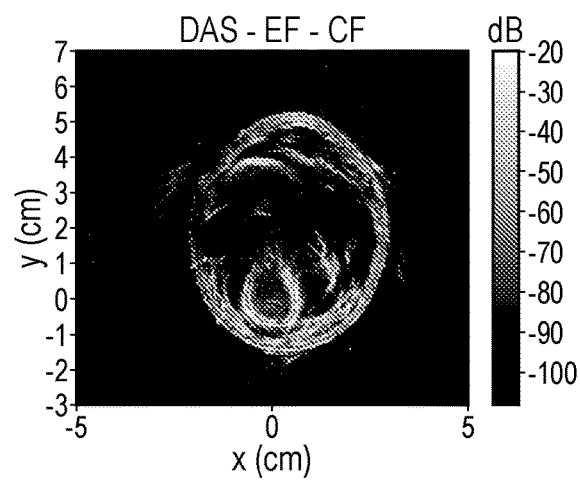
Figure 31A:
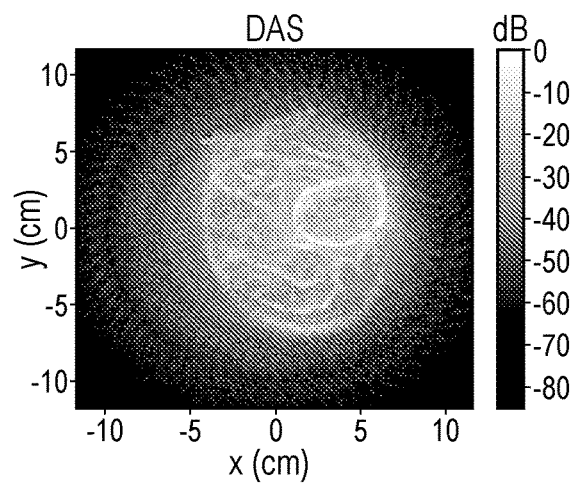
FIGS. 31A-D are ultrasound images of bovine shank 1, obtained with bistatic data. The images show the long bone in the center of the image and connective tissue, fat, skin, and blood vessel regions.
Figure 31B:
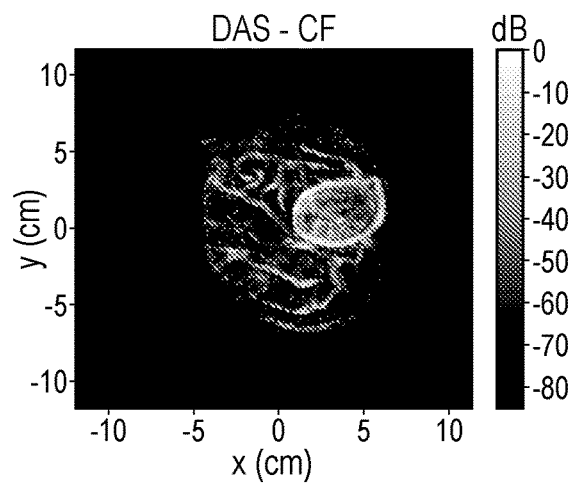
Figure 31C:
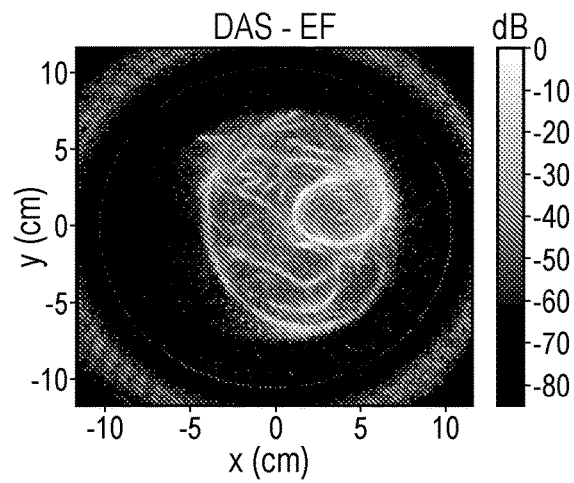
Figure 31D:
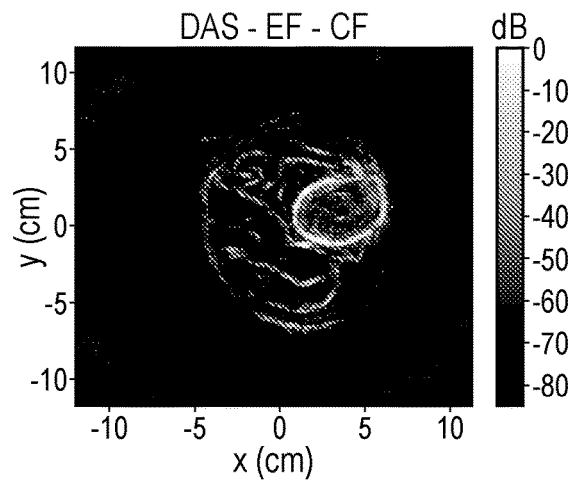
Figure 33A:
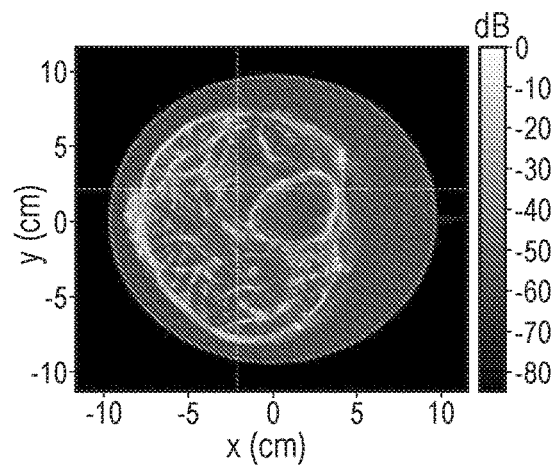
FIGS. 33A-D are volumetric images of beef shank 2 constructed from data collected with a 2.25 MHz transducer using a DAS-EF-CF process.
Figure 33B:
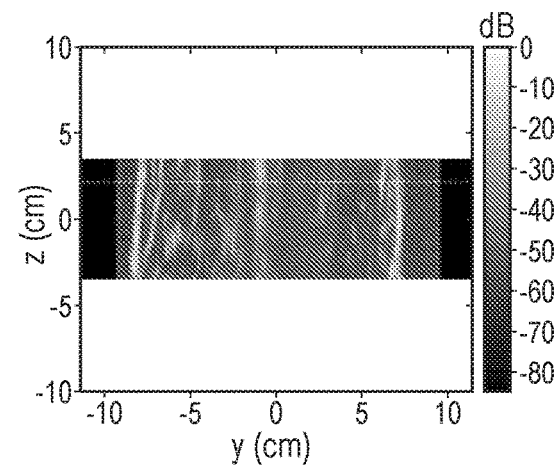
Figure 33C:
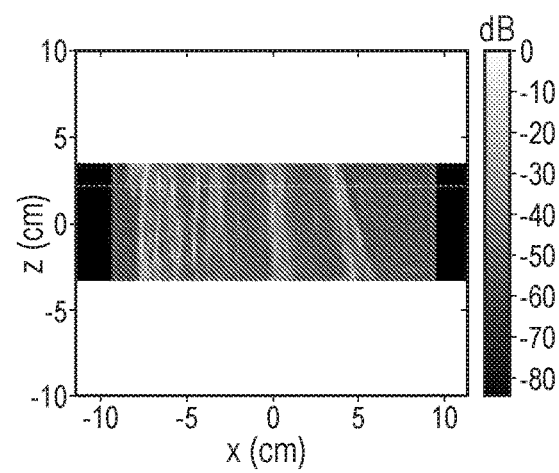
Figure 33D:
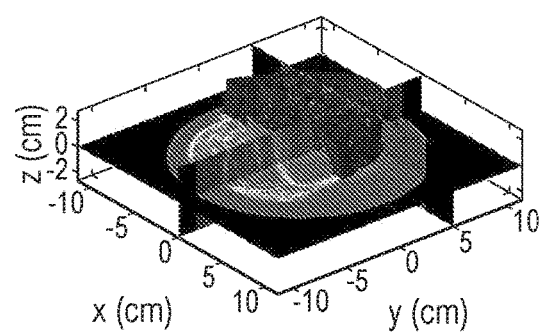
Figure 34A:
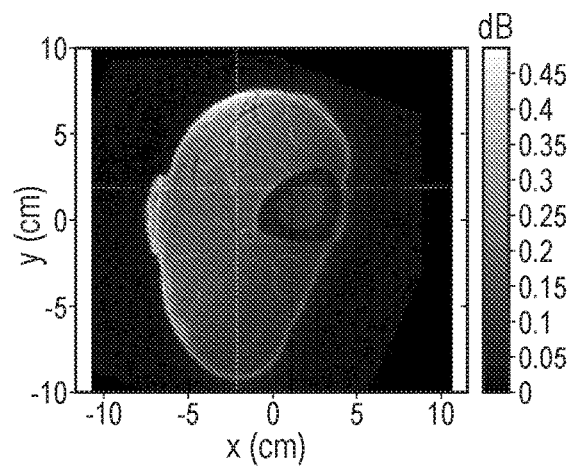
FIGS. 34A-D are volumetric MRI images of beef shank 2.
Figure 34B:
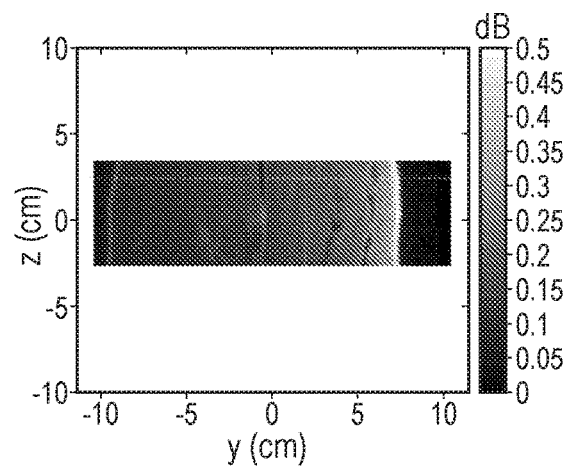
Figure 34C:
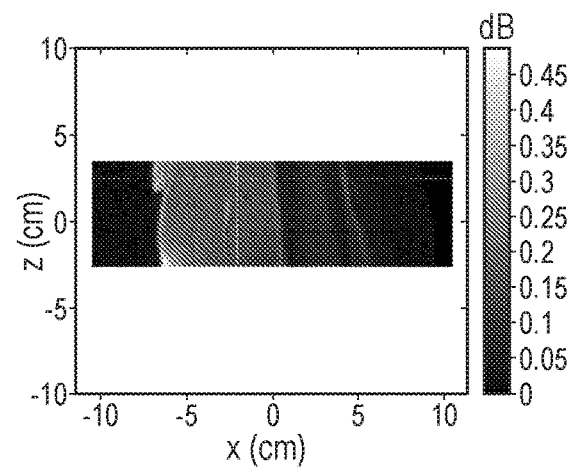
Figure 34D:
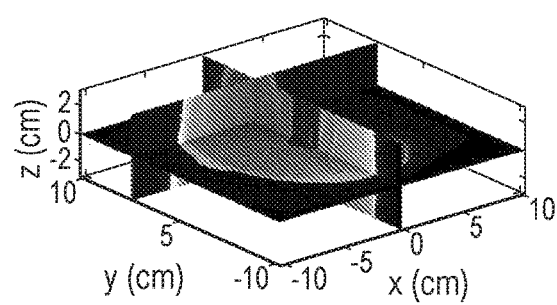

Bovine shank 1 (FIG. 26) is comprised of a single long bone with marrow inside, muscle fat, connective tissue within the muscle, tendons, and blood vessels. There is no skin or hair on the specimen. Soft tissue comparisons between the MRI image (FIG. 26) and the ultrasound images cannot be made directly since the tissue deformed between the ultrasound and MRI scans. Additionally, the ultrasound and MRI images are sensitive to different physical properties of the sample.

Ultrasound images constructed from monostatic scan data with a 1.0 MHz transducer are shown in FIGS. 27A-27D. Image constructions use the following methods: DAS, DAS with a CF, DAS with EF, and DAS with EF and a CF. Calculations of SNR on a section of the connective tissue shows the DAS with EF and a CF performs best by this metric, with the DAS with a CF having a 3 dB lower SNR (Table 3). Although the DAS and CF method has only slightly worse performance in SNR in this case, it still suffers from significant artifacts from the stronger scatterers, such as the bone, present in the imaging domain (FIGS. 27A-27D). The total image creation time for each image of shank 1 is 130.8 seconds, including the DOA estimation (Table 4).

Bovine shank 2 is comprised of a single long bone with marrow inside, muscle fat, connective tissue within the muscle, tendons, and blood vessels. There is no skin or hair on the specimen.

Ultrasound images constructed using monostatic scan data from a 2.25 MHz transducer are shown in FIGS. 28A-28D. Image generation transpires using the following methods: DAS, DAS with a CF, DAS with EF, and DAS with EF and a CF. The image reconstruction using DAS, EF and a CF has the largest SNR on the connective tissue (Table 3) and fewer artifacts present in the non-tissue regions of the image (FIGS. 28A-28D). The total image creation time for each image of shank 2 is 131.95 seconds including the DOA estimation (Table 4).

The human forearm (FIG. 29) is from a healthy volunteer, and the long bones, marrow, muscle, fat, connective tissue within the muscle, tendons, and blood vessels are all visible. Similar structures are visible in the ultrasound imagery as well (FIGS. 30A-30D).

Ultrasound images constructed using monostatic scan data from a 5.0 MHz transducer are shown in FIGS. 30A-30D. Image generation transpires using the following methods: DAS, DAS with a CF, DAS with EF, and DAS with EF and a CF. The image reconstruction using DAS, EF and a CF has the largest SNR on the connective tissue area analyzed (Table 3) and lower noise in the non-tissue and tissue regions. The complete perimeters of the bones are not fully reconstructed in any of the ultrasound images. This is likely due to specular reflection from the bone surface out of the x-y plane, which go un-detected using a 2D data acquisition approach but can be captured with a modified scanning approach. It is also possible specular reflections in the x-y plane are to blame, but the monostatic scanning approach does not capture these reflected waves. The total image creation time for each image of the arm is 566.1 seconds, including the DOA estimation (Table 4).

Results—Bistatic Data

Ultrasound images of bovine shank 1 (FIG. 26) constructed using 1.0 MHz data from a bistatic scan are shown in FIGS. 31A-31D). The images are acquired from the same plane as the images in FIGS. 27A-27D for the monostatic reconstruction. Image generation uses bi-tatic versions of the DAS, DAS with a CF, DAS with EF, and DAS with EF and a CF methods. The image reconstruction using DAS, EF and a CF has the largest SNR on the connective tissue area analyzed (Table 3) and lower noise in the non-tissue and tissue regions (FIGS. 31A-31D). The total image creation time for each image of shank is 9329.92 seconds including the DOA estimation (Table 4).

Results—Volumes from 2D Slices

A volumetric image of the thread phantom, with a second set of threads with small knots added, is constructed by applying the DAS-EF-CF process (with less aggressive beam steering than the 2D examples described above) to 50 monostatic scans each spaced 0.64 mm apart in the vertical using a 1.0 MHz transducer. The final volume (FIGS. 32A-32D) is constructed by interpolating between the 2D images from the scans. The threads, as well as the central post of the phantom and the threads knots, are resolved.

A volumetric image of beef shank two is constructed by applying the DAS-EF-CF process (with less aggressive beam steering than the 2D examples described above) to 22 monostatic scans each spaced 3.18 mm apart in the vertical using a 2.25 MHz transducer. The final volume (FIGS. 33A-33D) is constructed by interpolating between the 2D images from the scans. The bone and soft tissue structure is resolved, yielding information on bone and connective tissue geometry. The MRI image volume (FIGS. 34A-34D) reveals qualitatively similar tissue geometry compared to the ultrasound image volume. The soft tissue geometries are not expected to be identical because the tissue was deformed between the ultrasound and MRI scans.

DISCUSSION

An adaptive beamforming technique for imaging tissues with bone inclusions using single element or array USCT systems is shown to generate ultrasound images of soft tissue and bone with similar SNR to conventional ultrasound imagers. The EF technique uses the direction of arrival information and a coherence factor to reduce sidelobe artifacts in the ultrasound image and reduces the overall image noise floor. The technique is tested on numerical data, phantoms, animal tissue, and human tissue in-vivo. The method is particularly useful for imaging domains where both weak and strong scatters are to be imaged.

These techniques can have significant impact for applications where low-cost and high-resolution volumetric (e.g., by collecting multiple slices) imagery is desired, such as in prosthetic fitting and muscle status monitoring.

Extending the method to 3D as well as speeding up the DOA estimation via a GPU implementation can enable volumetric ultrasound images of bone and soft tissue in clinically useful time scales with a single transducer.

Example 4. Ultrasonic Quantification of Bone and Soft Tissue Sound Speed and Geometry Using Travel Time Tomography with Geometric Regularization from Pulse Echo Imagery The geometry and sound speed of bone, soft tissue, and water are estimated using an ultrasound travel time tomography inversion process on data collected from a cylindrically scanning, non-contact, immersion-based ultrasound tomography system. The technique successfully estimates bone and soft tissue sound speeds by using travel time measurements and pulse echo images to define the geometry of the underlying sound speed distribution. The process performance is demonstrated on a numerical data set and experimental data sets collected on beef shanks purchased from the butcher. Significant algorithmic and measurement challenges are associated with generating clinically useful pulse echo and sound speed images of bone and soft tissue. These challenges stem from the sound speed and density values in bone being approximately double that of the surrounding tissue and attenuation that can be an order of magnitude greater than soft tissue. Bone material properties and geometry decrease the SNR of direct arrivals through bone, shadow or overpower other scatterers in pulse echo images, and specularly reflect wavefronts out of the imaging plane. The process and data acquisition approach presented here successfully overcomes many of these issues.

The large changes in sound speed and density between soft tissue and bone leads to strong reflections that can shadow or overwhelm other anatomical regions of interest in pulse echo imaging, as well as significantly alter the arrival of reflected signals. In terms of travel time measurements and inversions, the presence of bone significantly degrades the SNR of the first arrival due to strong attenuation in the bone and reflections at the bone interfaces. The large sound speed and density changes at the bone interface also create strong refractions to be accounted for. The smooth surface of most bone tissue can also generate out of plane specular reflections leading to loss of signal in both backscatter and through transmission measurements.

In quantitative ultrasound (QUS), single measurements in space of travel time, frequency dependent attenuation, and backscatter coefficients can yield path averaged estimates of bone properties, such as sound speed and attenuation. Ultrasound tomography techniques can, in theory, reconstruct the sound speed, density, and attenuation distributions of the underlying medium. Such an approach may provide more accurate estimates of physical parameters, as well increase repeatability of measurements.

Inversion techniques using ray tracing with travel times, or, more recently, full waveform inversion (FWI) have been employed to recover quantitative ultrasound images of sound speed and attenuation. Studies using ultrasound to image and quantify bone have relied on ray-based travel time or Born approximation inversion schemes on simple bone samples. FWI techniques come with substantial computation costs and are prone to converge to local minima (i.e. are not globally optimal solutions).

In this study, a ray-tracing-based travel time inversion technique is employed to estimate bone and soft tissue sound speed on numerically generated and experimentally obtained data sets. In the case of the numerical data set, the numerical phantom mimics a human femur. The experimental data sets are collected on beef shanks purchased from the butcher using cylindrically scanning ultrasound tomography. The inversion technique successfully estimates bone and soft tissue sound speeds and geometry by using travel time measurements and pulse echo images. This work expands on previous attempts to quantitatively image soft tissue and bone with ultrasound by combining travel time inversion techniques with pulse echo imagery in an iterative process. Additionally, the process is demonstrated to successfully generate quantitative ultrasound images on multiple intact samples of biological tissue containing soft tissue and bone.

Methods—Simulated Data Sets

Synthetic data generated using the MATLAB (Mathworks, Natick, Ma, USA) based k-wave simulation toolbox constitutes the synthetic data set. Calculation of the synthetic data set occurs on a 0.2165 m by 0.2165 m two-dimensional (2D) domain with 512 grid points in each dimension. The simulation includes the effects of sound speed, c, in units of m/s, density, $\rho$, in units of $kg/m^3$, and attenuation, a, in units of dB/(cm-MHz). Shear wave effects are not simulated. Each data set consists of 1533 transmits with a 1.0 MHz center frequency spaced 0.235° along a 0.1 m radius circular array. The array also contains 600 pressure sensors equally distributed along its circular aperture, which record 124µs time series (FIG. 20). The numerical phantom mimics a human thigh in water. The geometry of the phantom is derived from the visible human project. The sound speed, density, and attenuation values are taken from the literature for both phantoms. White noise is added to all of the data sets to mimic the signal to noise ratio (SNR) of data collected in the scanning tank, and Gaussian position error, similar to scanning tank performance, is added to the source and receiver positions.

Methods—Experimental Setup

The experimental data collection is completed using a custom-made, dual-transducer, cylindrically-scanning immersion ultrasonic tomographic scanner (see, for example, FIG. 1). Both transducers can be independently positioned over the entire 360° aperture and translate ~7 cm vertically for acquiring multiple 2D slice or volume images of a target and enabling iterative development of scanning procedures. The two transducers are also removable, allowing testing of transducers with varying beam properties and frequency. Further details describing the general mechanical and electrical design of the system can be found in Zhang et al., 2015.

The data acquisition system consists of a low frequency pulser (DPR300, Imaginant, Pittsford, Ny, USA) that drives the transmitting transducer and has an analog receive front end for the receiving transducer (which can be the same as the transmitter). The analog signal coming from the pulser is digitized at 50 MHz (NI PXie-1073, National Instruments, Austin, TX, USA) and streamed to a PC where the signal is saved for processing. Further details general describing the data acquisition system can be found in Zhang et al., 2015.

Monostatic and bistatic scans are employed to collect the experimental datasets. The monostatic scan consists of sequentially recording 1533 pulse-echo channel data lines at 1533 locations equally spaced 0.23450 apart around the tank, resulting in a full 3600 synthetic aperture. For these scans, 1.0 MHz broadband, custom-made, cylindrically-focused transducers are employed that produce a 650 full beam width fan beam pattern.

The bistatic scan consists of 72 transmit locations equally spaced 5° apart, resulting in a 360° synthetic aperture. At each transmit location, 1333 channel data lines are sequentially acquired from the receiving transducer at 1333 equally distributed spatial locations (0.2345° apart), resulting in a 313° receive aperture. A full 3600 receive aperture was not obtained due to mechanically interference of the mounting brackets with each other, resulting in 23.5° of the circular aperture on either side of the source bracket not being accessible to the receiver. When constructing images from the bistatic data, the channel data from positions 23.5°-58.5° from the source location are used. For these scans, 1.0 MHz broadband, custom-made transducers are employed. The source transducer is the same design as those used for the bistatic scans. The receiving transducer is a 1.47 mm diameter disk shaped receiver, which is nearly a point receiver at 1.0 MHz.

The source transducers were measured with a calibrated hydrophone to ensure that the scans do not exceed the food and drug administration (FDA) standards for ultrasound use on humans. All scanning procedures described were approved by the MIT committee on animal care.

Methods—Inversion Technique

The inversion technique consists of several integrated processes, operating on the observed data set, to yield a sound speed distribution of the target in the tank. Central to the inversion technique is a travel time tomography method, which is used to estimate sound speed distribution of the target in the tank from measured travel times. The technique presented here differs from traditional travel time tomography techniques by implicitly regularizing the travel time inversion with the geometry of the target derived from pulse echo images. The inversion method is iterative, and, at each iteration, the target is re-imaged using the updated sound speed distribution, and the geometric constraints are updated with the new images. The process runs until a set number of iterations are reached or an error tolerance is met.

Travel Time

The travel times are picked using the Akaike Information Criterion (AIC) and a matched filter to find the peak of the first arrival. The AIC is a quantitative criterion for picking a model that describes a process that will minimize the information loss by choosing a particular model for the process. The AIC is repeated here for clarity:

$$AIC(k)=k\log(\text{var}(S(1,k)))+(N-k-1)\log(\text{var}(S(k+1,N))) \quad (28)$$

where k is the time index, log is the natural logarithm, var is the variance, S is a single time domain trace, and N indicates the size of the sliding analysis window.

The AIC value is calculated using equations from Li, et al., "An improved automatic time-of-flight picker for medical ultrasound tomography," Ultrasonics, 49, 61-72 (2009) (see Equations 1 and 2 in Li, et al.). The minimum in the AIC value indicates the arrival of a signal. Once the arrival of the signal is estimated, a 2.0*F μs window for the matched filter is defined starting at the first arrival point, where F is an empirical SNR-dependent multiplicative factor. The value of F is typically ~2 for arrivals that travel through soft tissue or water and ~1 for arrivals that travel through bone.

A half period 500 kHz sine wave multiplied in time by a Hanning window is convolved with the window of data to remove noise and find the peak of the first arrival. The frequency of the matched filter is chosen to match the expected frequency content of the first arrival. The first arrival through bone is expected to predominantly contain the lowest transmitted frequency due to dispersion and smaller impact of attenuation at lower frequencies. It has been shown that the low frequency data arrives first in laboratory experiments.

Inversion Model

The inversion for the sound speed distribution occurs by solving the system of linear equations:

$$d=Gm \quad (29)$$

for m, where d is the travel time data generated by the travel time picker, G is a matrix describing the path of the received signal through the domain, and m is the slowness (1/c) distribution within the domain. Rays connecting each receiver to each source are calculated to create G. The rays are calculated by solving the eikonal equation via a wave front tracking program, and wavefronts are converted to rays after each simulation by following the normal to the first arrival wavefront from each receiver back to the source.

The system in Eq. 29 is generally over determined, unstable, and does not have a unique solution. Solving the system in Eq. 29 for a physically plausible m distribution can require regularization of the problem.

In this study, the system in Eq. 29 is regularized by breaking the domain into discrete blocks, or segments of similar tissues or materials. The pulse-echo segmentations described above define the block regions. The blocks of the domain are inverted as single parameters in the inversion model. Such a block-wise inversion can be thought of as a "perfect" $L_1$ regularization because the formulation forces the solution to be made up of many piece-wise constant regions. The inversion is done by condensing the G matrix into a matrix called $G_{block}$ defined as:

$$G_{block_{i,b}} = \sum_{n=1}^{N_b} G'_{i,n,b}, \; i = 1 \ldots N_{ttm}, \; b = 1 \ldots N_{blocks} \quad (30)$$

$$G'_{i,f,b}=G_{i,j} \in B_b, \; b=1 \ldots N_{blocks} \quad (31)$$

where $N_b$ is the number of pixels within the $b^{th}$ block in the domain, $N_{ttm}$ is the number of travel time measurements, $N_{blocks}$ is the number of blocks into which the domain is split, and G' is a 3D matrix where the third index indicates the parts of G that describe travel paths through the $b^{th}$ block of the domain. In practice, G' does not need to be calculated but is included here to formally describe $G_{block}$. The cost function $C_b(m)$ for the block-wise inversion is given by:

$$C_b(m)=\|G_{block}m-d\|_2^2 \quad (32)$$

and is minimized via a gradient descent process.

Estimation of Initial Sound Speed Spatial Distribution

The block-wise technique described above can require an initial guess of the bone geometry and sound speed in the starting model because it implicitly regularizes the inverse problem using the geometry of the soft tissue and bone. Therefore, an initial soft tissue and bone geometry is estimated. By applying the synthetic aperture focusing technique (SAFT) to the data sets, a reflection image, similar to a conventional ultrasound image, results. A snake process segments the water-soft tissue boundary, as well as the outer boundary of bone in the image. Due to the difficulty with automatically segmenting the inner boundary of the bone, it is assumed the inner boundary has the same shape as the outer boundary but shrunk by 25%. The image segmentations allow the definition of bone and soft tissue regions in the initial sound speed distribution. Inserting literature values for sound speed in the block regions yields an initial starting model that accounts for the bone geometry and sound speed.

Inversion Process

The inversion scheme is iterative and starts using the initial sound speed map generated from the pulse echo data (see FIG. 35). During each iteration, Cb (m) is minimized using gradient descent, resulting in new estimates of m. The new model is fed into a sound-speed-compensating migration process to re-image the target with a better estimate of the sound speed distribution. The new image is automatically segmented, and the new in values are assigned to the newly segmented regions. The new sound speed distribution is passed to the next iteration of the process. For this work, four blocks define the sound speed map: water, soft tissue, bone, and marrow.

The process is run in Matlab on a 72-core computing cluster with 2.7 GHz clock rates (Sabalcore Inc., Melbourne, FL, USA). The pulse echo images are generated on 1000× 1000 grid point matrices, and the sound speed maps are computed on 806×806 grid point matrices. The main computational burden for the process is computing the travel time maps for each of the 1533 transducer positions. In total, the process completed in 30 minutes per iteration with the computational hardware employed. Since the major bottle neck is the pulse echo imaging, increasing the number of cores can decrease the time per iteration (e.g., computing more travel time maps in parallel).

Methods—Ground Truth Measurements

Figure 36A:
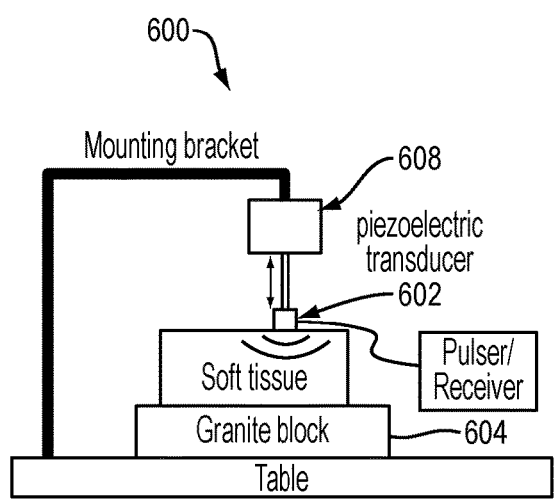
FIGS. 36A-B are schematics of experimental setups for measuring tissue ground truth sound speed.
Figure 36B:
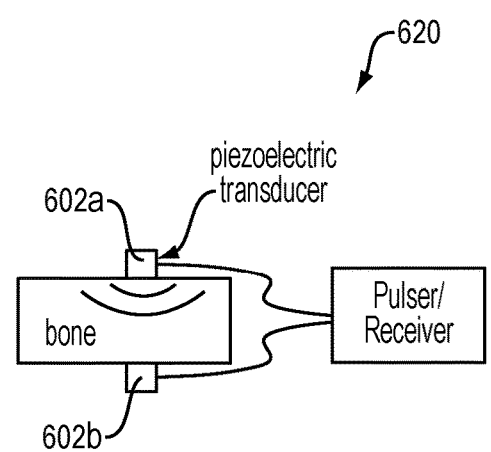

The velocity and geometry estimate from the observational data sets are compared to velocity estimates from tissue samples and MRI scans respectively. The ground truth velocity estimates are carried out using a micrometer (Starrett IP 67 2900, The L.S. Starrett Company, Athol, Ma, USA) and a pair of 9 MHz transducers (Olympus V1091, Olympus, Tokyo, Japan) (FIGS. 36A-36B). The same electronics from the tank system are used to send and receive signals for the ground truth measurements.

Two experimental setups are utilized to estimate the tissue ground truth sound speed. The first setup 600 uses a potentiometer 608 and a single transducer 602 (FIG. 36A) in reflection mode. The second setup 620 uses two transducers 602a, 602b in through transmission mode with a pair of calipers. The first setup is for measuring soft tissue sound speed, and the second setup is for measuring the bone sound speed. For soft tissue sound speed measurement, a sample 606 is placed between the transducer 602 and the granite block 604, and a pulse is sent through the sample. The reflection from the granite block 604 is detected at the transducer 602, and velocity is measured based on the distance of the transducer from the slab and the two-way travel time. The bone velocity is measured using two transducers, one on either side of the bone (FIG. 36B). The bone thickness is measured with a set of calipers (not shown), and the one-way travel time from the source transducer 602a to the receiving transducer 602b is the travel time. The sound speed of the water in the scanning tank is calculated using a temperature measurement from a thermometer with 0.01° F. resolution.

MRI scans of the beef shanks are done using a 3T scanner (Siemens Medical Solutions, Malvern, Pa, USA) with 2 echo ultra-short echo-time (UTE) sequences and an abdominal coil wrapped around the target area of interest. The shanks are lying down in the scanner but are upright when scanned with the ultrasound system. This difference in orientation should be noted when comparing MRI images to ultrasound images.

Results

Figure 37A:
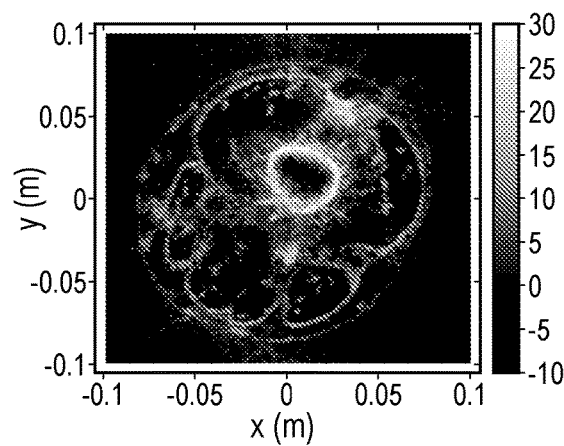
FIGS. 37A-B are pulse echo and sound speed images of a numerical phantom from first and last iterations of the process.
Figure 37B:
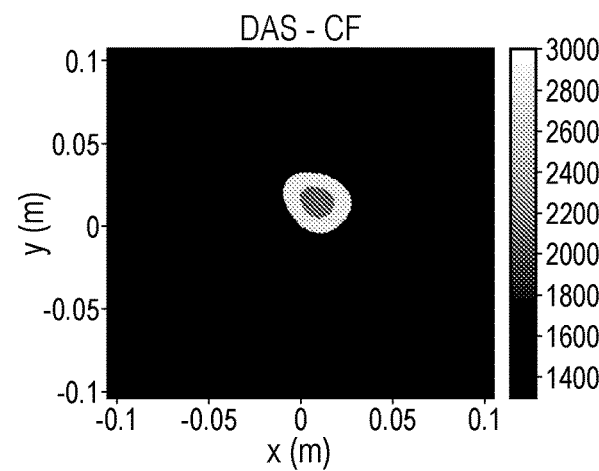
Figure 37C:
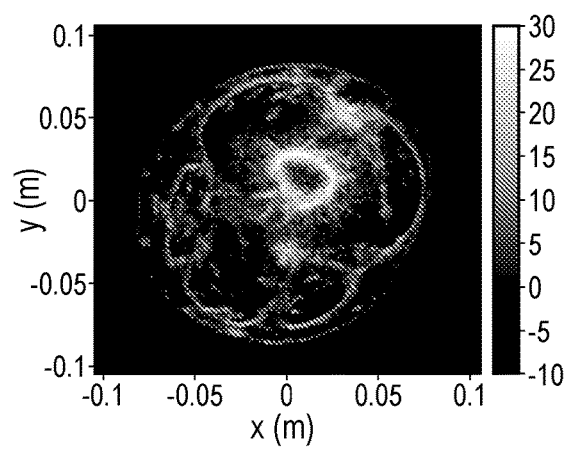
FIG. 37C is a pulse echo image from a final iteration generated by compensating for the sound speed distribution.
Figure 37D:
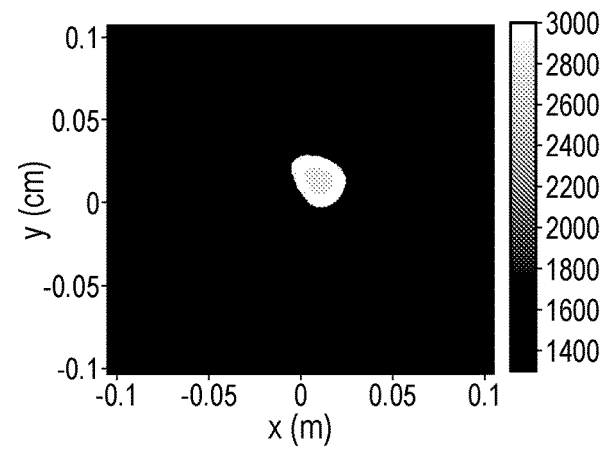
FIG. 37D is a sound speed distribution from the final iteration of the process with the geometry defined from segmentation of FIG. 37C. The greyscale bar is in m/s.
Figure 38A:
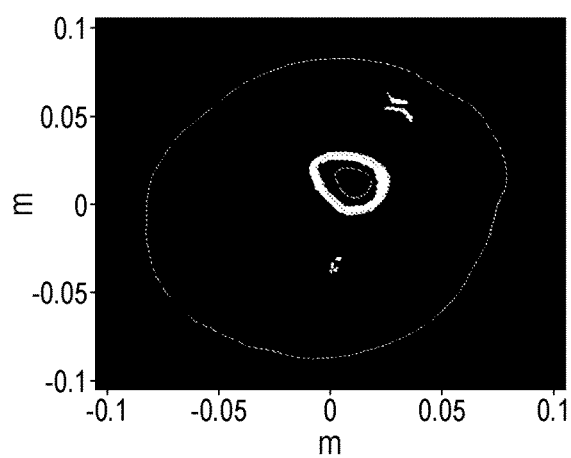
FIGS. 38A-38B illustrate final results of the inversion technique with the numerical phantom.

The experimental results consist of pulse-echo images, sound speed distributions, and ground-truth tissue sound speed observations, when available. The sound speed distributions are spatially defined by segmentation of the pulse echo imagery, and the velocity estimates are derived from the travel time observations described above. The results show sound speed accuracy between 2% and 10% for bone, soft tissue, and water. The velocity estimate in the marrow region is assumed to be unreliable, as described below Results—Human Femur Numerical Phantom The experimental results from the numerical data set show the process can estimate the geometry and sound speed of water, soft tissue, and bone. The pulse echo image from the first iteration of the process and resulting sound speed distribution from the image segmentation are shown in FIGS. 37A-B. The pulse echo image and resulting sound speed distribution from the last iteration of the process are shown in FIGS. 37A-B. The final segmentation overlaid on the ground truth sound speed distribution is shown in FIG. 38A, demonstrating that bone and soft tissue geometry is significantly improved from FIGS. 37A-B to FIGS. 37A-B.

Figure 38B:
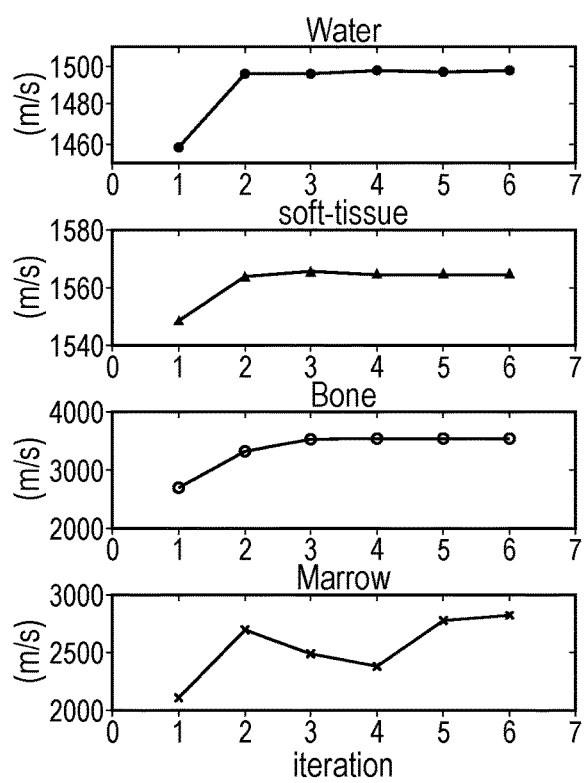

The sound speed estimates for each block region as a function of iteration number are shown in FIG. 38B. It appears the process converges to a velocity estimate for the bone, soft tissue, and water in three iterations. The error in the sound speed relative to the known sound speed distribution is shown in Table 5. All the velocity estimates are within 3% of the ground truth values except for the marrow.

TABLE 5

True and inverted sound speed and error for each tissue type inverted for in the domain.

| Material | True (m/s) | Inverted value (m/s) | Percent Error |
|---|---|---|---|
| Water | 1480 | 1499 | 1.2% |
| Muscle | 1580 | 1564 | 1.0% |
| Bone | 3460 | 3559 | 2.99% |
| Marrow | 1487 | 2378 | 90.4% |

Results—Beef Shank 1

Figure 39A:
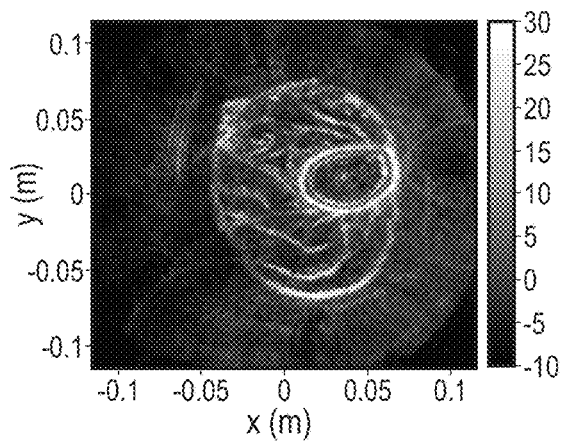
FIGS. 39A-39D are pulse echo and sound speed images of the first beef shank.
Figure 39B:
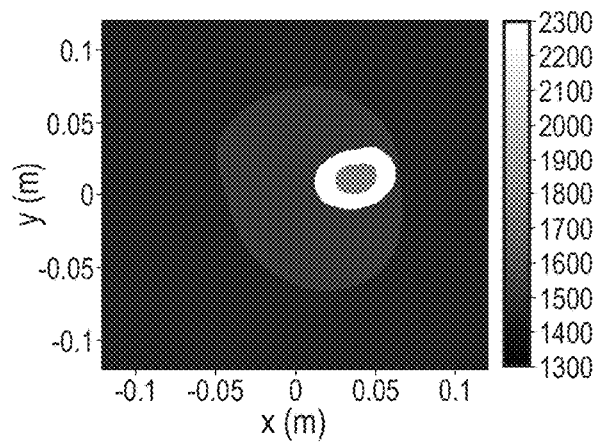
Figure 39C:
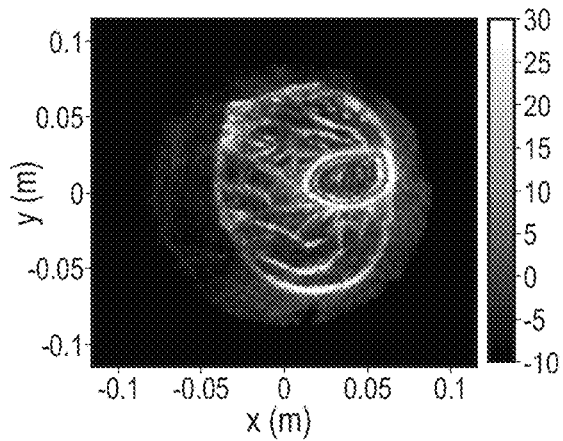
Figure 39D:
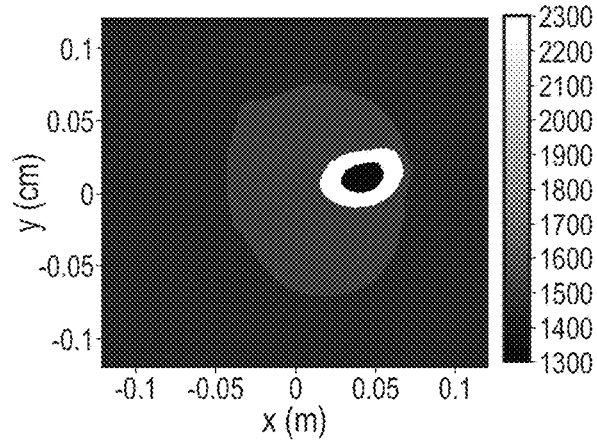
Figure 40A:
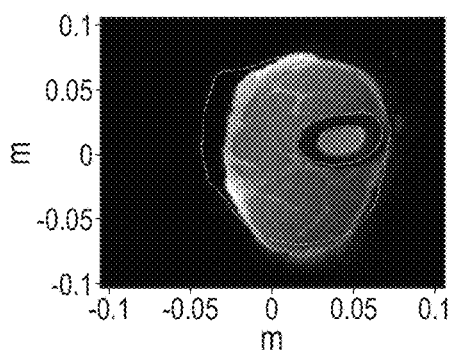
FIGS. 40A-40B illustrate final results of the inversion technique with the first beef shank.

The experimental results from the first beef shank show that the process can estimate the geometry and sound speed of water, soft tissue, and bone using data collected using a physical system. The pulse echo image from the first iteration of the process and the resulting sound speed distribution from the image segmentation are shown in FIGS. 39A-B. The pulse echo image and resulting sound speed distribution from the last iteration of the process are shown in FIGS. 39C-D. The final segmentation overlaid on the MRI of the beef shank is shown in FIG. 40A, demonstrating the bone geometry, and possibly the soft tissue geometry, is significantly improved from FIGS. 39A-B to FIGS. 39C-D.

Figure 40B:
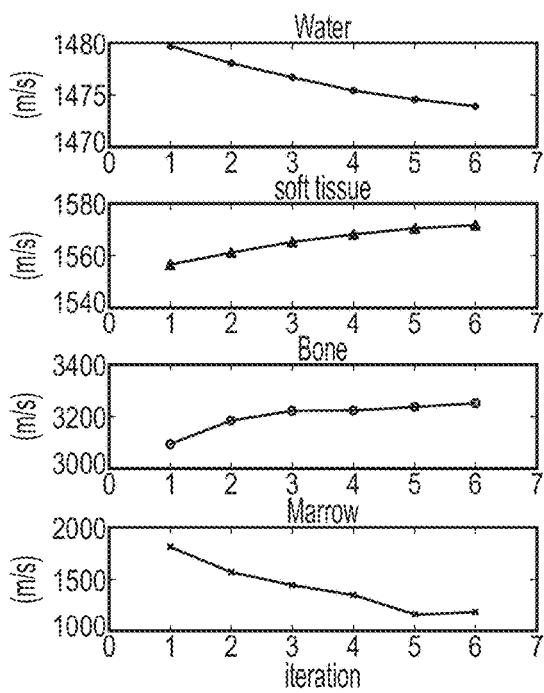

The sound speed estimate for each block region as a function of iteration number are shown in FIG. 40B. It appears the process converges to a velocity estimate for the bone, soft tissue, and water in six iterations. The error in the sound speed relative to the ground truth measurements of water and bone is shown in Table 6. All the velocity estimates are within 3% of the ground truth values, except for the marrow and soft tissue. Soft tissue ground truth sound speed is not shown because the sample was frozen before the ground truth measurement could be made. The bone ground truth measurement is made after the sample was thawed, but it is assumed it would affect the bone sound speed less. The marrow sound speed is not measured.

TABLE 6

True and inverted sound speed and error for each tissue type inverted for in the domain

| Material | True (m/s) | Inverted value (m/s) | Percent Error |
|---|---|---|---|
| Water | 1487 | 1475 | 0.8% |
| Muscle | — | 1568 | — |
| Bone | 3164 | 3220 | 1.8% |
| Marrow | — | 1359 | — |

Results—Beef Shank 2

Figure 41A:
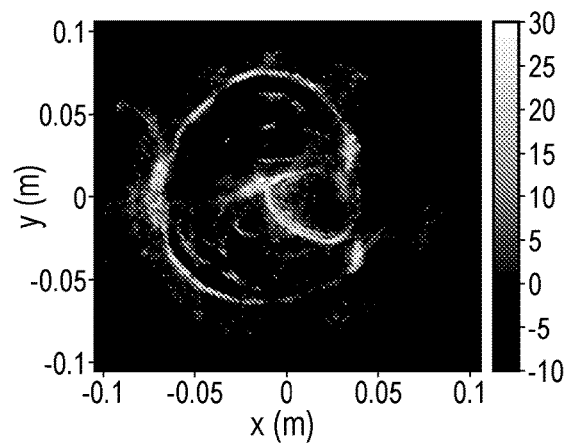
FIGS. 41A-D are pulse echo and sound speed images of the second beef shank.
Figure 41B:
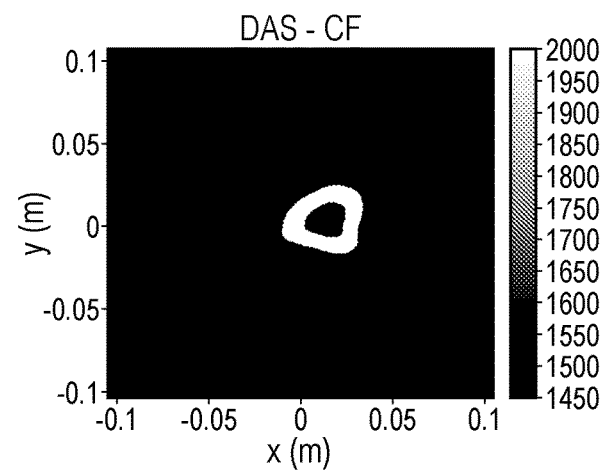
Figure 41C:
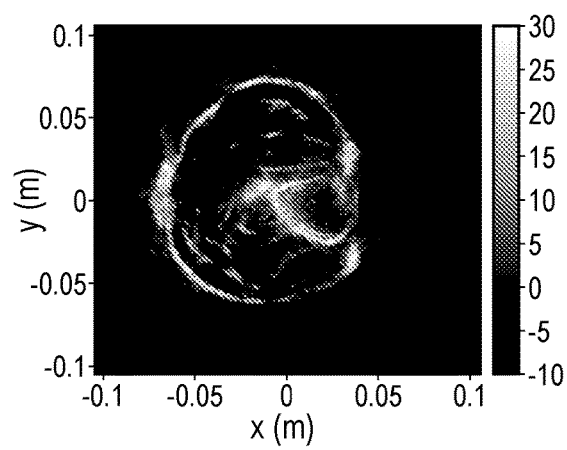
Figure 41D:
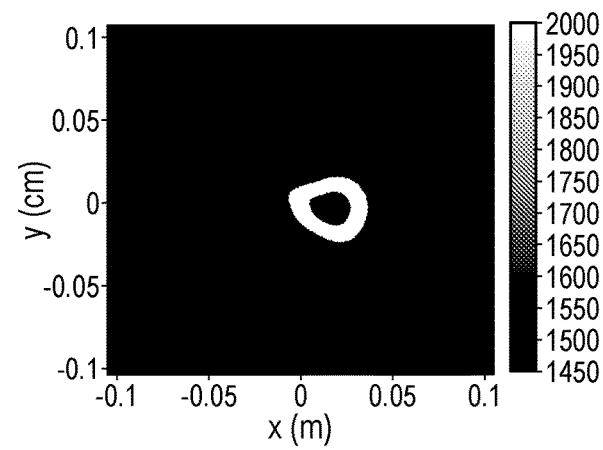
Figure 42A:
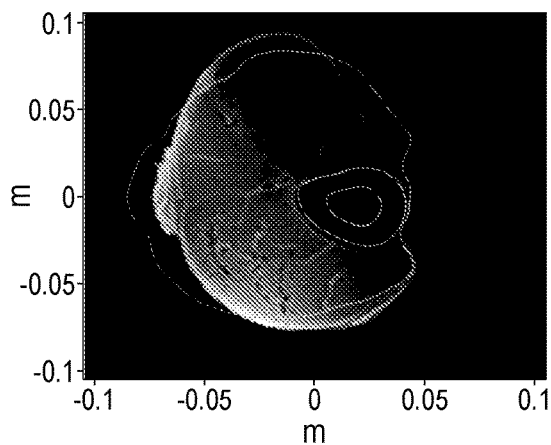
FIGS. 42A-42B illustrate final results of the inversion technique.

The experimental results from the second beef shank show additional evidence the process can estimate the geometry and sound speed of water, soft tissue, and bone from data collected using a physical system. The pulse echo image from the first iteration of the process and resulting sound speed distribution from the image segmentation are shown in FIGS. 41A-B. The pulse echo image and resulting sound speed distribution from the last iteration of the process are shown in FIGS. 41C-D. The final segmentation overlaid on the MRI of the beef shank is shown in FIG. 42A, demonstrating the bone geometry, and possibly the soft tissue geometry, is significantly improved from FIGS. 41A-B to FIGS. 41C-D.

Figure 42B:
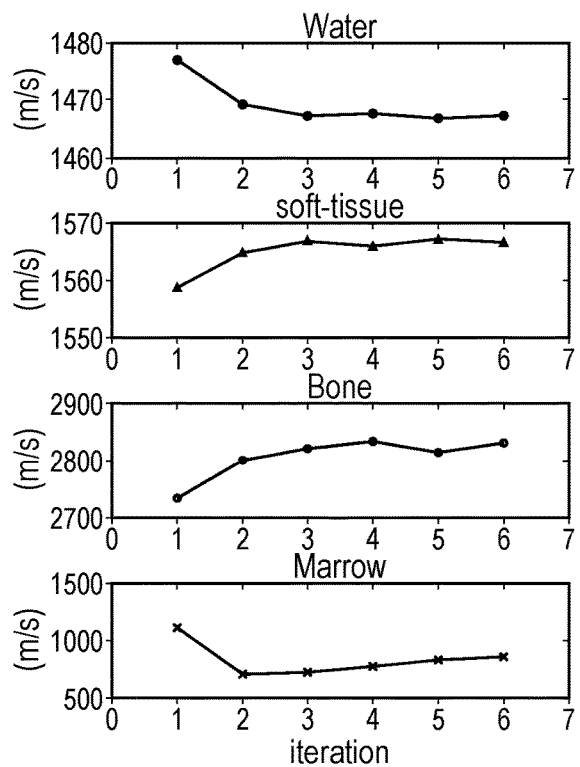

The sound speed estimates for each block region as a function of iteration number are shown in FIG. 42B. It appears the process converges to a velocity estimate for the bone, soft tissue, and water in five iterations. The error in the sound speed relative to the ground truth measurements of water, soft tissue (muscle), and bone is shown in Table 7. All of the velocity estimates are within 10% of the ground truth values except for the marrow. All ground truth measurements were made directly after scanning the beef shank.

The large error in the bone estimate is likely due to the poor segmentation of the bone for this sample. The upper right corner of the bone boundary is poorly resolved, which leads to a less accurate segmentation. The 3D MRI scan (not shown) shows the bone surface is tilted in this region, which means most of the energy from the incident wave reflected out of the imaging plane, resulting in low SNR for this portion of the bone boundary.

TABLE 7

True and inverted sound speed and error for each tissue type inverted for in the domain

| Material | True (m/s) | Inverted value (m/s) | Percent Error |
|---|---|---|---|
| Water | 1486 | 1467 | 1.3% |
| Muscle | 1574 | 1567 | 0.5% |
| Bone | 3147 | 2831 | 10.0% |
| Marrow | — | 862 | — |

Discussion

Figure 43A:
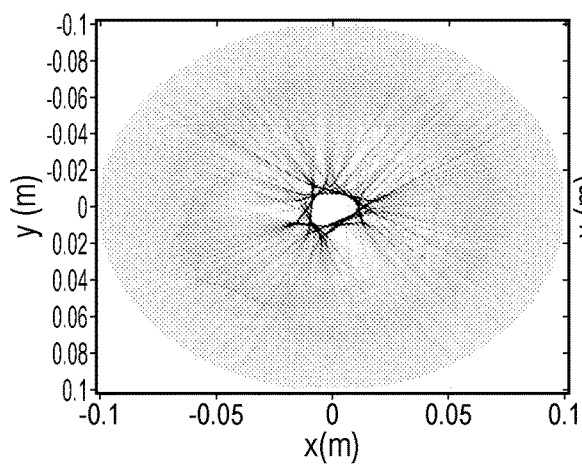
FIGS. 43A-43B illustrate sampling of a domain containing a single long bone by the first arrival rays.
Figure 43B:
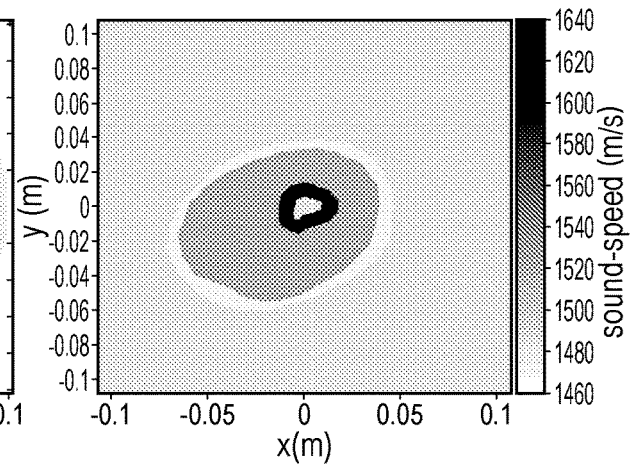

The results show the proposed technique reliably estimates the bone and soft tissue sound speed of biological tissues. In previous studies, conventional ultrasound tomographic inversion methods, such as ray tracing with Tikhonov regularization, were applied to estimating bone sound speed, but significant artifacts due to the high bone sound speed were unavoidable. These artifacts are due to biased sampling of high velocity regions in the inversion domain. In the case of bone, the majority of first arrival ray pass through the bone for any given transmit (FIGS. 43A-B). This over sampling may still occur with the proposed method herein; however, the spatial regularization eliminates the artifacts arising from the spatially biased sampling.

The presence of the bone also inhibits any estimates of the marrow sound speed using first arrival travel time tomography. Since ray tracing predicts the first arrival wavefronts, any wavefronts traveling through the bone will travel faster than those in the marrow. As a result, the marrow region of most long bones will not be sampled by a ray tracing technique, and this is shown by the absence of rays in the marrow region in FIGS. 43A-B. If the bone is small enough, however, it may be possible to sample the marrow region if the path through the marrow regions is sufficiently shorter than the path through the bone region.

The results show that the proposed method can estimate the bone, soft tissue, and water sound speed to within 2% of the true value. In addition to good accuracy, the method is found to be robust and does not suffer many of the convergence issues with full waveform inversion techniques. Applications for quantitative ultrasonic imaging of bone and soft tissue include muscle health monitoring, osteoporosis monitoring, prosthetic fitting and stress fracture detection and tracking.

Example 5. Ultrasonic Sound Speed Imaging of Cortical Bone and Soft Tissue with Level Set Spatial Regularization to Regularize Full Waveform Tomography Techniques: Results from Synthetic Data Sets Quantitative sound speed images of limb cross-section, bone, and soft tissue from synthetic data sets emulating an ultrasound tomography (UST) system are generated using full waveform inversion (FWI). Source encoding is coupled with level set regularization to resolve the sound speed images. A-priori information about the general structure of cortical bone provides an initial sound speed distribution. The FWI and level set techniques iteratively update the sound speed map to a final estimate of the domain properties and geometry. Results demonstrate the recovery of sound speed and geometry of cortical bone and soft tissue with modest computational cost. Bone imaging and quantification is of general clinical utility and is continuing to gain interest within the ultrasound research community. Applications for this work include prosthetic fitting, fracture detection and the diagnosis and monitoring of osteoporosis.

Medical ultrasound imaging processes and systems for simultaneous clinical imaging and quantification of hard and soft tissues, such as bone and muscle, can be applied to several applications, such as improving prosthetic fitting, muscle health monitoring, osteoporosis monitoring, and bone fracture detection. Techniques for imagining bone include travel time and full waveform inversion (FWI). Such techniques can produce quantitative images of tissue geometry and sound speed. These techniques can use both reflected and transmitted waves to infer the underlying sound speed and density distribution that gave rise to the observed data. The inversion problem is ill-posed and nonlinear, making it difficult to solve. The collection of reflected and transmitted acoustic waves motivate a departure from the traditional linear and convex ultrasound probes to ultrasound computed tomography systems that surround the volume of interest with ultrasound transducers.

Tomographic inversion techniques can be applied to data sets collected from ultrasound tomography systems to generate clinically meaningful images of soft tissues. Photoacoustic tomography can also be applied for soft tissue imaging. The ultrasound tomography and photoacoustic tomography studies primarily focus on producing clinically relevant images of breast tissue for breast cancer detection. For breast tissue, modest sound speed and density variations on the order of 50 m/s and 50 kg/m$^3$ are typical. In contrast, inversion techniques that produce clinically useful images in parts of the body with bone inclusions have significant algorithmic and measurement challenges due to the large sound speed and density variations, for example, changes of 1700 m/s and 850 kg/m$^2$ at bone-soft tissue interfaces.

Techniques relying on path averaged sound speed and attenuation have been used for quantification of cortical and calcaneus bone. The path averaged techniques may not compensate for bone geometry as well as source and receiver positioning relative to the bone. Improvements in ultrasound imaging and quantification of bone material properties can be made through improved modeling of the propagation physics, acquisition of larger and more controlled data sets, and constraint of inversions with a priori information. A promising imaging process for bone, when coupled with adequate observational data, is FWI because it inherently handles reflected and transmitted waves, as well as strong scattering.

FWI is a non-linear optimization technique that attempts to minimize the difference between an observed time series and a time series generated synthetically from a model of the acquisition domain (the model data). An error between the observed and synthetically-generated time series, or cost function, is reduced by updating the model to make it more closely approximate the actual domain from which the observed data is collected. A variation of FWI based includes employing an adjoint technique to calculate a gradient of the cost function with respect to model parameters. Calculating the gradient of the cost function using the adjoint of the wave field can require two simulations on the model per transmission used in the data acquisition. In a data acquisition where hundreds or thousands of transmissions are completed, the FWI technique can require significant computational resources and time.

Source encoding is a method for reducing the computational cost of FWI. The method works by encoding and adding the observed data from each transmit together, creating a single encoded observational data set with only one transmit, and then running the FWI process with this single-transmit observational data set. Source encoding is attractive because it allows the gradient of the cost function to be computed with just two simulations of the data acquisition wave field, while using the entire observed data set, which can contain hundreds or thousands of transmissions. Therefore, source encoding can dramatically reduce the computational resources and time for generation of useful images using the FWI technique.

FWI convergence and numerical stability is reduced by strong impedance objects within the observational domain. Level set methods are proposed for image and quantification of bone properties with ultrasound.

In this study, the forward problem of data collection is numerically simulated, similar to previous studies. Then, the inverse problem of sound speed image generation is resolved using FWI with source encoding coupled with level set techniques, a departure from previous methods for using FWI to image bone sound speed. Sound speed is resolved instead of density or attenuation because sound speed alters the time of arrival of waveforms, whereas density and attenuation variations mostly impact the amplitude of waveforms. The sound speed model is updated to align the waveforms to reduce the cost function as cycle skipping can lead to convergence to a local minimum. A-priori information regarding the general structure of cortical bone is included to generate the initial sound speed distribution. The results demonstrate the feasibility of the proposed method for recovery of sound speed and geometry of cortical bone with modest computational resources and time. Further, the proposed technique yields more accurate geometry and sound speed images compared to conventional FWI methods for negligible increases in computational cost.

Methods—Simulated Data Sets

Synthetic observed data is generated using the MATLAB based k-wave simulation toolbox. Calculation of the observed data sets occurs on a 10 cm by 10 cm two-dimensional (2D) domain with 1024 grid points in each dimension ($\Delta x=\Delta y=0.1016$ mm). The simulation includes the effects of sound speed, c, in units of m/s, density, $\rho$, in units of kg/m$^3$ and attenuation, a, in units of dB/(cm-MHz) (FIGS. 44A-D). Shear wave effects are not simulated. This choice is made because energy at the receivers in the converted waves is expected to be significantly lower than the compressional waves.

Figure 44A:
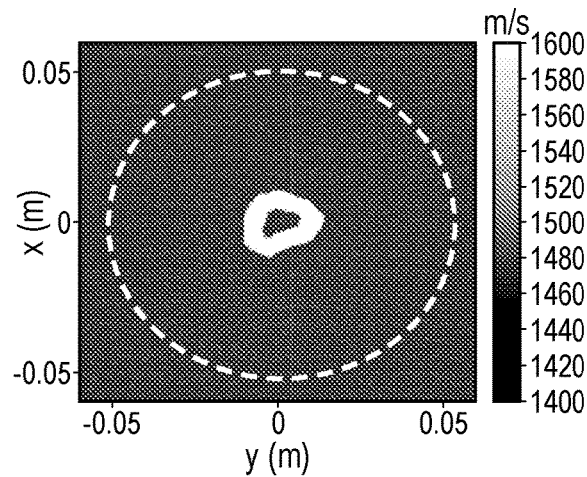
FIGS. 44A-44D illustrate sound speed distributions for two numerical phantoms employed in a study.

Each observed data set consists of 72 transmits spaced 5 degrees apart along a 5 cm radius circular array (FIG. 44A). The array also contains 418 velocity sensors equally distributed along its circular aperture which record 60 μs time series ($\Delta t=8$ ns).

Figure 44B:
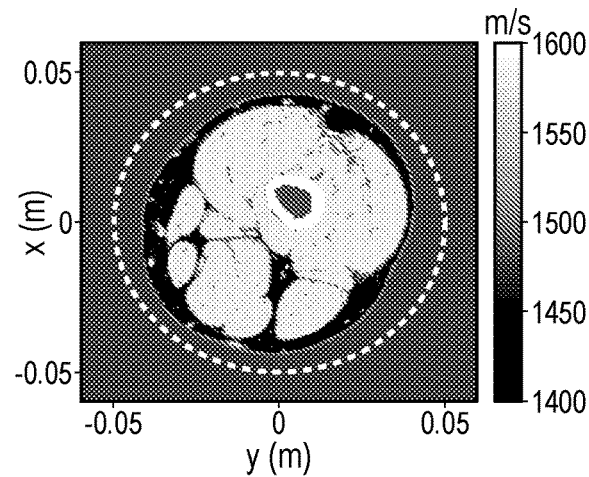

Two numerical phantoms are tested (FIGS. 44A-D). The first phantom mimics a single long bone in water (FIG. 44A), and the second phantom approximates a 12 year old child-sized femur and surrounding tissue in water (1.8 cm diameter femur) (FIG. 44B). The geometry of the second phantom is derived from the visible human project, and the sound speed, density and attenuation values are taken from the literature for both phantoms. It is known that bone properties change over the thickness of the cortical wall, but that the velocity in the bone region is constant and set to 3450 m/s as a simplifying assumption. The phantoms are transverse slices of bone where it is expected the compressional wave velocity is nearly isotropic since the slice is perpendicular to the Haversian canal and osteon structures.

Noise is added to the observed data to more closely emulate data from a physical ultrasound tomography system. The addition of white noise to the synthetic data melds a ~30 dB signal to noise ratio, replicating similar signal to noise ratio of experimental data collected on an ultrasound tomography system in the laboratory. Random+/−0.03 cm position error is added to the source and receiver positions. Lastly, the inversion takes place on a 256×256 grid, smaller than the simulated data, to model the impact of simulating wave propagation and using the same solver to generate the data set and complete the inversion. Ultimately, the data set consists of 72 transmits, each with 418 receives, and each receiver records 1800 time samples, yielding ~6.2×10$^6$ observations of the domain. Using a 256×256 inversion grid, there are ~6.6×10$^4$ unknowns in the inversion. The over sampling of the domain is done to compensate for the non-linear and ill-posed nature of this inverse problem.

Methods—Inversion Technique

The FWI techniques attempt to reconstruct the spatial distribution and value of physical parameters that give rise to the observed time series data (e.g., pressure, velocity, and/or displacement). In this study, the experimental time series is the numerically generated data with the added noise sources. The reconstruction is achieved by minimizing the difference between the experimental time series and modeled time series generated by numerical simulation. The FWI technique minimizes the objective function, shown as Eq. 1 above, and a variation of which is as follows:

$$E(c, \rho) = \frac{1}{2}\sum_{n=1}^{N} \|u(c, \rho, s_n) - d_n\|^2 - \|c - c_0\|^2 \qquad (33)$$

where E is the mean square error between the observed and modeled data plus the difference between the current model and the a priori expected model $c_0$, u is the wave equation operator that outputs a modeled time series of velocity with units of m/s, $s_n$ is the source for the $n^{th}$ transmission, $d_n$ the observed time series data from the $n^{th}$ transmission with units of m/s, and $\beta$ is a scalar weighting factor. The second term in Eq. 33 is a regularization term and is omitted in the remainder of this section for brevity. The gradient of Eq. 33 with respect to c for a single source can be found in the literature and is given by:

$$\frac{\partial E}{\partial c} = \frac{2}{c^3}\sum_{n=1}^{N}\int_{0}^{T}\frac{\partial p_n}{\partial t} p_n^*(t - T)dt \qquad (34)$$

where p is the recorded pressure with units of Pa, p* is the adjoint pressure field, and T is the duration of the observed time series. The pressures $p_n$ and $p^*_n$ can each require a wave equation solve, and as such, 2N solves of the wave are needed to compute $\partial E/\partial c$. Eq. 33 can be rewritten to enable the use of a stochastic gradient descent technique called source encoding as:

$$E(c, \rho) = \frac{1}{2}\left\|\sum_{n=1}^{N}u(c, \rho, e_n \otimes s_n) - \sum_{n=1}^{N}e_n \otimes d_n\right\|^2 \qquad (3)$$

where $e_n$ is a random encoding sequence and $\otimes$ is the convolution operator. Here, $e_n$ is randomly assigned to be −1 or 1 for each transmission, and $e_n$ changes each iteration of the gradient descent process, similar to previous studies. The computational burden of FWI typically scales linearly on the number of sources which, for ultrasound tomography, can reach many thousands in number. Source encoding, however, makes the computational cost of FWI independent of the number of sources used in an experiment by combining all observed data and transmits into a data set containing one encoded transmit. The reduction in computational expense comes at the cost of only approximating $\partial E/\partial c$ at each step in the inversion. If enough iterations are run, however, the integrated effect of applying $\partial E/\partial c$ from source encoding can yield a nearly identical result as traditional FWI techniques.

In this study, for simplicity, the inversion algorithms use binary values for $\rho$, 1050 kg/m³ for soft tissue and 1500 kg/m³ for bone. A regularization term is often added to Eq. 33 and 3, such as a roughness penalty, but in this study, the level set method implicitly regularizes Eq. 33.

The level set method defines a distance function Ø (FIG. 45A) from a contour or contours and allows the contour(s) (and Ø) to evolve as "forces" act on the contours' surfaces. In this case, the level set function defines the bone regions and non-bone regions of the domain and defines the c and ρ distributions in the following way:

$$c(x,y) = c_{bone}H(\emptyset) + (1 - H(\emptyset))c_{soft}(x,y) \qquad (4)$$

$$\rho(x,y) = \rho_{bone}H(\emptyset) + (1 - H(\emptyset))\rho_{soft} \qquad (5)$$

where x and y are the spatial coordinates of the domain, and H is the Heaviside function (FIG. 45B). Locations in the domain where Ø>0 bone properties are given to that piece of the domain and where Ø<0 the domain is soft tissue. The term $c_{soft}(x,y)$ is expressed explicitly as a function of x and y to highlight that its values change from grid point to grid point, in contrast to $c_{bone}$, which takes a single value over the entire bone region defined by Ø. The attenuation distribution is handled the same way as the density. In the bone region, the processes use an attenuation value of 2 dB/(cm-MHz)) and 0.0022 dB/(cm-MHz)) in the non-bone region. The bone region uses an attenuation value different from water because it is defined by the level set. For simplicity, water attenuation is used in the rest of the model. The level set method can handle an arbitrary number of bones in the domain, as well as the ability to merge bone regions in the event that only one bone cross-section is in the imaging plane when the initial model starts with two (or more).

Using the definition of the sound speed distribution in Eq. 4, a method to evolve the level set function in a way that decreases the error is needed. Following Kadu and Leeuwen, 2016; and Zheglova et al., 2012, and using the chain rule, one arrives at the expression:

$$\frac{\partial E}{\partial \emptyset} = \frac{\partial E}{\partial c}\frac{\partial c}{\partial \emptyset} \qquad (6)$$

to evolve the level set. In this study, it is assumed that the bulk bone density ($\rho_{bone}$) perfectly correlates with the bulk bone sound speed ($c_{bone}$), so any changes of Ø with respect to c are also applied to ρ. The second term in Eq. 6 is known from Eq. 34, and the third term in the equation is:

$$\frac{\partial c}{\partial \emptyset} = (c_{bone} - c_{soft})\delta(\emptyset(x, y)) \qquad (7)$$

where $\delta$ is the delta function. The presence of $\delta$ is concerning, but in practice, is dealt with by approximating the function. In this study, following Zheglova et al., 2012, the function:

$$\delta[\emptyset(x, y)] = \begin{cases} \frac{1}{2\epsilon}\left(1 + \cos\left(\frac{\pi\emptyset}{\epsilon}\right)\right), & |\emptyset| \leq \epsilon \\ 0 & |\emptyset| > \epsilon \end{cases} \qquad (8)$$

approximates $\delta$ where $\epsilon = 1.5\Delta x$, and $\Delta x$ is the grid spacing of the inversion domain. Regularization of the zero-level set contour takes place by penalizing its' curvature. The curvature, κ, is given by $$\kappa = \nabla \cdot \frac{\nabla \emptyset}{|\nabla \emptyset|}. \qquad (9)$$

Level set functions typically call for re-initialization after a few evolutions of the contour to ensure the function remains a distance function. There are many techniques for re-initialization, but in this case, $\emptyset$ is re-calculated after each time it is updated by explicitly computing the minimum distance of each pixel in the domain from the zero-level sets.

Methods—Generation of Initial Sound Speed and Density Distribution

The FWI process can require an initial guess in the starting model. The synthetic aperture focusing technique (SAFT) applied to the observed data set results in a reflection image, like a conventional ultrasound image. A snake process segments the outer boundary of bone in the resulting image, and the inner boundary is assumed to be the same as the outer boundary shrunk by 25%. The inner boundary is not explicitly segmented for simplicity since it is expected to be a low SNR feature or poorly resolved in an ultrasound image using constant velocity imaging techniques, such as SAFT. The snake segmentation employs a 100-point contour, 800 iterations, line attraction, and no edge attraction. The inner and outer bone boundary segmentations allow the definition of bone and soft tissue regions in the initial sound speed, density, and attenuation distributions. Inserting literature values for sound speed, density, and attenuation in both regions yields an initial starting model that accounts for the bone geometry and acoustic properties.

Methods—Inversion Process

In practice, FWI processes invert discrete frequency bands of the experimental data set with increasing central frequency as the number of process iterations increases to avoid cycle skipping. In this study, the three frequency bands used for the inversion are 20-200 kHz, 200-300 kHz, and 300-500 kHz. These bands cover the available bandwidth for the inversion domain and reduces the center wavelength by approximately 40% between bands. This is done intentionally to avoid cycle skipping and moving too quickly to higher frequencies. The dependence of the process performance on frequency band choices is not examined, but the choice made here is in line with the common practice of using lower frequencies first and progressively increasing the frequency content of the observational data in the acoustic wave form inversion to avoid cycle skipping.

The process proposed in this study is summarized as follows:
i. Create pulse echo image using iso-velocity migration.
ii. Segment pulse echo image for bone region and create the initial sound speed and density maps.
iii. Initialize $\emptyset$ using the segmentation of the bone.
iv. Generate $e_n$ with a random number generator and encode synthetic sources and experimental data.
v. Choose frequency band of data and apply appropriate time domain filters.
vi. Compute $\partial E/\partial c$: take the average of 8 estimates of $\partial E/\partial c$ (parallelize over 8 cores).
vii. Compute $\partial c/\partial \emptyset$.
viii. Update bone geometry by evolving $\emptyset$ using:

$$\emptyset = \emptyset - \mu_\emptyset \frac{\partial E}{\partial c}\frac{\partial c}{\partial \emptyset} - \mu_\kappa \kappa \tag{10}$$

where $\mu_\emptyset$ and $\mu_\kappa$ are scalar weighting factors.
ix. Re-initialize $\emptyset$.
x. Update $c_{bone}$ using:

$$c_{bone} = c_{bone} - \mu_{bone}\int\int\frac{\partial E}{\partial c}H(\emptyset)dxdy \tag{11}$$

where $\mu_{bone}$ is a scalar weighting factor.

xi. Update $c_{soft}$ for $\emptyset<0$ using:

$$c_{soft}(x, y) = c_{soft}(x, y) - \mu_{soft}\frac{\partial E}{\partial c} \tag{12}$$

where $\mu_{soft}$ is a scalar weighting factor.
xii. Return to step (iv) or terminate inversion.

The weighting parameters $\beta$, $\mu_\emptyset$, $\mu_\kappa$, $\mu_{bone}$, and $\mu_{soft}$ can be determined empirically.

Results

Figure 44C:
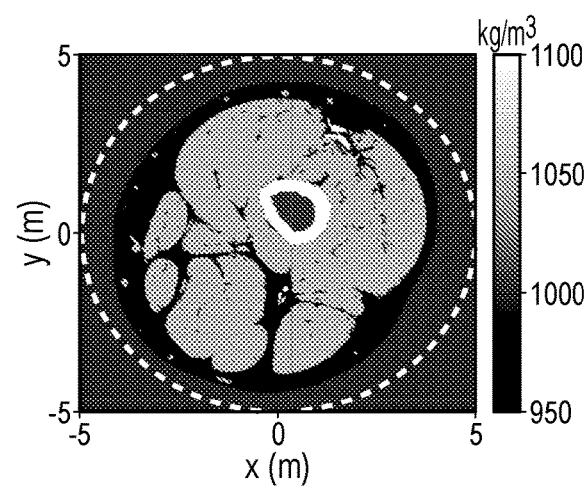
Figure 44D:
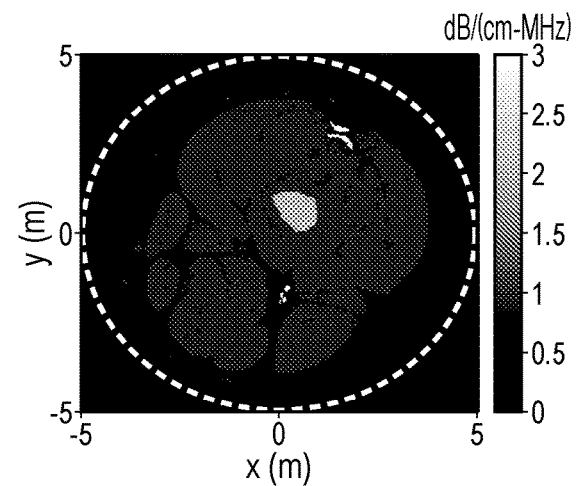

Results from two numerical phantoms are presented utilizing the process outlined above. The first result is of the numerical phantom representing a long bone in water (FIG. 44A). The second inversion is of a small human femur in water (FIGS. 44B-D). The inversion results for the small human femur are also compared to conventional source encoding FWI results from the same phantom.

Results—Bone Only Phantom

Figure 46A:
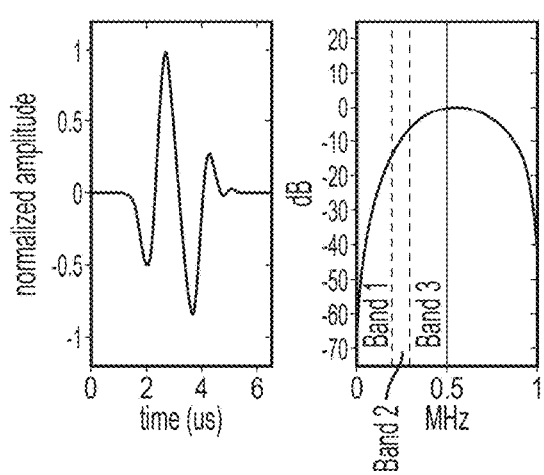
FIGS. 46A-46F illustrate results from an inversion of a numerical phantom of bone in water.
Figure 46B:
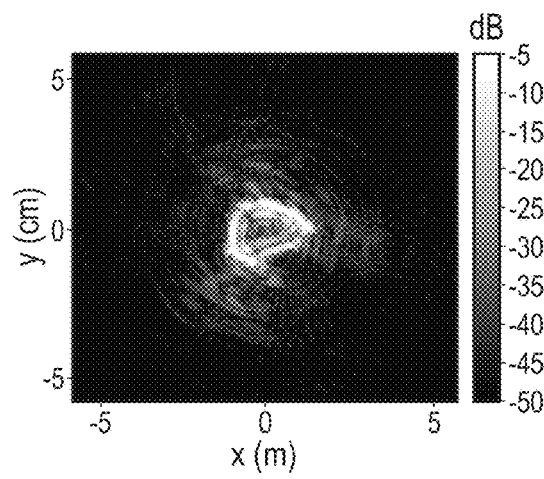
Figure 46C:
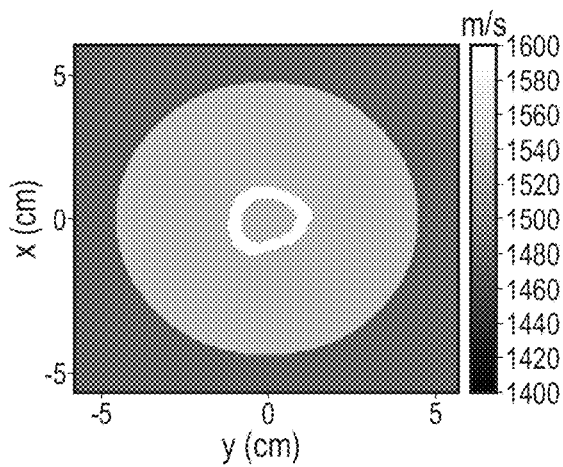
Figure 46D:
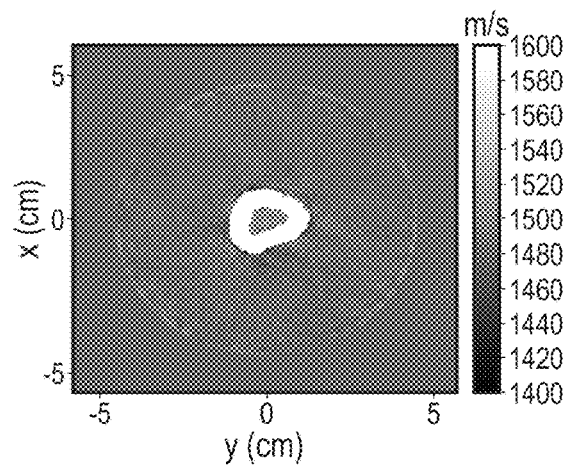
Figure 46E:
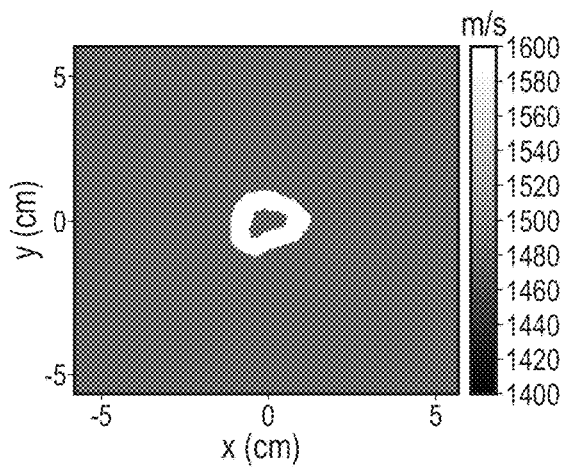
Figure 46F:
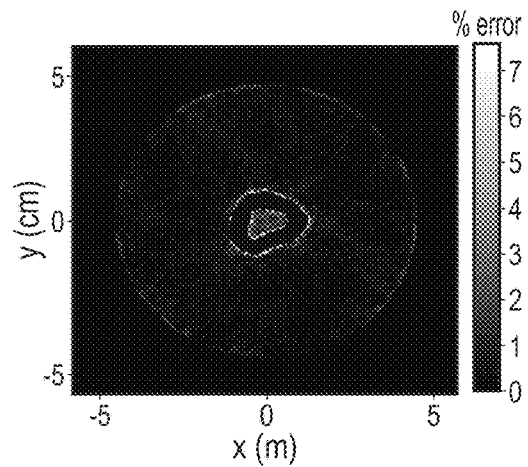

A pulse echo image of the phantom (FIG. 46B) allows segmentation of the bone region and generation of an initial sound speed map of the domain (FIG. 46C) using values from the literature of 1480 m/s for water, 1540 m/s for soft tissue, and 3200 m/s for bone. The inversion occurs over three frequency bands: 40 iterations in band 1, and 30 iterations in bands 2 and 3 (FIG. 46A). After 100 iterations, the inversion returns a reconstructed domain (FIG. 46D) with similar properties to the ground truth (FIG. 46E). The error in the bone sound speed is 0.24% (8 m/s), and the mean error for the water velocity is 0.46% (7 m/s). The error in the bone shape is on the order of a pixel ($\Delta x$=0.463 mm) (FIG. 46F). The inversion completed in approximately 3.3 hours using a quad-core 3.5 GHz processor.

Results—Human Femur Phantom

A pulse echo image of the phantom (FIG. 47B) allows segmentation of the bone region and generation of an initial sound speed map of the domain (FIG. 47C) using values from the literature of 1480 m/s for water, 1540 m/s for soft tissue, and 3200 m/s for bone.

Figure 47A:
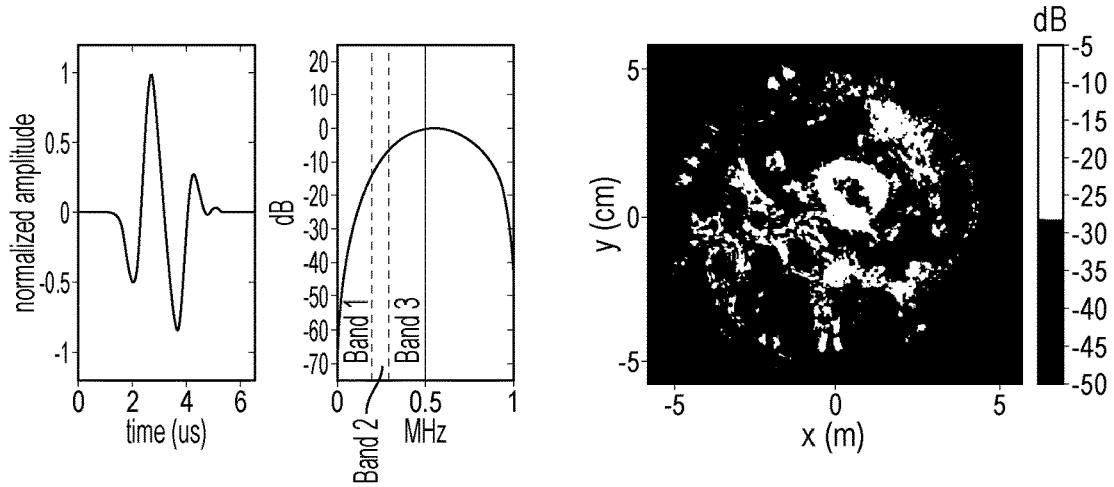
FIGS. 47A-47F illustrate results from an inversion of a numerical femur phantom in water.
Figure 47B:
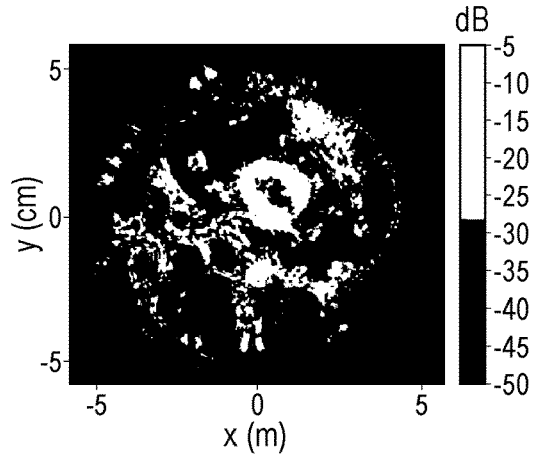
Figure 47C:
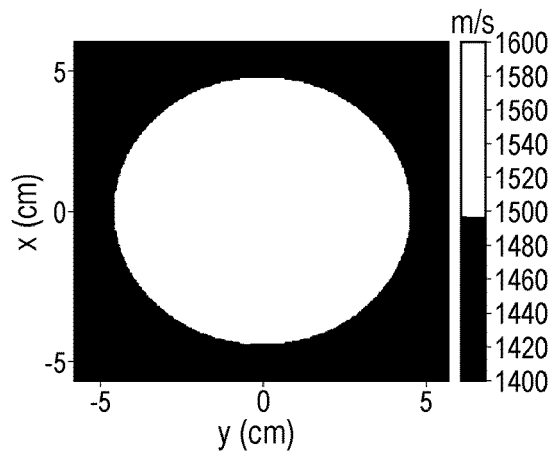
Figure 47D:
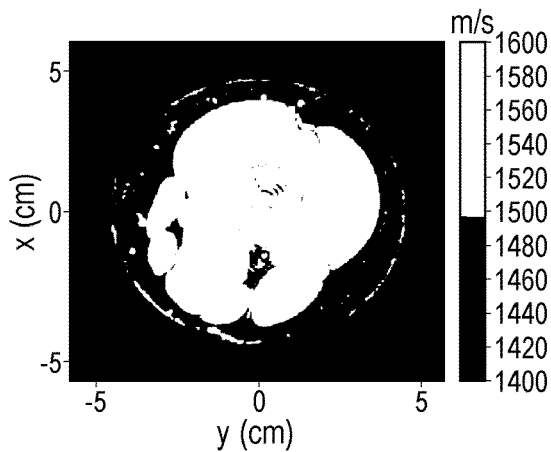
Figure 47E:
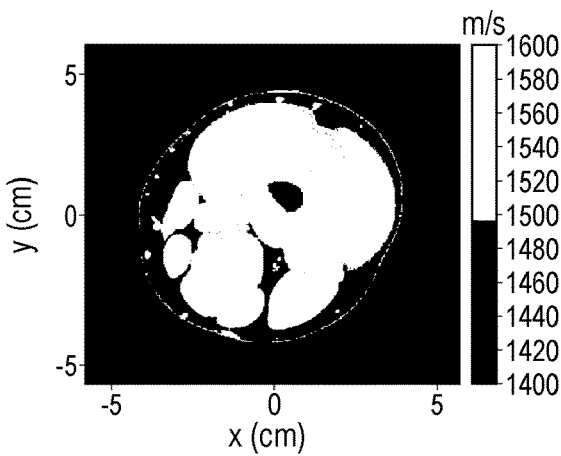
Figure 47F:
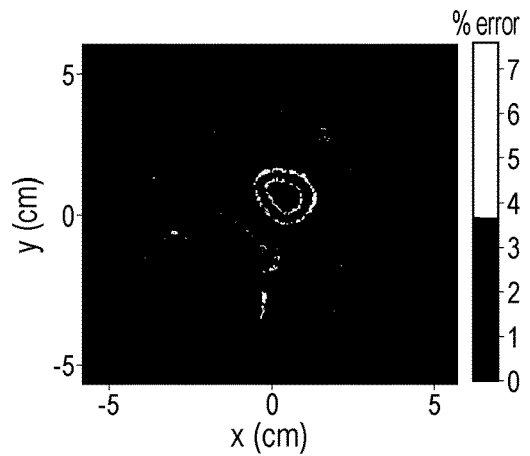

The inversion occurs over three frequency bands: 40 iterations in band 1, and 30 iterations in bands 2 and 3 (FIG. 47A). After 100 iterations the inversion returns a reconstructed domain (FIG. 47D) with similar properties to the ground truth (FIG. 47E). The error in the bone sound speed is 1.7% (60 m/s), and the mean error in the soft tissue is 0.8% (13 m/s). The error in the bone shape is on the order of a pixel ($\Delta x$=0.463 mm) (FIG. 47F). The inversion completed in approximately 3.3 hours using a quad-core 3.5 GHz processor.

The results from employing FWI with source encoding, but without the level set (LS) regularization, to the synthetic data from the human femur phantom (FIGS. 48A-C) show reduced performance relative to the result shown in FIGS. 47A-F. For this inversion, all parameters are kept constant, except the LS is no longer used to evolve the bone geometry. The inversion occurs over three frequency bands: 40 iterations in band 1, and 30 in bands 2 and 3 (FIG. 47A). After 100 iterations the inversion returns a reconstructed domain (FIG. 48A) with similar properties to the ground truth (FIG. 47E), but artifacts are present. The mean error in the bone sound speed is 5.1% (177 m/s), and the mean error in the soft tissue is 1.8% (28 m/s), both higher compared the proposed technique using level set regularization. The bone area is defined as anywhere in the domain where the sound speed is above 2000 m/s. The inversion completed in approximately 3.3 hours using a quad-core 3.5 GHz processor. Note the increased bulk errors and artifacts in the sound speed images (FIG. 48A-B) compared to those in FIGS. 47A-F. The artifacts are most noticeable near the bone boundary and inside the bone region (FIG. 48A-B). A cross section of the two inversion results and the true model (FIG. 48C) show the level set regularized inversion has better accuracy in terms of sound speed in the soft tissue, bone boundary location, and bulk bone sound speed.

DISCUSSION

Sound speed images of bone and soft tissue are reconstructed from numerical data sets using FWI with source encoding coupled with level set (LS) techniques. The results demonstrate the recovery of sound speed and geometry of cortical bone and soft tissue using these techniques in less than 4 hours using a quad core 3.5 GHz CPU desktop computer. The technique recovers sound speed with less than 5% error over the majority of the imaging domain. Lastly, employing the LS technique to regularize the bone geometry improves the sound speed and geometry estimates of bone relative to conventional source encoding FWI techniques. The inversion approach utilizes a priori information about the general structure of cortical bone as the initial sound speed distribution, which the FWI and level set techniques evolve to a final estimate of the domain properties and geometry.

The results from using these FWI techniques applied to numerical bone phantoms suggest ultrasound tomography systems can provide quantitative information on bone and soft tissue material properties as well as geometry. Potential applications include muscle volume and muscle status monitoring, prosthetic fitting, and osteoporosis monitoring and detection. Source encoding techniques can be useful in reducing computational costs when attempting volumetric reconstructions where it is likely that more than 72 transmissions will be collected, and more computation cost and time saving can be realized.

Example 6. Ultrasonic Imaging of Cortical Bone and Soft Tissue Using the Level-Set Method to Regularize Full Waveform Tomography Techniques: Observational Data from a UST System Quantitative images of limb cross-section, bone, and soft tissue from in vitro animal tissue samples are generated using full waveform inversion (FWI) with level set regularization. A priori information about the general structure of cortical bone provides an initial estimate of the sound speed distribution. The FWI and level set techniques iteratively update the sound speed map to a final estimate of the domain properties and geometry. Results demonstrate the recovery of sound speed and geometry of cortical bone and soft tissue with modest computational cost. As noted, above, bone imaging and quantification is of general clinical utility. Applications include prosthetic fitting, fracture detection and the diagnosis and monitoring of osteoporosis. Development of FWI techniques for soft and hard tissue applications can provide for, in addition to geometry, quantitative images of the body, and can be generated without radiation and potentially at low cost.

An overview of FWI, source encoding, and level set (LS) methods is provided above. In this study, a water-immersion-based UST scanner is employed for sound speed imaging of bone and soft tissue. The experimental results demonstrate that quantitative sound speed images of cortical bone and soft tissue can be resolved using FWI techniques coupled with LS regularization. Experimental data sets are collected using a cylindrical mechanically scanning ultrasound tomography system. Acquired data sets include phantoms and bovine shank samples. A priori information about the general structure of cortical bone and soft tissue are utilized to generate the initial sound speed distribution. Images formed using: (1) FWI with the LS regularization; (2) FWI using subsets of the data with the LS regularization; and (3) FWI with source encoding, global coherence penalty, and LS regularization are shown and compared to conventional FWI results.

Methods—Scanning Hardware

The experimental data collection is completed using a custom-made single element dual-transducer cylindrically-scanning immersion UST scanner (UST scanner) (see, for example, FIG. 1). Both transducers can be independently positioned over the entire 3600 aperture and translate ~7 cm vertically for acquiring multiple 2-D slices or volume images of a target, as well as enable iterative development of scanning procedures. The two transducers are removable, allowing use of different transducers with varying properties, such as beam width and frequency. Further details describing the general mechanical and electrical design of a UST system can be found in Zhang et al., 2015a.

The data acquisition system consists of a low frequency pulser (DPR300, Imaginant, Pittsford, NY, USA), which drives the transmit transducer. The pulser also preforms analog gain and filtering of the A-line signals from the receiving transducer (which can be the same as the transmitter). The analog signal coming from the pulser is digitized at 50 MHz (NI PXie-1073, National Instruments, Austin, TX, USA) and streamed to a PC where the signal is down sampled to 15 MHz and saved for processing. Further details on general data acquisition system setup can be found in Zhang et al., 2015.

The experimental data sets consist of bistatic (separate source and receiver) scans comprised of 72 transmit locations equally spaced 5° apart, resulting in a 360° synthetic aperture. At each transmit location, 1333 100 µs long channel data lines are sequentially acquired from the receiving transducer at 1333 equally distributed spatial locations (0.2345° apart), resulting in a 313° receive aperture. A full 360° receive aperture was not included due to mechanical interference between the mounting brackets; the interference makes 23.5° of the circular aperture, centered on the transmit bracket, inaccessible to the receiver. For all scans, a 0.5 or 1 MHz (broadband) fan beam transducer with 65° full beam width is used for transmit. For receive, a matching 0.5 or 1.0 MHz broadband point receiver is used.

The transmit transducer and driving electronics were characterized with a calibrated hydrophone to ensure acoustic exposure is within bounds set by the Food and Drug Administration (FDA) standards for ultrasound use on humans. These measurements can ensure that the processes are tested on data with SNR similar to what would be seen from scans of humans. All scanning procedures described are approved by the MIT internal review board and committee on animal care.

Methods—Wave Equation Solver

Solves of the wave equation are done using the MATLAB (Mathworks, Natick, Ma, USA) based k-wave simulation toolbox. The simulation includes the effects of sound speed, c, in units of m/s, density, $\rho$, in units of $kg/m^3$ and attenuation, a, in units of dB/(cm-MHz). Shear wave effects are not simulated to reduce computational costs and for simplicity. The observational data sets consists of 72 transmits, each with 418 receives (maximum number that fit in the grid) and 2500 time samples, yielding ~7.5×10⁷ observations of the domain. The grid for inversion is 256×256, yielding ~6.6×10⁴ unknowns to resolve. In practice, a circular portion of the 256×256 grid is resolved because the grid is square and the acquisition geometry is circular. Further, the sound speed estimation zone is restricted to a 14 cm diameter region centered on the center of the UST scanner. This region contains ~13×10⁴ unknowns. The over sampling of the domain can be required to overcome the non-linear and ill-posed nature of the inverse problem.

Methods—Inversion Technique

The FWI technique attempts to quantify the spatial distribution of physical parameters that give rise to the observed ultrasound time series data (e.g., pressure, velocity, and/or displacement). In this study, the observed ultrasound time series are the experimental datasets collected from the UST scanner. The reconstruction is achieved by minimizing the difference between the observed time series and model time series generated by numerical simulation. The conventional FWI technique minimizes the objective function:

$$E(c, \rho) = \frac{1}{2}\sum_{n=1}^{N} \|u(c, \rho, s_n) - d_n\|^2 - \|c - c_0\|^2 \tag{33}$$

where E is the mean square error between the observed and modeled data, u is the wave. equation operator which outputs a modeled time series of velocity with units of Pa, $s_n$ is the source for the $n^{th}$ transmission, $d_n$ is the observed time series data from the $n^{th}$ transmission with units of Pa, and $c_o$ is the initial sound speed distribution. The $\|c-c_o\|^2$ in Eq. 33 is a regularization term and is omitted in the remainder of this section for brevity. The gradient of Eq. 33 with respect to c for a single source can be found in the literature and is given by:

$$\frac{\partial E}{\partial c} = \frac{2}{c^3}\sum_{n=1}^{N}\int_0^T \frac{\partial p_n}{\partial t} p_n^*(t-T)dt \tag{34}$$

where p is the recorded pressure with units of Pa, p* is the adjoint pressure field, and T is the duration of the observed time series. The $p_n$ and $p^*_n$ terms each require a wave equation solve, which means 2N solves of the wave equation are needed to compute $\partial E/\partial c$. In this study, processes using Eq. 34 are referred to as conventional FWI (C-FWI). The cost function in Eq. 33 can be slightly modified into Eq. 35 to enable the use of source encoding:

$$E(c, \rho) = \frac{1}{2}\sum_{n=1}^{N}\left(\hat{u}(c, \rho, s_n)\cdot \hat{d}_n\right) \tag{35}$$

$$\hat{u} = \frac{u}{\|u\|}\hat{d} = \frac{d}{\|d\|} \tag{36}$$

$$u=\Sigma_{n=1}^{N}u(c,\rho,e_n\otimes s_n)d=\Sigma_{n=1}^{N}e_n\otimes d_n \tag{37}$$

where $e_n$ is a random encoding sequence, $\otimes$ is the convolution operator, and $\|\|$ indicates the $L^2$ norm of each trace in u and d. Here, $e_n$ is randomly assigned to be −1 or 1 for each transmission, and $e_n$ changes on each iteration of the gradient descent process, similar to previous studies. The $\hat{u}(c, \rho, s_n)\cdot\hat{d}_n$ term in Eq. 35 is the global coherence norm (GCN), and its gradient is given as.

$$\frac{\partial E}{\partial c} = \frac{2}{c^3}\int_0^T \frac{\partial p}{\partial t}\hat{r}(t-T)dt \tag{38}$$

$$\hat{r} = \frac{1}{\|u\|}[\hat{u}(\hat{u}\cdot\hat{d}) - \hat{d}]. \tag{39}$$

The computational burden of FWI typically scales linearly with the number of transmits. Source encoding, however, makes the computational cost of FWI independent of the number of sources used in an experiment, as can be seen by comparing Eq. 38 and Eq. 34. The reduction in computational expense comes at the cost of only approximating $\partial E/\partial c$ from Eq. 34 at each step in the inversion. If enough iterations are run, however, the integrated effect of applying $\partial E/\partial c$ from Eq. 38 can yield a nearly identical result as traditional FWI techniques. When using Eq. 38 in FWI processes, it will be referred to as GCN-FWI.

In this study, ρ and a take constant binary values of 1050 kg/m³ and 0.0022 dB/(cm-MHz) for soft tissue and 1500 kg/m³ and 2.0 dB/(cm-MHz) for bone. A regularization term is often added to Eq. 33 and 35, such as a roughness penalty, but in this study, the LS method implicitly regularizes Eq. 33. The LS method allows for a sharp change in sound speed and density between the bone region and soft tissue regions, as is the case in biological tissue. The technique also provides an efficient means of updating the bone geometry to align with the observed data by enabling bone boundaries to change from one iteration to the next. In contrast, traditional FWI techniques can require many iterations to convert a low sound speed (e.g., soft tissue) pixel to a high sound speed (e.g., bone) pixel.

One potential drawback to the LS approach, as it is deployed here, is that the bone properties are defined as homogeneous in the bone region. It is known that bone properties change over the thickness of the cortical wall by 10-20%. The LS technique can potentially handle such spatial variations, but it was chosen to estimate a single homogeneous bone velocity for simplicity.

The LS method uses a distance function, Ø (FIG. 45A), to track the location of a contour or contours and allows the contour(s) (and Ø) to evolve as "forces" act on the contours' surfaces. In this case, the LS function defines the bone regions and non-bone regions of the domain and defines the c and ρ distributions as follows:

$$c(x,y)=c_{bone}H(\emptyset)+(1-H(\emptyset))c_{soft}(x,y) \tag{4}$$

$$\rho(x,y)=\rho_{bone}H(\emptyset)+(1-H(\emptyset))\rho_{soft} \tag{5}$$

where x and y are the spatial coordinates of the domain, and H is the Heaviside function (FIG. 45B). The attenuation distribution is defined the same way as the density. Locations in the domain where Ø>0 signifies bone, and where Ø<0 signifies soft tissue. The term $c_{soft}(x, y)$ is expressed explicitly as a function of x and y to highlight that its values change from grid point to grid point, in contrast to $c_{bone}$, which takes a single value over the entire bone region defined by Ø.

Using the definition of the sound speed distribution in Eq. 4, a method to evolve the LS function while minimizing Eq. 33 or Eq. 35 is needed. Following previous works and using the chain rule, the expression $$\frac{\partial E}{\partial \emptyset} = \frac{\partial E}{\partial c}\frac{\partial c}{\partial \emptyset} \tag{6}$$

can be derived to evolve the LS. In this study, the density is assumed to correlate with c, so any changes of Ø with respect to c are also applied to ρ. The second term in Eq. 6 is known from Eq. 34 or Eq. 38, and the third term in the equation is defined as:

$$\frac{\partial c}{\partial \emptyset} = (c_{bone} - c_{soft})\delta(\emptyset(x, y)) \qquad (7)$$

where δ is the delta function. In this study, the function $$\delta[\emptyset(x, y)] = \begin{cases} \frac{1}{2\epsilon}\left(1 + \cos\left(\frac{\pi\emptyset}{\epsilon}\right)\right), & |\emptyset| \leq \epsilon \\ 0, & |\emptyset| > \epsilon \end{cases} \qquad (8)$$

approximates δ where ε=1.5Δx, and Δx is the grid spacing of the inversion domain. Regularization of the zero LS contour takes place by penalizing its curvature, κ, given by $$\kappa = \nabla \cdot \frac{\nabla \emptyset}{|\nabla \emptyset|}. \qquad (9)$$

LS functions typically call for re-initialization after a few evolutions of the contour to ensure the function remains a distance function. There are many techniques for re-initialization; but in this case, Ø is renormalized by solving $$\frac{\partial \emptyset}{\partial t} - H(\emptyset)(|\nabla \emptyset| - 1) = 0 \qquad (39)$$

to a steady solution.

Methods—Generation of Initial Sound Speed and Density Distribution

The LS technique can require an initial guess of the bone geometry and sound speed to serve as a starting model. Applying the synthetic aperture focusing technique (SAFT) to the synthetic data set results in a reflection image, like a conventional ultrasound image. A snake process segments the outer boundary of bone in the resulting image, and the inner boundary is assumed to be the same as the outer boundary shrunk by 25%. The inner boundary is not explicitly segmented for simplicity since it is expected to be a low SNR feature or poorly resolved in an ultrasound image using constant velocity imaging techniques, such as SAFT. The inner and outer bone boundary segmentations allow the definition of bone and soft tissue regions in the initial sound speed and density distributions. Inserting literature values for sound speed and density in both regions yields an initial starting model that accounts for the bone geometry and sound speed.

Methods—Inversion Process

In practice, FWI processes invert discrete frequency bands of the experimental data set with increasing central frequency as the number of process iterations increase to avoid cycle skipping. In this work, two sets of frequency bands are utilized, as show in Table 8. The maximum frequency is set by the discretization of the inversion domain as well as the finite bandwidth of the source.

TABLE 8

Frequency bands used for FWI processes

| | Set 1 | Set 2 |
|---|---|---|
| Band 1 | 75-200 kHz | 75-200 kHz |
| Band 2 | 75-300 kHz | 200-300 kHz |
| Band 3 | 75-400 kHz | 300-400 kHz |
| Band 4 | 75-500 kHz | 400-500 kHz |
| Band 5 | 75-600 kHz | 500-600 kHz |

The conventional FWI (C-FWI) process in use here works as follows:
i. Create pulse echo image using iso-velocity migration.
ii. Segment pulse echo image for bone region and create the initial sound speed and density maps.
iii. Initialize Ø using the segmentation of the bone.
iv. Choose frequency band of data and apply appropriate time domain filters.
v. Compute ∂E/∂c (Eq. 34): computed 72 times in parallel, once for each transmit.
vi. Compute ∂c/∂Ø
vii. Conduct line search for $\mu_{soft}$.
viii. Update bone geometry by evolving Ø using:

$$\emptyset = \emptyset - \mu_\emptyset \frac{\partial E}{\partial c}\frac{\partial c}{\partial \emptyset} - \mu_\kappa \kappa \qquad (10)$$

where $\mu_\emptyset$ and $\mu_\kappa$ are scalar weighting factors.
ix. Re-initialize Ø.
x. Update $c_{bone}$ using:

$$c_{bone} = c_{bone} - \mu_{bone}\int\int \frac{\partial E}{\partial c}H(\emptyset)dxdy \qquad (11)$$

where $\mu_{bone}$ is a scalar weighting factor.
xi. Update $c_{soft}$ for Ø<0 using:

$$c_{soft}(x, y) = c_{soft}(x, y) - \mu_{soft}\frac{\partial E}{\partial c} \qquad (12)$$

where $\mu_{soft}$ is a scalar weighting factor.
xii. Return to step (iv) or terminate inversion.

The conventional FWI process using subsets of the observational data (DS-FWI) is as follows:
i. Create pulse echo image using iso-velocity migration.
ii. Segment pulse echo image for bone region and create the initial sound speed and density maps.
iii. Initialize Ø using the segmentation of the bone.
iv. Take every $5^{th}$ transmit as data set (15 transmit total from 72 transmit data set).
v. Choose frequency band of data and apply appropriate time domain filters.
vi. Odd iterations numbers increment first 8 transmit by one; even iteration number increment last 7 transmits by one (the whole dataset is repeatedly used as iterations go on).
vii. Compute ∂E/∂c (Eq. 34): computed 15 times, once for each transmit.

viii. Compute $\partial c/\partial \emptyset$.
ix. Conduct line search for $\mu_{soft}$.
x. Update bone geometry by evolving $\emptyset$ using:

$$\emptyset = \emptyset - \mu_\emptyset \frac{\partial E}{\partial c}\frac{\partial c}{\partial \emptyset} - \mu_\kappa \kappa \quad (10)$$

where $\mu_\emptyset$ and $\mu_\kappa$ are scalar weighting factors.
xi. Re-initialize $\emptyset$.
xii. Update $c_{bone}$ using:

$$c_{bone} = c_{bone} - \mu_{bone}\int\int\frac{\partial E}{\partial c}H(\emptyset)dxdy \quad (11)$$

where $\mu_{bone}$ is a scalar weighting factor.
xiii. Update $c_{soft}$ for $\emptyset<0$ using:

$$c_{soft}(x,y) = c_{soft}(x,y) - \mu_{soft}\frac{\partial E}{\partial c} \quad (12)$$

where $\mu_{soft}$ is a scalar weighting factor.
xiv. Return to step (iv) or terminate inversion.

The. FWI with source encoding process and global coherence noun (GCN-FWI) in use here works as follows:
i. Create pulse echo image using iso-velocity migration.
ii. Segment pulse echo image for bone region and create the initial sound speed and density maps.
iii. Initialize $\emptyset$ using the segmentation of the bone.
iv. Generate $e_n$ with a random number generator and encode synthetic sources and experimental data.
v. Choose frequency band of data and apply appropriate time domain filters.
vi. Compute $\partial E/\partial c$ (Eq. 38): take the average of 8 estimates of $\partial E/\partial c$ (parallelize over 8 cores).
vii. Compute $\partial c/\partial \emptyset$.
viii. Update bone geometry by evolving $\emptyset$ using:

$$\emptyset = \emptyset - \mu_\emptyset \frac{\partial E}{\partial c}\frac{\partial c}{\partial \emptyset} - \mu_\kappa \kappa \quad (10)$$

where $\mu_\emptyset$ and $\mu_\kappa$ are scalar weighting factors.
ix. Re-initialize $\emptyset$.
x. Update $c_{bone}$ using:

$$c_{bone} = c_{bone} - \mu_{bone}\int\int\frac{\partial E}{\partial c}H(\emptyset)dxdy \quad (11)$$

where $\mu_{bone}$ is a scalar weighting factor.
xi. Update $c_{soft}$ for $\emptyset<0$ using:

$$c_{soft}(x,y) = c_{soft}(x,y) - \mu_{soft}\frac{\partial E}{\partial c} \quad (12)$$

where $\mu_{soft}$ is a scalar weighting factor.
xii. Return to step (iv) or terminate inversion.

The scalar weighting factors $\beta$, $\mu_\emptyset$, $\mu_\kappa$, $\mu_{bone}$ and $\mu_{soft}$ are determined empirically. The weighting factors are typically determined using the GCN-FWI process or the DS-FWI process because they can be run on a local desktop computer.

Methods—Computational Hardware

Computational hardware employed for these inversions includes of two different computing systems. The first system is a computing cluster (Sabalcore Inc., Melbourne, FL, USA); each core consists of a 2.7 GHz processor with 5.5 GB RAM each. The C-FWI processes were ran on the Sabalcore cluster using 72 cores (one per transmit). The GCN-FWI inversion and DS-FWI ran on desktop computers with a quad core 3.7 GHz processor and 32 GB RAM.

Methods—Ground Truth Measurements

The velocity estimates from the resulting sound speed images are compared to velocity estimates from tissue samples removed from the sample in the UST system after scanning. The ground truth velocity estimates are carried out using a micrometer (Starrett IP 67 2900, The LS. Starrett Company, Athol, Ma, USA) and a pair of 9 MHz transducers (Olympus V1091, Olympus, Tokyo, Japan) (FIGS. 36A-B). The same electronics from the tank system are used to send and receive signals for the ground truth measurements.

Two experimental setups are utilized to estimate the tissue ground truth sound speed, as shown in FIGS. 36A-B and described above. The first setup uses a potentiometer and a single transducer in reflection mode. The second setup uses two transducers in through transmission mode with a pair of calipers. The first setup is for measuring soft tissue sound speed, and the second is for measuring bone sound speed. For soft tissue sound speed measurement, a sample is placed between the transducer and the granite block, and a pulse is sent through the sample. The reflection from the granite block is detected at the transducer, and velocity is measured based on the distance of the transducer from the slab and the two-way travel time. The bone velocity is measured using two transducers, one on either side of the bone. The bone thickness is measured with a set of calipers, and the one-way travel time from the source transducer to the receiving transducer is the travel time. The sound speed of the DI water in the scanning tank is evaluated using a temperature measurement from a thermometer with 0.01° F. resolution and an empirical relationship between temperature and sound speed.

Methods—Magnetic Resonance Imaging (MRI)

The bovine shank sample is scanned with a 3T MRI scanner (Siemens Medical Solutions, Malvern, PA, USA) with two-echo ultra-short echo-time (UTE) sequences and an abdominal coil wrapped around the target area of interest. The MRI images provide relative comparison of bone and soft tissue geometries. The MRI images do not provide sound speed information and do not exactly match the UST system acquisition due to differing orientation, deformation, and water immersion of the bovine sample in the UST scanner.

Results

Application of the C-FWI and GCN-FWI techniques to the experimental data sets demonstrates successful quantification of the geometry and sound speed of the bone and soft tissue. Quantitative sound speed images from a bone phantom as well as a bovine sample are shown. Data acquisition methods are identical for all UST experimental data.

Results—Bone Phantom

The bone phantom data set verifies the process performance on a known high impedance target. The GCN-FWI and DS-FWI processes with LS regularization are tested on the bone phantom.

Figure 49A:
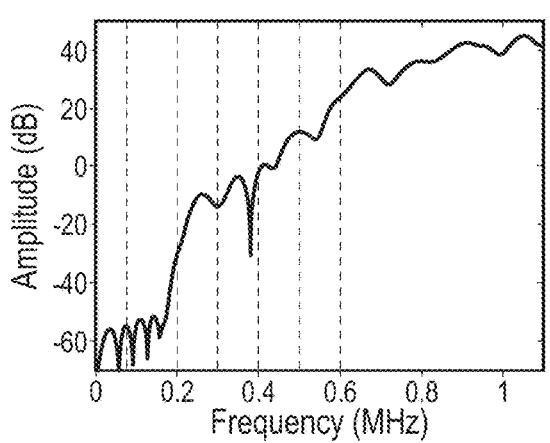
FIGS. 49A-49D illustrate initial conditions for a model and image of a target.
Figure 49B:
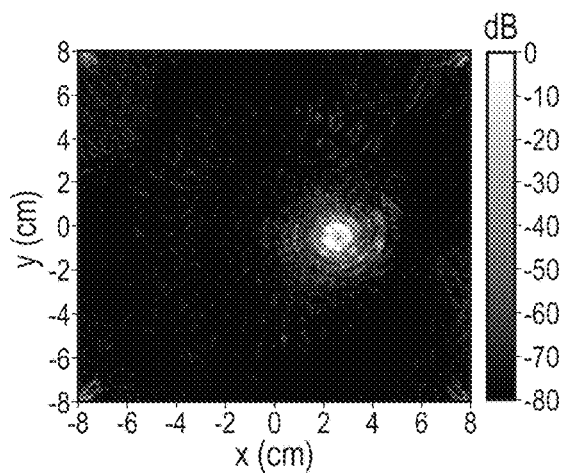
Figure 49C:
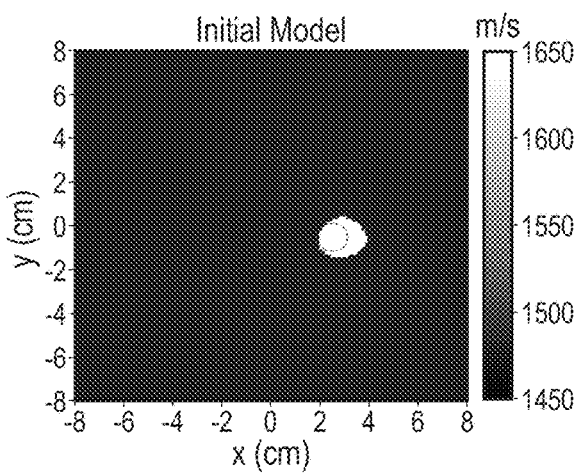
Figure 49D:
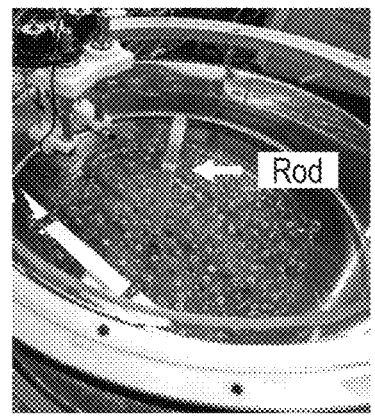
Figure 50A:
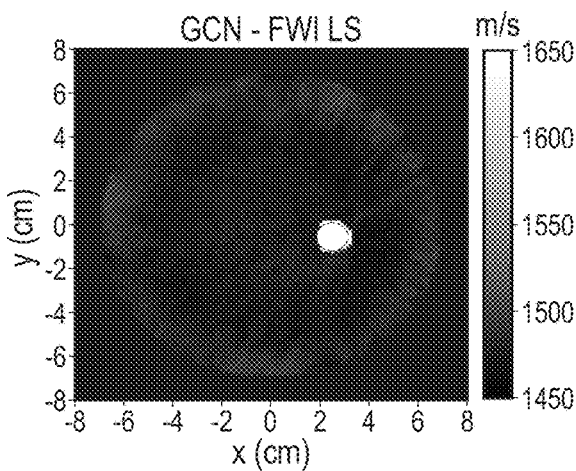
FIGS. 50A-50B are sound speed images of the rod generated with FWI techniques.
Figure 50B:
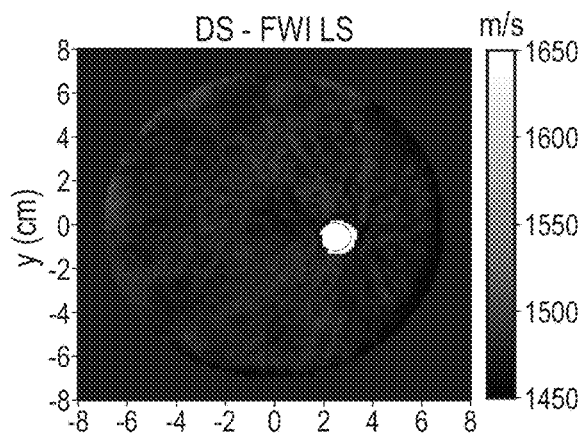

The bone phantom is a 0.508" diameter nylon rod mounted to the bottom of the tank. The inversion occurs over five frequency bands (FIG. 49A); the number of iterations the process runs in each band depends upon which process described above is run. The SAFT image of the rod (FIG. 49B) provides the spatial structure of the rod and water initial sound speed map of the domain (FIG. 49C). Sound speed values from the literature of 1480 m/s for water and 2200 m/w for the rod are assigned to each region. The experimental data set is collected with 1 MHz transducers.

Sound speed maps using GCN-FWI and DS-FWI are shown. Both techniques yield similar sound speed images with some differences in artifacts. Ultimately, the inverted models agree on the water sound speed and the rod sound speed (FIGS. 60A-B, Table 9).

TABLE 9

Average estimated sound speed values (m/s) for the nylon rod compared to ground truth estimates

| Material | ground truth (m/s) | Inverted (m/s) | Error (%) |
|---|---|---|---|
| Nylon Rod: GCN-FIT with LS regularization | | | |
| Nylon | 2210 | 2090 | −5.43 |
| water | 1484 | 1483 | −0.07 |
| Nylon Rod: DS-FWI with LS regularization | | | |
| Nylon | 2210 | 2080 | −5.88 |
| water | 1484 | 1480 | −0.27 |

Results—Beef Shank

The bovine shank sample is a 7" tall section of the bovine tibial hind leg. External hide has been removed but has all other tissue remaining. Two scans of the sample are done at two different z (vertical) locations separated by 1.9 cm.

Figure 51A:
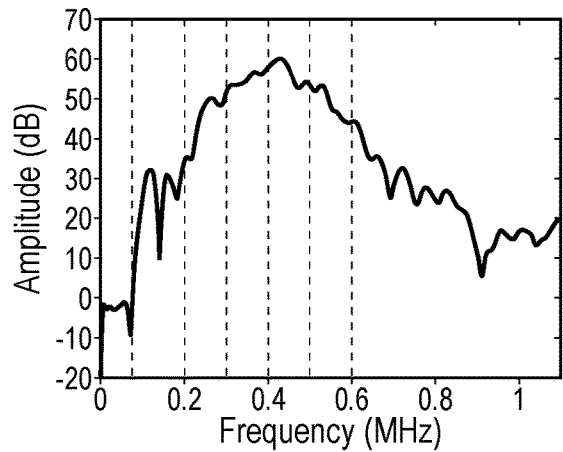
FIGS. 51A-51D illustrate initial conditions for a model and image of a target bovine shank.
Figure 51B:
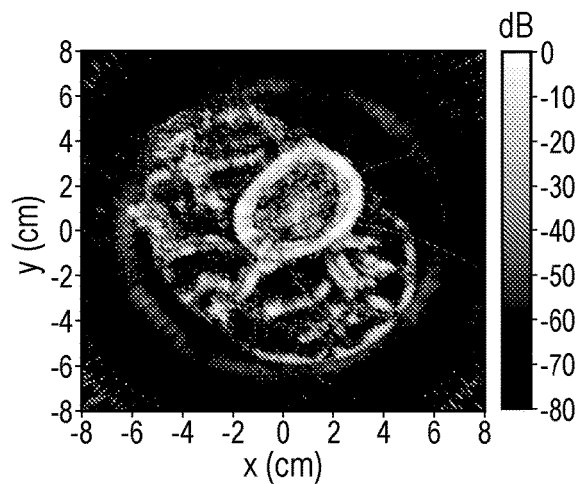
Figure 51C:
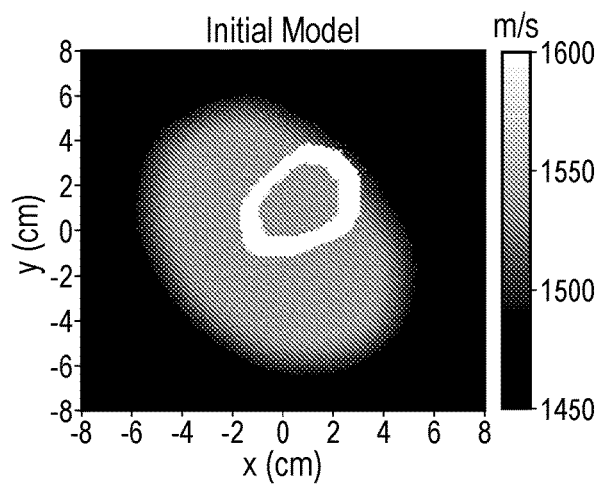

The inversion is run using five frequency bands (set 1, Table 8) (FIG. 51A); the number of iterations the process runs in each band depends on which process is run. The DS-FWI process took 8 hours to complete, and the remaining processes took approximately 3 hours either on a desktop computer or the 72-core computing cluster. The SAFT image of the bovine shank (FIG. 51B) provides the spatial structure of the bone, soft tissue, and water initial sound speed snap of the domain (FIG. 51C). Sound speed values from the literature of 1480 m/s for water, 1540 m/s for soft tissue, and 2800 m/s for the bone are assigned to each region. Appropriate density and attenuation values are also inserted into the starting models. The soft tissue velocity is spatially smoothed using a 2D Gaussian filter. The MRI image (FIG. 51D) shows the bone geometry as well as the characteristic soft tissue structure of the first bovine shank slice.

Figure 51D:
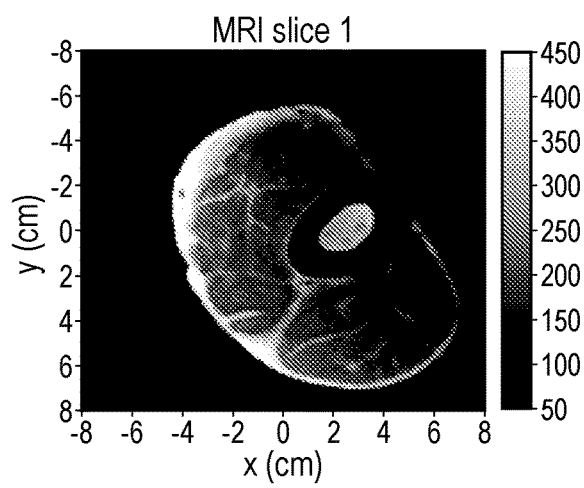

Sound speed images (FIGS. 52A-E) using GCN-FWI, DS-FM, and C-FWI with LS regularization are generated from the experimental data sets. A sound speed image is also constructed with the C-FWI process without LS regularization. The sound speed images (FIGS. 52A-E) reveal what appear to be connective tissue, fat, tendons, and the bone with clarity comparable to the corresponding MRI slice (FIG. 51D). The GCN-FWI, DS-FWI, and C-FWI with LS regularization yield similar sound speed images with some differences in artifacts. In particular, the GCN image contains more high frequency spatial variations in the sound speed and less contrast between the tissue and the water velocity. Ultimately, the inverted models agree on the bulk sound speed of soft tissue, water, and bone (FIGS. 52A-E, Table 10). The sound speed image from the C-FWI technique (FIG. 52E) (no LS regularization) yields similar sound speed images to the other techniques in the soft tissue regions but deviates on the bone geometry and sound speed (FIGS. 52A-E, Table 10). The technique also yields larger artifacts in the soft tissue regions that appear as if they are emanating from the bone surface as indicated by the arrows in FIG. 52E.

A higher grid resolution sound speed image is generated to test the resolution limits of the technique in conjunction with the experimental UST system.

Figure 52A:
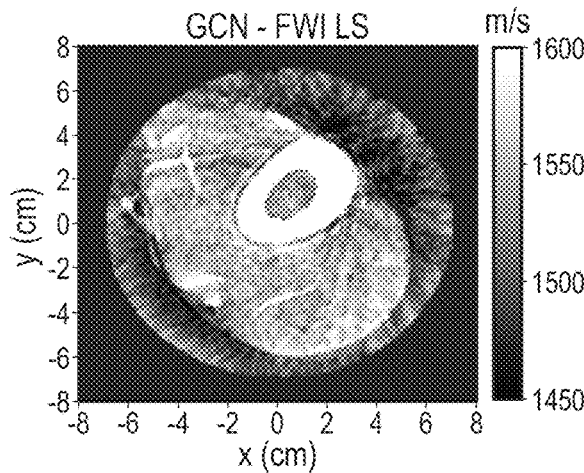
FIGS. 52A-52E are sound speed images of the bovine shank of FIG. 51D generated with FWI techniques.
Figure 52B:
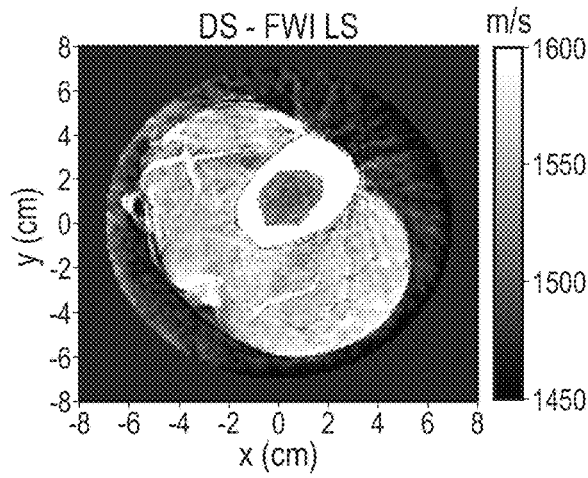
Figure 52C:
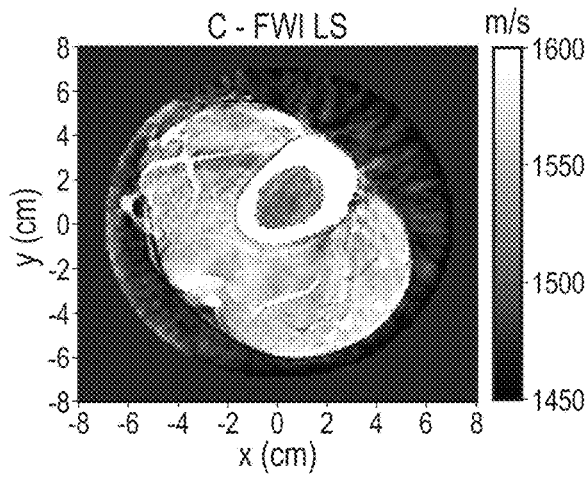
Figure 52D:
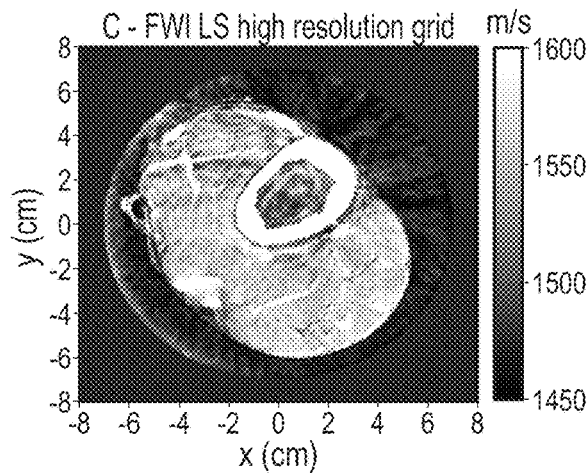
Figure 52E:
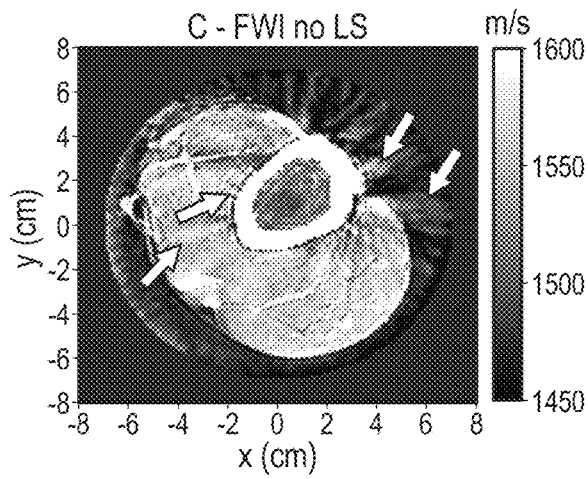

The sound speed image generated using the C-FWI process in FIG. 52D has twice the grid resolution of all others in FIGS. 52A-E. Some of the features in FIG. 52C, 52D are on the order of a single pixel, demonstrating subwavelength resolution of the technique. The thin fatty tissue layer on the outer surface of the bovine shank in FIG. 52D is only 1-2 pixels wide, which is 2.5-4.5 times smiler than the acoustic wavelength (2.6 mm) used in the inversion. The bone geometry is not as well estimated in FIG. 52D compared to the lower resolution images.

TABLE 10

Average sound speed (m/s) estimates for the bovine shank compared to ground truth values

| Material | Ground truth (m/s) | Inverted (m/s) | Error (%) |
|---|---|---|---|
| Bovine shank: GCN-FWI with LS regularization | | | |
| bone | 3359 | 3121 | −7.1 |
| muscle | 1556 | 1557 | 0.1 |
| fat | 1481 | 1488 | 0.5 |
| water | 1484 | 1495 | 0.7 |
| Bovine shank: DS-FWI with LS regularization | | | |
| bone | 3359 | 3102 | −7.7 |
| muscle | 1556 | 1564 | 0.5 |
| fat | 1481 | 1482 | 0.0 |
| water | 1484 | 1477 | −0.5 |
| Bovine shank: C-FWI with LS regularization | | | |
| bone | 3359 | 3045 | −9.3 |
| muscle | 1556 | 1564 | 0.5 |
| fat | 1481 | 1483 | 0.1 |
| water | 1484 | 1477 | −0.5 |
| Bovine shank: C-FWT | | | |
| bone | 3359 | 2801 | −16.6 |
| muscle | 1556 | 1564 | 0.5 |
| fat | 1481 | 1483 | 0.2 |
| water | 1484 | 1482 | −0.1 |
| Bovine shank: C-FWI with LS regularization, 512 grid | | | |
| bone | 3359 | 3035 | −9.7 |
| muscle | 1556 | 1561 | 0.3 |
| fat | 1481 | 1491 | 0.7 |
| water | 1484 | 1476 | −0.6 |

TABLE 11

Bovine shank slice two results: FWI, LS

| Material | Ground truth (m/s) | Inverted (m/s) | Error (%) |
|---|---|---|---|
| Bovine shank slice two: C-FWI with LS regularization | | | |
| bone | 3359 | 3029 | −9.8 |
| muscle | 1556 | 1569 | 0.8 |
| fat | 1481 | 1508 | 1.8 |
| water | 1484 | 1482 | −0.2 |

TABLE 11-continued

Bovine shank slice two results: FWI, LS

| Material | Ground truth (m/s) | Inverted (m/s) | Error (%) |
|---|---|---|---|
| Bovine shank slice two: GCN-FWI with LS regularization | | | |
| bone | 3359 | 2979 | −11.3 |
| muscle | 1556 | 1568 | 0.8 |
| fat | 1481 | 1505 | 1.6 |
| water | 1484 | 1501 | 1.2 |

Results from the second slice (collected 1.9 cm below the first slice) show distinct, but similar, soft tissue patterns and resolution (FIGS. 53A-F) compared to the first slice (FIGS. 51A-D and 52A-E). The second slice demonstrates repeatability and robustness of the inversion techniques and the UST system hardware. Results using the C-FWI with LS regularization and GCN-FWI with LS regularization are shown (FIGS. 53A-F).

Figure 53A:
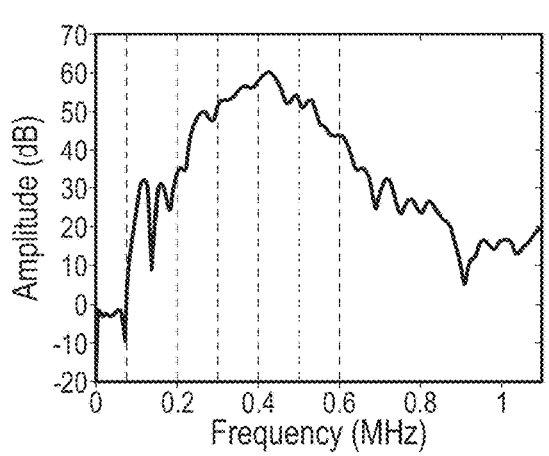
FIGS. 53A-53F illustrate results from a second slice of the bovine shank of FIG. 51D.
Figure 53B:
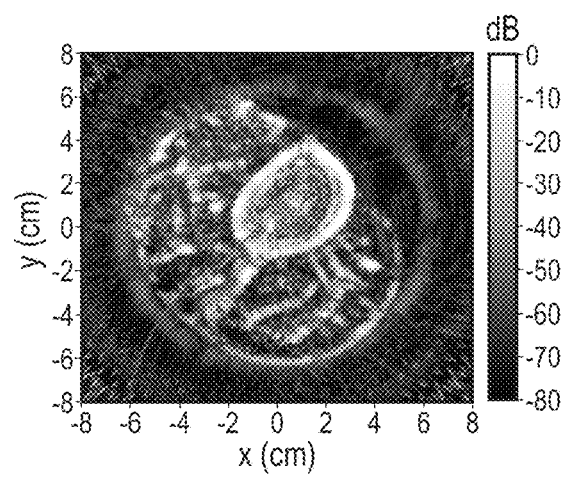
Figure 53C:
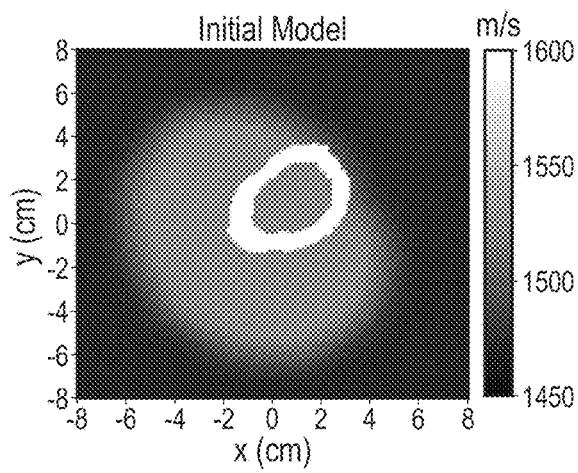
Figure 53D:
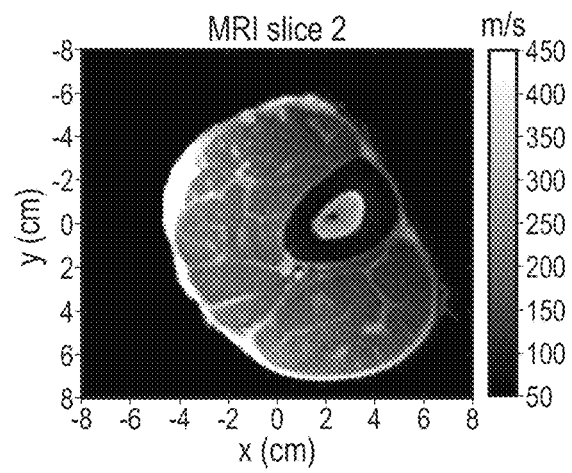
Figure 53E:
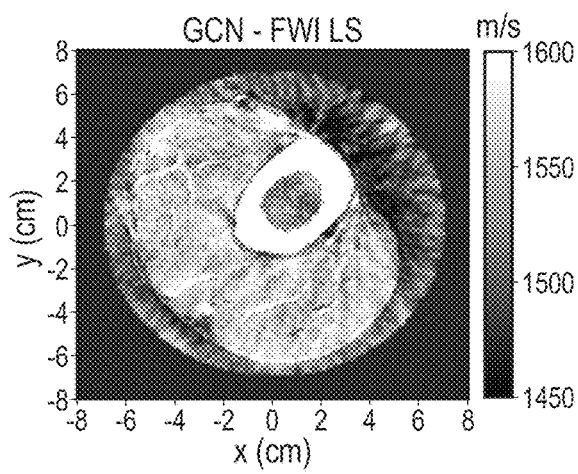
Figure 53F:
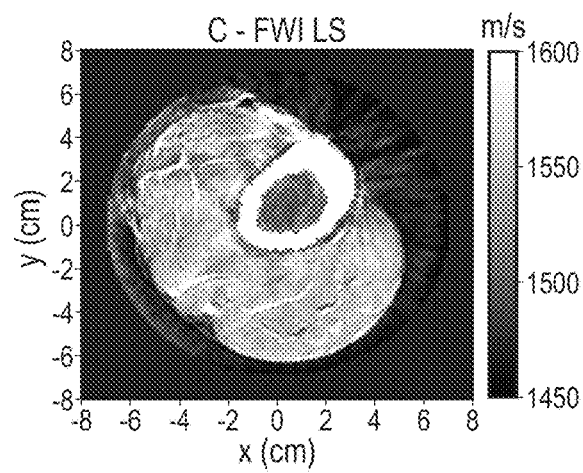

For the second slice, the inversion occurs over five frequency bands (FIG. 53A). The inversions all took approximately three hours, either on a desktop computer or the 72-core computing cluster. The spatial structure of the bone, soft tissue, and water (FIG. 53B) inform the initial sound speed map (FIG. 53C). The image (FIG. 53D) shows the bone geometry as well as the characteristic soft tissue structure of the second bovine shank slice. The bone geometry of the sound speed images (FIGS. 53E-F) is similar to the MRI imagery (FIG. 53D), and the bulk sound speeds are within 10% of the ground truth values (Table 11). This performance is nearly identical to the first slice. The sound speed estimates for the bone and muscle from the first and second slice are within 16 m/s and 5 m/s respectively (Table 9, Table 10) for the C-FWI with LS regularization process.

DISCUSSION

The Full Waveform Inversion (FWI) methods with level set (LS) regularization can produce quantitative sound speed ultrasound images of soft tissue and bone from ex vivo animal tissue models with sound speed error of 10% or less. A commercial ultrasound system with these capabilities can provide for improved prosthetic fittings, tracking and diagnosis of osteoporosis, and muscle health monitoring, without radiation dosage. The current methods show 2D cross-sectional images, but the methods can be expanded to generate volumetric images. In the volumetric cases, the GCN-FWI method can significantly reduce the computation costs of volumetric FWI.

When compared to MRI, the sound speed images obtained have nearly identical spatial resolution. In addition to good resolution, the UST images provide quantitative information about the bone and soft tissue mechanical properties that the MRI images do not. The sound speed images also can call for significantly less complicated, expensive, and potentially dangerous hardware to be obtained relative to MRI or CT. With further development, UST systems may provide better overall diagnostic and cost performance compared MRI or CT systems for certain applications.

Previous studies predominantly apply FWI techniques to soft tissues applications such as for breast cancer detection. Here, the LS technique supplements the FWI technique to regularize the inversion for quantitative imaging of bone and soft tissue. Systems designed for clinical use in the future can include 3D arrays and processes to overcome unwanted (in the 2D case) out-of-plane specular reflections from the bones that would likely occur in clinical practice. The process run times can also be reduced with finer grain parallelization.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method for imaging a biological body segment of soft and hard tissues, comprising:
   a) setting geometry and material properties according to a model of the biological body segment to thereby generate a simulated time series data set, wherein generating simulated time series data employs at least one tissue boundary detection process;
   b) collecting reflective and transmissive time series data of the biological body segment to thereby form an experimental time series data set of images of the biological body segment; and
   c) minimizing the difference between the simulated time series data set and the experimental time series data set, thereby imaging the biological body segment.

2. The method of claim 1, wherein the reflective and transmissive time series data is collected by employing an ultrasound transducer that emits an ultrasound beam of known beam geometry for reflection and transmission at the biological body segment.

3. The method of claim 1, further including modifying the model, modifying the simulated time series data, or modifying both the model and the simulated time series data to more accurately emulate experimental time series data.

4. The method of claim 1, further including modifying the model by at least one of the following: including prior information about biological tissue being imaged; including prior information about a motion trajectory of one or more transducers employed in collecting the reflective and transmissive time series data; including a model of a motion trajectory of one or more transducers employed in collecting the reflective and transmissive time series data; including prior information about a response of one or more transducers employed in collecting the reflective and transmissive time series data; and including a model of a response of one or more transducers employed in collecting the reflective and transmissive time series data.

5. The method of claim 1, including applying a level set technique including a full waveform inversion.

6. The method of claim 1, wherein collecting the reflective and transmissive time series data employs at least one of a water-immersed ultrasound transducer and a laser.

7. The method of claim 1, wherein minimizing the difference between the simulated time series data set and the experimental time series data set includes a full waveform inversion, a level set region segmentation of at least one portion or component of the biological body segment, a regularization of travel time or use of travel time to regularize full waveform inversion, or any combination thereof.

8. The method of claim 1, wherein collecting the reflective and transmissive time series data includes ultrasound tomography that employs a tank-based ultrasound system that includes at least two single-element transducers mounted at a tank of the tomography system, and further including the step of obtaining multi-aperture time series data from the single element transducers.

9. A system for imaging a biological body segment of soft and hard tissues, comprising:
at least one sensor configured to collect reflective and transmissive time series data of the biological body segment; and
a processor configured to:
generate a simulated time series data set based on geometry and material properties according to a model of the biological body segment,
receive from the at least one sensor the collected reflective and transmissive time series data,
generate an experimental time series data set from the collected reflective and transmissive time series data, and
minimize a difference between the simulated time series data set and the experimental time series data set to thereby image the biological body segment.

10. The system of claim 9, further comprising an ultrasound transducer configured to emit an ultrasound beam of known beam geometry for reflection and transmission at the biological body segment.

11. The system of claim 9, wherein the processor is further configured to modify the model to more accurately emulate the experimental time series data.

12. The system of claim 9, wherein the processor is further configured to modify the model to include at least one of the following: prior information about biological tissue being imaged; prior information about a motion trajectory of one or more transducers employed in collecting the reflective and transmissive time series data; a model of a motion trajectory of one or more transducers employed in collecting the reflective and transmissive time series data; prior information about a response of one or more transducers employed in collecting the reflective and transmissive time series data; and a model of a response of one or more transducers employed in collecting the reflective and transmissive time series data.

13. The system of claim 9 wherein the processor is further configured to apply a level set technique including a full waveform inversion.

14. The system of claim 9, wherein the at least one sensor includes a water-immersed ultrasound transducer, one or more lasers, or a combination thereof.

15. The system of claim 9, wherein minimization of the difference between the simulated time series data set and the experimental time series data set includes a full waveform inversion, a level set region segmentation of at least one portion or component of the biological body segment, a regularization of travel time or use of travel time to regularize full waveform inversion, or any combination thereof.

16. The system of claim 9, wherein the system is a tank-based ultrasound tomography system that includes a tank and at least two single-element transducers mounted at a tank of the tomography system, and wherein collection of the reflective and transmissive time series data includes ultrasound tomography.

17. The system of claim 16, wherein the processor is further configured to obtain multi-aperture time series data from the single element transducers.

18. The system of claim 9, wherein the processor is further configured to apply at least one tissue boundary detection process for generation of the simulated time series data.

19. A tank-based ultrasound computed tomography system, comprising:
a) an immersion tank;
b) at least one ultrasound transducer within the immersion tank that emits an ultrasound beam;
c) at least one ultrasound receiver configured to detect reflection and
transmission of the ultrasound beam following reflection and transmission of the ultrasound beam off or through a biological body segment; and
a processor configured to:
receive reflection and transmission data detected by the at least one ultrasound receiver,
generate a simulated time series data set based on geometry and material properties according to a model of the biological body segment,
generate an experimental time series data set from the received reflection and transmission data, and
minimize a difference between the simulated time series data set and the experimental time series data set to thereby image the biological body segment.

20. A method for imaging a biological body segment of soft and hard tissues, comprising:
a) setting geometry and material properties according to a model of the biological body segment to thereby generate a simulated time series data set;
b) collecting reflective and transmissive time series data of the biological body segment to thereby form an experimental time series data set of images of the biological body segment, wherein the reflective and transmissive time series data is collected by employing an ultrasound transducer that emits an ultrasound beam of known beam geometry for reflection and transmission at the biological body segment; and
c) minimizing the difference between the simulated time series data set and the experimental time series data set, thereby imaging the biological body segment.

21. A method for imaging a biological body segment of soft and hard tissues, comprising:
a) setting geometry and material properties according to a model of the biological body segment to thereby generate a simulated time series data set;
b) collecting reflective and transmissive time series data of the biological body segment to thereby form an experimental time series data set of images of the biological body segment, wherein collecting the reflective and transmissive time series data employs at least one of a water-immersed ultrasound transducer and a laser; and
c) minimizing the difference between the simulated time series data set and the experimental time series data set, thereby imaging the biological body segment.

22. A method for imaging a biological body segment of soft and hard tissues, comprising:
a) setting geometry and material properties according to a model of the biological body segment to thereby generate a simulated time series data set;
b) collecting reflective and transmissive time series data of the biological body segment to thereby form an experimental time series data set of images of the biological body segment, wherein collecting the reflective and transmissive time series data includes ultrasound tomography that employs a tank-based ultrasound system that includes at least two single-element transducers mounted at a tank of the tomography system, and further including the step of obtaining multi-aperture time series data from the single element transducers; and c) minimizing the difference between the simulated time series data set and the experimental time series data set, thereby imaging the biological body segment.

* * * * *